(12) United States Patent
Harmange et al.

(10) Patent No.: US 6,939,874 B2
(45) Date of Patent: Sep. 6, 2005

(54) SUBSTITUTED PYRIMIDINYL DERIVATIVES AND METHODS OF USE

(75) Inventors: Jean-Christophe Harmange, Andover, MA (US); John L. Buchanan, Brookline, MA (US); Stuart Chaffee, Cambridge, MA (US); Perry M. Novak, Milford, MA (US); Simon Van Der Plas, Kanata (CA); Xiaotian Zhu, Newton, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 10/225,783

(22) Filed: Aug. 21, 2002

(65) Prior Publication Data

US 2004/0063705 A1 Apr. 1, 2004

Related U.S. Application Data

(60) Provisional application No. 60/314,339, filed on Aug. 22, 2001.

(51) Int. Cl.$^7$ .................. C07D 401/14; A61K 31/4709
(52) U.S. Cl. ...................................... 514/275; 544/324
(58) Field of Search .......................... 544/324; 514/275

(56) References Cited

U.S. PATENT DOCUMENTS

| | | | |
|---|---|---|---|
| 2,585,910 A | 2/1952 | Barton et al. | 260/256.4 |
| 2,585,972 A | 2/1952 | Stacey et al. | 260/256.4 |
| 2,585,979 A | 2/1952 | Vasey | 260/256.4 |
| 2,643,253 A | 6/1953 | Curd et al. | 260/256.4 |
| 4,983,608 A | 1/1991 | Effland et al. | 514/256 |
| 5,043,317 A | 8/1991 | Chapman et al. | 503/227 |
| 5,935,966 A | 8/1999 | Suto et al. | 514/275 |
| 5,958,935 A | 9/1999 | Davis et al. | 514/275 |
| 6,080,858 A | 6/2000 | Schumacher | 544/99 |

FOREIGN PATENT DOCUMENTS

| | | |
|---|---|---|
| EP | 0 379 806 B1 | 4/1996 |
| EP | 0 945 443 A1 | 9/1999 |
| EP | 1 040 831 A2 | 10/2000 |
| GB | 794043 | 4/1958 |
| WO | WO 94/26733 | 11/1994 |
| WO | WO 95/33750 | 12/1995 |
| WO | WO 97/19065 | 5/1997 |
| WO | WO 98/41512 | 9/1998 |
| WO | WO 99/31073 | 6/1999 |
| WO | WO 99/41253 | 8/1999 |
| WO | WO 99/50250 | 10/1999 |
| WO | WO 00/27825 | 5/2000 |
| WO | WO 00/39101 | 7/2000 |
| WO | WO 00/53595 | 9/2000 |
| WO | WO 00/59892 | 10/2000 |
| WO | WO 00/78731 | 12/2000 |
| WO | WO 01/00213 | 1/2001 |
| WO | WO 01/19825 | 3/2001 |
| WO | WO 01/22938 | 4/2001 |
| WO | WO 01/29009 | 4/2001 |
| WO | WO 01/40218 | * 6/2001 |
| WO | WO 01/47921 | 7/2001 |
| WO | WO 01/55116 | * 8/2001 |
| WO | WO 01/60816 | 8/2001 |
| WO | WO 01/72717 | 10/2001 |
| WO | WO 01/72745 | 10/2001 |
| WO | WO 01/85700 | 11/2001 |
| WO | WO 02/22601 | 3/2002 |
| WO | WO 02/46170 | 6/2002 |
| WO | WO 02/46171 | 6/2002 |
| WO | WO 02/46184 | 6/2002 |
| WO | WO 02/47690 | 6/2002 |
| WO | WO 02/48147 | 6/2002 |
| WO | WO 02/48148 | 6/2002 |
| WO | WO 02/50065 | 6/2002 |
| WO | WO 02/50066 | 6/2002 |
| WO | WO 02/057259 | 7/2002 |
| WO | WO 02/059110 | 8/2002 |

OTHER PUBLICATIONS

Girnita et al., Mdm2–dependent ubiquitination and degradation of the insulin–like growth factor 1 receptor, PNAS, vol. 100, No. 14, pp. 8247–8252, 2003.*

Romano, The complex biology of the Receptor for the Insulin–like Growth Factor–1, Drug News & Perspectives, Abstract, vol. 16, No. 8, Oct. 2003.*

Khandwala et al., The Effects of Insulin–like Growth Factors on Tumorigenesis and Neoplastic Growth, Endocrine Reviews, 21 (3), pp. 215–244, 2000.*

Ellis et al., Insulin–like Growth Factors in human breast cancer, Breast Cancer Research and Treatment 52:175–184, 1998.*

Traxler, Review: Oncologic, Endocrine & Metabolic, Protein tyrosine kinase inhibitors in cancer treatment, Exp. Opin. Ther. Patents, 7(6), pp. 571–588, 1997.*

Simone, Oncology: Introduction,Cecil Textbook of Medicine, 20th Edition, vol. 1, pp. 1004–1010, 1996.*

Ghoneim et al., "Synthesis and Evaluation of Some 2–, 4–, and 2,4–Disubstituted–6–Methylpyrimidine Derivatives for Antimicrobial Activity" (1978) 28: 117–126.

* cited by examiner

*Primary Examiner*—Deepak Rao
(74) *Attorney, Agent, or Firm*—Joseph W. Bulock

(57) ABSTRACT

The invention encompasses compounds, analogs, prodrugs and pharmaceutically acceptable salts thereof, pharmaceutical compositions, uses and methods for prophylaxis and treatment of cancer.

17 Claims, No Drawings

SUBSTITUTED PYRIMIDINYL DERIVATIVES AND METHODS OF USE

This application claims the benefit of U.S. Provisional Application No. 60/314,339, filed Aug. 22, 2001, which is hereby incorporated by reference.

FIELD OF THE INVENTION

This invention is in the field of pharmaceutical agents and specifically relates to compounds, compositions, uses and methods for treating cancer and related disorders.

BACKGROUND OF THE INVENTION

Phosphoryl transferases are a large family of enzymes that transfer phosphorous-containing groups from one substrate to another. Kinases are a class of enzymes that function in the catalysis of phosphoryl transfer. The protein kinases constitute the largest subfamily of structurally related phosphoryl transferases and are responsible for the control of a wide variety of signal transduction processes within the cell. Almost all kinases contain a similar 250–300 amino acid catalytic domain. The protein kinases may be categorized into families by the substrates they phosphorylate (e.g., protein-tyrosine, protein-serine/threonine, etc.). Protein kinase sequence motifs have been identified that generally correspond to each of these kinase families. Lipid kinases (e.g. PI3K) constitute a separate group of kinases with structural similarity to protein kinases.

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms. It must be noted, however, that an individual protein kinase may be regulated by more than one mechanism. These mechanisms include, for example, autophosphorylation, transphosphorylation by other kinases, protein-protein interactions, protein-lipid interactions, protein-polynucleotide interactions, ligand binding, and post-translational modification.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Protein kinases represent a large family of proteins which play a central role in the regulation of a wide variety of cellular processes, maintaining control over cellular function. A partial list of such kinases includes abl, AKT, bcr-abl, Blk, Brk, Btk, c-kit, c-met, c-src, CDK1, CDK2, CDK3, CDK4, CDK5, CDK6, CDK7, CDK8, CDK9, CDK10, cRaf1, CSFir, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ron, tie, tie2, TRK, Yes, and Zap70. Inhibition of such kinases has become an important therapeutic target.

A major feature of malignant cells is the loss of control over one or more cell cycle elements. These elements range from cell surface receptors to the regulators of transcription and translation, including the insulin-like growth factors, insulin growth factor-I (IGF-1) and insulin growth factor-2 (IGF-2). [M. J. Ellis, "The Insulin-Like Growth Factor Network and Breast Cancer", Breast Cancer, Molecular Genetics, Pathogenesis and Therapeutics, Humana Press 1999]. The insulin growth factor system consists of families of ligands, insulin growth factor binding proteins, and receptors. A major physiological role of the IGF-1 system is the promotion of normal growth and regeneration, and overexpressed IGF-1R can initiate mitogenesis and promote ligand-dependent neoplastic transformation. Furthermore, IGF-1R plays an important role in the establishment and maintenance of the malignant phenotype.

IGF-1R exists as a heterodimer, with several disulfide bridges. The tyrosine kinase catalytic site and the ATP binding site are located on the cytoplasmic portion of the beta subunit.

Unlike the epidermal growth factor (EGF) receptor, no mutant oncogenic forms of the IGF-1R have been identified. However, several oncogenes have been demonstrated to affect IGF-1 and IGF-1R expression.

The correlation between a reduction of IGF-1R expression and resistance to transformation has been seen. Exposure of cells to the mRNA antisense to IGF-1R RNA, prevents soft agar growth of several human tumor cell lines.

Apoptosis is a ubiquitous physiological process used to eliminate damaged or unwanted cells in multicellular organisms. Disregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, regulators of apoptosis have become an important therapeutic target. It is now established that a major mode of tumor survival is escape from apoptosis. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

WO01/00213, published 4 Jan. 2001, describes substituted pyrimidines as SRC kinase inhibitors. WO01/40218, published 7 Jun. 2001, describes arylamine derivatives for use as anti-telomerase agents. WO00/39101, published 6 Jul. 2000, describes substituted pyrimidines as anti-cancer agents. WO01/29009, published 26 Apr. 2001, describes substituted pyrimidines as kinase inhibitors. WO00/78731, published 28 Dec. 2000, describes cyano substituted pyrimidines as kinase inhibitors. WO00/53595, published 14 Sep. 2000, describes substituted pyrimidines as kinase inhibitors. WO00/39101, published 6 Jul. 2000, describes amino substituted pyrimidines as kinase inhibitors. WO00/59892, published 12 Oct. 2000, describes amino substituted pyrimidines as kinase inhibitors. WO97/19065, published 29 May 1997, describes 2-anilino-pyrimidines as kinase inhibitors. EP379806, published 10 Apr. 1996, describes substituted pyrimidines for the treatment of neurological disorders. EP1040831, published 4 Oct. 2000, describes substituted pyrimidines as CRF antagonists. Amino substituted pyrimidines were cited in Chem. Abstr. 112:191083. Amino substituted pyrimidines were cited in Chem. Abstr. 72:1114009. WO95/33750, published 14 Dec. 1995, describes substituted pyrimidines as CRF antagonists. WO94/26733, published 24 Nov. 1994, describes pyrimidine derivatives as ligands for dopamine receptors. U.S. Pat. No. 5,958,935 describes substituted pyrimidines as kinase inhibitors. U.S. Pat. No. 4,983,608, describes pyrrolyl-amino substituted pyrimidines as analgesic agents. U.S. Pat. No. 5,043,317, describes amino substituted pyrimidines as dyes. U.S. Pat. No. 5,935,966 describes carboxylate substituted pyrimidines as anti-inflammatories. U.S. Pat. No. 6,080,858 describes a process for preparing substituted pyrimidines. WO99/50250, published 7 Oct. 1999, describes amino substituted pyrimidines for the treatment of HIV infection. EP945443, published 29 Sep. 1999, describes amino substituted pyrimidines for the treatment of HIV infection. WO99/31073, published 24 Jun. 1999, describes amide substituted pyrimidines. WO00/27825, published 18 May 2000, describes amino substituted pyrimidines for the treatment of HIV infection. WO01/22938, published 5 Apr. 2001, describes amino substituted pyrimidines for the treatment of HIV infection. WO99/41253, published 19 Aug. 1999, describes amino substituted pyrimidines for the treatment of viral infection. WO01/19825, published 22 Mar. 2001, describes amino substituted pyrimidines as synthetic intermediates. WO01/47921, published 5 Jul. 2001, describes amino substituted pyrimidines as kinase inhibitors. WO01/72745, published 4 Oct. 2001, describes 4-heteroaryl-substituted pyrimidines as inhibitors of CDK's. WO01/72717, published 4 Oct. 2001, describes 4-amino-5-cyanopyrimidines as inhibitors of CDK's. WO01/85700, published 15 Nov. 2001, describes pyrimidines as HIV replication inhibitors. WO02/22601, published 21 Mar. 2002, describes 4-(pyrazol-5-ylamino)pyrimidines as kinase inhibitors. WO02/46184, published describes 4-(4-pyrazolyl)-pyrimidines as kinase inhibitors. WO02/46170, published 13 Jun. 2002, describes 2-anilino-pyrimidines as inhibitors of JNK. WO02/46171, published 13 Jun. 2002, describes 2-anilino-pyrimidines as inhibitors of IKK. WO02/47690, published 20 Jun. 2002, describes 4-arylamino-pyrimidines as kinase inhibitors. WO02/48147, published 20 Jun. 2002, describes pyrimidines as kinase inhibitors. WO02/48148, published 20 Jun. 2002, describes pyrimidines as kinase inhibitors. Ghoneim et al., Egypt J. Pharm. Sci., 28, 117–26 (1987)) describe N,N'-bis(3,5-dimethyl-4-isoxazolyl)-6-methyl-2,4-pyrimidinediamine. Ghoneim et al., J. Indian Chem. Soc., 63, 914–17 (1986)) describe N,N'-bis(3,5-dimethyl-4-isoxazolyl)-6-methyl-2,4-pyrimidinediamine. WO02/50065, published 27 Jun. 2002, describes 2-(5-pyrazolylamino)-pyrimidines as kinase inhibitors. WO02/50066, published 27 Jun. 2002, describes 2-(5-pyrazolylamino)-pyrimidines as kinase inhibitors. WO02/57259, published 25 Jul. 2002, describes 4-(5-pyrazolylamino)-pyrimidines as kinase inhibitors. WO02/59110, published 1 Aug. 2002, describes amino substituted pyrimidines as inhibitors of VEGFR2.

However, compounds of the current invention have not been described as inhibitors for the treatment of cancer.

DESCRIPTION OF THE INVENTION

A class of compounds useful in treating cancer and is defined by Formula I

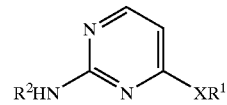

wherein X is S, O, or NH,
preferably NH;
wherein $R^1$ is quinolyl, isoquinolyl, purinyl, benzthiazolyl, benzoxazolyl, benzoxadiazolyl, benzothiadiazolyl, benzisoxazolyl, benzisothiazolyl, benzotriazolyl, indolizinyl, pteridinyl, acridinyl, carbazolyl, indolinyl, benzofuryl, benzthienyl, quinolizinyl, pyridyl, triazinyl, pyrazinyl, pyrimidinyl, pyridazinyl, phthalazinyl, naphthyridinyl, tetrazolyl, quinoxalinyl, quinazolinyl and cinnolinyl, wherein $R^1$ is optionally substituted with 1–4 substituents independently selected from $R^3$;
wherein $R^2$ is selected from
H,
$C_{1-10}$-alkyl,
$C_{2-10}$-alkenyl,
$C_{2-10}$-alkynyl,
$C(O)R^5$,
$COOR^5$,
$C(O)NR^5R^5$,
$S(O)_nR^5$,
$C_{3-10}$-cycloalkyl,
$C_{4-10}$-cycloalkenyl,
aryl optionally substituted with 1–5 substituents independently selected from $R^3$,
$R^4$,
$C_{1-10}$-alkyl substituted with 1–3 substituents independently selected from aryl, $R^7$ and $R^4$,
$C_{3-10}$-cycloalkyl substituted with 1–3 substituents independently selected from aryl, $R^7$ and $R^4$, and
$C_{2-10}$-alkenyl substituted with 1–3 substituents independently selected from aryl, $R^7$ and $R^4$;
preferably $C_{1-6}$-alkyl,
$C_{2-6}$-alkenyl,
$C_{2-6}$-alkynyl,
$C_{3-6}$-cycloalkyl,
$C_{4-6}$-cycloalkenyl,
$R^4$,
phenyl optionally substituted with 1–4 substituents independently selected from $R^3$, $C_{1-6}$-alkyl substituted with 1–3 substituents independently selected from aryl, $R^7$ and $R^4$,
$C_{3-6}$-cycloalkyl substituted with 1–4 substituents independently selected from aryl, $R^7$ and $R^4$, and
$C_{2-6}$-alkenyl substituted with 1–3 substituents independently selected from aryl and $R^4$,
more preferably $R^4$, and phenyl optionally substituted with 1–4 substituents independently selected from $R^3$,
even more preferably 3,4,5-trimethoxyphenyl, 3,4-dimethoxyphenyl, 2,5-dimethoxyphenyl, 3,4-dimethoxy-6-methylphenyl, quinolinyl, benzimidazolyl, indazolyl, 3-aminosulfonylphenyl and 4-aminosulfonylphenyl;

wherein $R^3$ is independently selected from

H,
$C_{1-10}$-alkyl,
$C_{2-10}$-alkenyl,
$C_{2-10}$-alkynyl,
$C_{3-10}$-cycloalkyl,
$C_{4-10}$-cycloalkenyl,
aryl,
$R^4$,
halo,
$SR^5$,
$OR^5$,
$OC(O)R^5$,
$NR^5R^5$,
$NR^5R^6$,
$COOR^5$,
$NO_2$,
CN,
$C(O)R^5$,
$C(O)C(O)R^5$,
$C(O)NR^5R^5$,
$S(O)_nR^5$,
$S(O)_nNR^5R^5$,
$NR^5C(O)NR^5R^5$,
$NR^5C(O)C(O)R^5$,
$NR^5C(O)R^5$,
$NR^5(COOR^5)$,
$NR^5C(O)R^4$,
$NR^5S(O)_nNR^5R^5$,
$NR^5S(O)_nR^5$,
$NR^5S(O)_nR^4$,
$NR^5C(O)C(O)NR^5R^5$,
$NR^5C(O)C(O)NR^5R^6$,
$C_{1-10}$-alkyl substituted with 1–3 substituents independently selected from aryl, $R^7$ and $R^4$; and
$C_{2-10}$-alkenyl substituted with 1–3 substituents independently selected from aryl, $R^7$ and $R^4$;
preferably selected from
$C_{1-6}$-alkyl,
$C_{2-6}$-alkenyl,
$C_{2-6}$-alkynyl,
$C_{3-6}$-cycloalkyl,
$C_{4-6}$-cycloalkenyl,
phenyl,
$R^4$,
halo,
$SR^5$,
$OR^5$,
$OC(O)R^5$,
$NR^5R^5$,
$NR^5R^6$,
$COOR^5$,
$NO_2$,
CN,
$C(O)R^5$,
$C(O)NR^5R^5$,
$S(O)_nR^5$,
$S(O)_nNR^5R^5$,
$NR^5C(O)NR^5R^5$,
$NR^5C(O)R^5$,
$NR^5(COOR^5)$,
$NR^5C(O)R^4$,
$NR^5S(O)_nNR^5R^5$,
$NR^5S(O)_nR^5$,
$NR^5S(O)_nR^4$,
$C_{1-6}$-alkyl substituted with 1–3 substituents independently selected from aryl, $R^7$ and $R^4$; and
$C_{2-6}$-alkenyl substituted with 1–3 substituents independently selected from aryl, $R^7$ and $R^4$;
more preferably $C_{1-4}$-alkyl, $C_{2-4}$-alkenyl, $C_{2-4}$-alkynyl, phenyl, $R^4$, chloro, fluoro, bromo, —$CF_3$, $C_{1-4}$-alkoxy, phenoxy, heterocyclyloxy, benzyloxy, $C_{1-4}$-alkylcarbonyloxy, amino, alkylamino, phenylamino, carboxy, $C_{1-4}$-alkoxycarbonyl, nitro, cyano, $C_{1-4}$-alkylcarbonyl, aminocarbonyl, $C_{1-4}$-alkylaminocarbonyl, $C_{1-4}$-alkylsulfonyl, $C_{1-4}$-alkylaminosulfonyl, benzyl, $C_{1-4}$-alkoxyalkyl, $C_{1-4}$-aminoalkyl, $C_{1-4}$-alkylaminoalkyl, and 5–6-membered heterocyclyl-$C_{1-4}$-alkyl; and
even more preferably methyl, ethyl, propyl, tert-butyl, isopropyl, phenyl, chloro, fluoro, bromo, trifluoromethyl, methoxy, phenoxy, benzyloxy, acetyl, amino, methylamino, phenylamino, carboxy, ethoxycarbonyl, nitro, cyano, methylcarbonyl, aminocarbonyl, methylaminocarbonyl, methylsulfonyl, methylaminosulfonyl, benzyl, methoxymethyl, aminomethyl, N,N-dimethylaminoethyl and furylmethyl;

wherein $R^4$ is independently a 5–8 membered monocyclic, 8–12 membered bicyclic, or 11–14 membered tricyclic saturated, partially saturated or unsaturated ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by 1–2 substituents independently selected from $C_{1-10}$-alkyl, $C_{2-10}$-alkenyl, $C_{2-10}$-alkynyl, $C_{3-10}$-cycloalkyl, $C_{4-10}$-cycloalkenyl, halo, haloalkyl, sulfo, oxo, $SR^5$, $OR^5$, $NR^5R^5$, $NR^5R^6$, $NR^6R^6$, $COOR^5$, nitro, cyano, $S(O)_nR^5$, $S(O)_nNR^5R^5$, $C(O)R^5$ and $C(O)NR^5R^5$;

preferably a 5–7 membered monocyclic, or 8–11 membered bicyclic, saturated, partially saturated or unsaturated ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by 1–2 substituents independently selected from $C_{1-6}$-alkyl, $C_{2-6}$-alkenyl, $C_{2-6}$-alkynyl, halo, $C_{1-6}$-haloalkyl, oxo, $SR^5$, $OR^5$, $NR^5R^5$, $COOR^5$, nitro, cyano, $S(O)_nR^5$, $S(O)_nNR^5R^5$, $C(O)R^5$ and $C(O)NR^5R^5$;

more preferably 5–6 membered monocyclic, or 8–10 membered bicyclic, saturated, partially saturated or unsaturated ring system comprising 1–3 heteroatoms if monocyclic, 1–6 heteroatoms if bicyclic, said heteroatoms independently selected from O, N, or S, which may be saturated or unsaturated, and wherein 0, 1, 2 or 3 atoms of each ring may be substituted by 1 or 2 substituents independently selected from $C_{1-4}$-alkyl, halo, $C_{1-6}$-haloalkyl, oxo, $OR^5$, $NR^5R^5$, $COOR^5$, nitro, cyano, $S(O)_nR^5$, $S(O)_nNR^5R^5$, $C(O)R^5$ and $C(O)NR^5R^5$; and even more preferably quinolyl, isoquinolyl, indazolyl, imidazolyl, pyrazolyl, pyrrolyl, indolyl, isoindolyl, purinyl, triazolyl, and naphthyridinyl, wherein $R^4$ is optionally substituted by one or more substituents independently selected from methyl, isopropyl, tert-butyl, fluoro, chloro, —$CF_3$, oxo, methoxy, phenoxy, amino, methylamino, phenylamino, carboxy, ethoxycarbonyl, nitro, cyano, methylcarbonyl, aminocarbonyl, methylaminocarbonyl, methylsulfonyl and methylaminosulfonyl;

wherein $R^5$ is independently selected from H, $C_{1-10}$-alkyl, $C_{2-10}$-alkenyl, $C_{2-10}$-alkynyl, $C_{3-10}$-cycloalkyl, $C_{4-10}$-cycloalkenyl, $R^4$, $C_1$–$C_{10}$ alkyl substituted with 1–3 substituents independently selected from aryl, $R^7$ and $R^4$;

aryl optionally substituted with 1–3 substituents independently selected from $R^3$ $C_3$–$C_{10}$ cycloalkyl substituted with 1–3 substituents independently selected from aryl, $R^7$ and $R^4$; and $C_2$–$C_{10}$ alkenyl substituted with 1–3 substituents independently selected from aryl, $R^7$ and $R^4$;

preferably selected from H, $C_{1-6}$-alkyl, and phenyl optionally substituted with 1–3 substituents independently selected from $R^3$;

more preferably H, $C_{1-6}$-alkyl, and phenyl optionally substituted with 1–3 substituents independently selected from $C_{1-4}$-alkyl, chloro, fluoro, bromo, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

wherein $R^6$ is selected from $C(O)R^5$, $COOR^5$, $C(O)NR^5R^5$ and $S(O)_nR^5$;

wherein $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, $OC(O)NR^{10}R^{10}$, $C(O)NR^{10}R^{10}$, $N(R^{10})C(O)R^{10}$, $N(R^{10})(COOR^{10})$ and $S(O)_nNR^{10}R^{10}$; and preferably halo, $OR^{10}$, $NR^{10}R^{10}$, $COOR^{10}$ and CN;

wherein n is 1 or 2;

and pharmaceutically acceptable salts thereof.

The invention also relates to compounds of Formula II

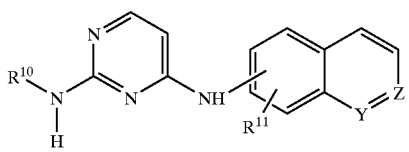

II wherein Y and Z are N or CH, provided one of Y and Z is N and the other is CH;

wherein $R^{10}$ is selected from phenyl, and 5–10 membered heterocyclyl; wherein $R^{10}$ is optionally substituted with 1–4 substituents selected from $R^{11}$;

wherein $R^{11}$ is selected from H, $C_1$–$C_3$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^2$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^2$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; wherein $R^{11}$ can be attached in either ring of the bicyclic substituent;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, $R^4$, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable salts thereof.

The invention also relates to compounds of Formulas IIIa and IIIb

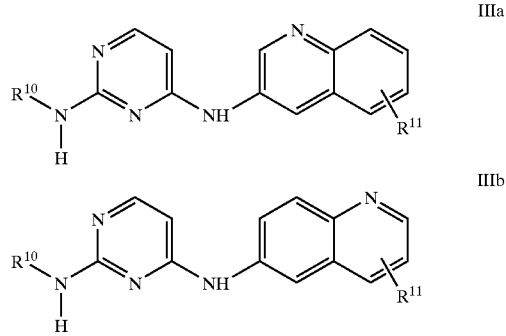

wherein $R^{10}$ is selected from phenyl and 5–10 membered heterocyclyl; wherein $R^{10}$ is optionally substituted with 1–4 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^2$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; wherein $R^{11}$ can be attached in either ring of the quinolyl substituent;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable salts thereof.

The invention also relates to compounds of Formula I'

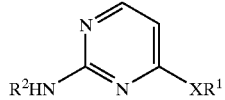

I' wherein X is selected from S, O and NR;
  preferably O, NH and NR;
    more preferably NH and NR;
wherein R is selected from $C_{1-3}$-alkoxycarbonyl-$C_{1-3}$-alkyl, —(CH$_2$)$_{0-4}$—R$^a$, —C$_{2-4}$-alkenyl-R$^a$, and —C$_{2-4}$-alkynyl-R$^a$;
  preferably H, methyl, optionally substituted phenyl, —(CH$_2$)$_{2-3}$—R$^a$, —C$_{2-3}$-alkenyl-R$^a$, and —C$_{2-3}$-alkynyl-R$^a$;
    more preferably H, methyl, —(CH$_2$)$_{2-3}$—R$^a$, —C$_{2-3}$-alkenyl-R$^a$, and 2,6-disubstituted phenyl;
      particularly H, methyl, 2,6-dimethylphenyl, and —C$_2$-alkenyl-R$^a$;
wherein R$^a$ is independently selected from H, optionally substituted phenyl, optionally substituted 5–6-membered heterocyclyl, —OR$^b$ and —NR$^b$R$^b$;
  preferably H, optionally substituted phenyl, optionally substituted 5–6-membered heterocyclyl, and —NR$^b$R$^b$;
    more preferably H, optionally substituted phenyl, and optionally substituted 5–6-membered heterocyclyl;
wherein R$^b$ is independently selected from H, $C_{1-3}$ alkyl, optionally substituted phenyl, and optionally substituted 5–6-membered heterocyclyl;
  preferably H, $C_{1-3}$ alkyl, optionally substituted phenyl, and optionally substituted 5–6-membered heterocyclyl;
wherein R$^1$ is selected from quinolyl, isoquinolyl, purinyl, benzimidazolyl, benzthiazolyl, benzoxadiazolyl, benzothiadiazolyl, benzisoxazolyl, benzisothiazolyl, benzotriazolyl, indolizinyl, benzoxazolyl, pteridinyl, acridinyl, carbazolyl, indolinyl, imidazo[1,2-a]pyridinyl, benzofuryl, 1,1-dioxo-benzothienyl, benzthienyl, quinolizinyl, pyridyl, triazinyl, pyrazinyl, pyrimidinyl, pyridazinyl, phthalazinyl, naphthyridinyl, tetrazolyl, quinoxalinyl, quinazolinyl, cinnolinyl, dibenzofuryl, phenanthrolinyl, and perimidinyl, wherein R$^1$ is optionally substituted with 1–4 substituents independently selected from R$^3$;
  preferably quinolyl, isoquinolyl, imidazo[1,2-a]pyridinyl, benzimidazolyl, benzthiazolyl, indolinyl, pyridyl, and quinoxalinyl, wherein R$^1$ is optionally substituted with 1–3 substituents independently selected from R$^3$;
    more preferably 3-quinolyl, 6-quinolyl, and 3-isoquinolyl;
wherein R$^2$ is selected from R$^4$ and aryl optionally substituted with 1–5 substituents independently selected from R$^3$;
  preferably R$^4$ and aryl optionally substituted with 1–3 substituents independently selected from R$^3$;
    more preferably naphthyl, 2,3-dihydro-indolyl, 1,3-benzodioxolyl, indolyl, 1,3-dioxo-isoindolyl, indazolyl, pyridyl, quinolyl, isoquinolyl, benzothiazolyl, 1,2,3-benzotriazolyl, benzimidazolyl, and phenyl; wherein R$^2$ is optionally substituted with 1–3 substituents independently selected from R$^3$;
      even more preferably 2-naphthyl, 2,3-dihydro-indol-6-yl, 1,3-benzodioxol-5-yl, 5-indolyl, 4-indolyl, 1,3-dioxo-isoindol-5-yl, 5-indazolyl, 6-indazolyl, 3-pyridyl, 3-quinolyl, 6-quinolyl, isoquinolyl, benzothiazol-6-yl, benzothiazol-5-yl, 1,2,3-benzotriazol-5-yl, 6-benzimidazolyl, 5-pyridyl, and phenyl;
        wherein R$^2$ is optionally substituted with 1–3 substituents independently selected from hydroxy, methoxy, ethoxy, cyano, nitro, chloro, fluoro, bromo, dimethylamino, dimethylaminoethyl, 3-dimethylaminopropoxy, methoxycarbonyl, methylcarbonyl, CH$_3$C(O)N(CH$_3$)—, methylcarbonylamino, methyl, ethyl, isopropyl, pyrrolidin-1-ylcarbonylethenyl, pyrrolidin-1-ylcarbonylethyl, pyrrolidin-1-ylpropyl, ethynyl, acetyl, ethoxycarbonylbutyl, carboxybutyl, 2-(1-methyl-piperidin-4-yl)-ethoxy, 2-(4-methyl-piperazin-1-yl)ethoxy, 3-(4-methyl-piperazin-1-yl)-propoxy, 3-(piperidin-1-yl)propoxy, 2-piperidin-1-yl-ethoxy, 2-morpholin-4-yl-ethoxy, pentafluoroethyl, trifluoromethyl, trifluoromethoxy, difluoromethoxy, aminocarbonyl, aminosulfonyl, N,N'-dipropylaminosulfonyl, hydroxypropylaminosulfonyl, (2-thiazolyl)aminosulfonyl, butylaminosulfonyl, methylcarbonylaminosulfonyl, methylsulfonyl, 1-methyl-piperidin-4-ylmethoxy, 1-tert-butoxycarbonyl-piperazin-4-yl, 4-morpholinyl, 4-methylpiperzin-1-yl, 4-piperazinyl, 4-isopropyl-piperazin-1-yl, and oxazol-5-yl;
          particularly 3,4,5-trimethoxyphenyl, 3-(dimethylaminoethyl)-4-methoxyphenyl, 3-(1,3-oxazol-5-yl)phenyl, 4-[3-(piperidin-1-yl)propoxy]phenyl, 3-methoxy-4-(pyrrolidin-1-ylpropyl)phenyl, and 3,4-dimethoxy-6-methylphenyl;
wherein R$^3$ is independently selected from
  H,
  $C_{1-10}$-alkyl,
  $C_{2-10}$-alkenyl,
  $C_{2-10}$-alkynyl,
  $C_{1-10}$-haloalkyl,
  $C_{3-10}$-cycloalkyl,
  $C_{4-10}$-cycloalkenyl,
  aryl,
  R$^4$,
  halo,
  SR$^5$,
  OR$^5$,
  OC(O)R$^5$,
  NR$^5$R$^5$,
  NR$^5$R$^6$,
  COOR$^5$,
  nitro,
  cyano,
  C(O)R$^5$,
  C(O)C(O) R$^5$,
  C(O)NR$^5$R$^5$,
  S(O)$_n$R$^5$,
  S(O)$_n$NR$^5$R$^5$,
  S(O)$_n$NR$^5$R$^6$, NR⁵C(O)NR⁵R⁵,
NR⁵C(O)C(O)R⁵,
NR⁵C(O)R⁵,
NR⁵COOR⁵,
NR⁵C(O)R⁴,
NR⁵S(O)$_n$NR⁵R⁵,
NR⁵S(O)$_n$R⁵,
NR⁵S(O)$_n$R⁴,
NR⁵C(O)C(O)NR⁵R⁵,
NR⁵C(O)C(O)NR⁵R⁶, $C_{1-10}$-alkyl substituted with 1–3 substituents independently selected from aryl, R⁷ and R⁴; and $C_{2-10}$-alkenyl substituted with 1–3 substituents independently selected from aryl, R⁷ and R⁴;

preferably H, $C_{1-4}$-alkyl, $C_{2-4}$-alkenyl, $C_{2-4}$-alkynyl, phenyl, $C_{6-10}$-cycloalkyl, R⁴, chloro, fluoro, bromo, trifluoromethyl, hydroxy, $C_{1-4}$-alkoxy, $C_{1-4}$-haloalkoxy, phenoxy, heterocyclyloxy, benzyloxy, $C_{1-4}$-alkylcarbonyloxy, amino, alkylamino, phenylamino, carboxy, $C_{1-4}$-alkoxycarbonyl, nitro, cyano, $C_{1-4}$-alkylcarbonyl, aminocarbonyl, $C_{1-4}$-alkylaminocarbonyl, $C_{1-4}$-alkylsulfonyl, $C_{1-4}$-alkylaminosulfonyl, benzyl, $C_{1-4}$-alkoxyalkyl, $C_{1-4}$-aminoalkyl, $C_{1-4}$-alkylaminoalkyl, and 5–6-membered heterocyclyl-$C_{1-4}$-alkyl;

more preferably H, halo, $C_{1-3}$-alkyl, $C_{2-3}$-alkenyl, $C_{2-3}$-alkynyl, phenyl, hydroxy, $C_{1-3}$-haloalkoxy, $C_{1-3}$-alkoxy, —C(O)—$C_{1-3}$-alkyl, and $C_{1-3}$-haloalkyl;

particularly H, hydroxy, iodo, methyl, acetyl, trifluoromethyl, methoxy, phenyl and trifluoromethoxy;

wherein R⁴ is independently a 5–8 membered monocyclic, 8–12 membered bicyclic, or 11–14 membered tricyclic saturated, partially saturated or unsaturated ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from $C_{1-10}$-alkyl, $C_{2-10}$-alkenyl, $C_{2-10}$-alkynyl, $C_{3-10}$-cycloalkyl, $C_{4-10}$-cycloalkenyl, halo, haloalkyl, sulfo, oxo, SR⁵, OR⁵, NR⁵R⁵, NR⁵R⁶, NR⁶R⁶, COOR⁵, nitro, cyano, S(O)$_n$R⁵, S(O)$_n$NR⁵R⁵, C(O)R⁵, C(O)NR⁵R⁵ and 6-membered heteroaryl optionally substituted with 1–3 substituents independently selected from R³;

preferably 2,3-dihydro-indolyl, 1,3-benzodioxolyl, indolyl, 1,3-dioxo-isoindolyl, indazolyl, pyridyl, quinolyl, isoquinolyl, benzothiazolyl, 1,2,3-benzotriazolyl, benzimidazolyl, and pyridyl; wherein R⁴ is optionally substituted with hydroxy, $C_{1-3}$-alkoxy, cyano, nitro, halo, $C_{1-3}$-alkyl, di-$C_{1-3}$-alkylamino, di-$C_{1-3}$-alkylamino-$C_{1-3}$-alkyl, di-$C_{1-3}$-alkylamino-$C_{1-3}$-alkoxy, $C_{1-3}$-alkylcarbonyl, $C_{1-3}$-alkoxycarbonyl, $C_{1-3}$-alkylcarbonylamino, pyrrolidinylcarbonyl-$C_{2-3}$-alkenyl, pyrrolidinylcarbonyl-$C_{1-3}$-alkyl, pyrrolidinyl-$C_{1-3}$-alkyl, $C_{2-3}$-alkynyl, acetyl, $C_{1-3}$-alkylcarbonyl-$C_{1-3}$-alkyl, carboxy-$C_{1-3}$-alkyl, (piperidinyl)-$C_{1-3}$-alkoxy, (piperazinyl)-$C_{1-3}$-alkoxy, 2-morpholinyl-$C_{1-3}$-alkoxy, $C_{1-3}$-haloalkyl, $C_{1-3}$-haloalkoxy, aminocarbonyl, aminosulfonyl, $C_{1-3}$-alkylaminosulfonyl, hydroxy-$C_{1-3}$-alkylaminosulfonyl, (thiazolyl)aminosulfonyl, $C_{1-4}$-alkylaminosulfonyl, $C_{1-3}$-alkylcarbonylaminosulfonyl, $C_{1-3}$-alkylsulfonyl, $C_{1-3}$-alkoxycarbonyl-piperazinyl, morpholinyl, $C_{1-3}$-alkylpiperzinyl, piperazinyl, $C_{1-3}$-alkyl-piperazinyl, and oxazolyl;

more preferably 2,3-dihydro-indol-6-yl, 1,3-benzodioxol-5-yl, 5-indolyl, 4-indolyl, 1,3-dioxo-isoindol-5-yl, 5-indazolyl, 6-indazolyl, 3-pyridyl, 3-quinolyl, 6-quinolyl, isoquinolyl, benzothiazol-6-yl, benzothiazol-5-yl, 1,2,3-benzotriazol-5-yl, 6-benzimidazolyl, and 5-pyridyl;

wherein R⁵ is independently selected from H, $C_{1-10}$-alkyl, $C_{2-10}$-alkenyl, $C_{2-10}$-alkynyl, $C_{3-10}$-cycloalkyl, $C_{4-10}$-cycloalkenyl, R⁴, aryl optionally substituted with 1–3 substituents independently selected from R³, $C_1$–$C_{10}$ alkyl substituted with 1–3 substituents independently selected from aryl, R⁷ and R⁴;

$C_3$–$C_{10}$ cycloalkyl substituted with 1–3 substituents independently selected from aryl, R⁷ and R⁴; and $C_2$–$C_{10}$ alkenyl substituted with 1–3 substituents independently selected from aryl, R⁷ and R⁴;

wherein R⁶ is selected from —C(O)R⁵, —COOR⁵, —C(O)NR⁵R⁵ and —S(O)$_n$R⁵;

wherein R⁷ is independently halo, —CF₃, —SR⁵, —OR⁵, —OC(O)R⁵, —NR⁵R⁵, —NR⁵NR⁶, —NR⁶R⁶, —COOR⁵, —NO₂, —CN, —C(O)R⁵, —OC(O)NR⁵R⁵, —C(O)NR⁵R⁵, —N(R⁵)C(O)R⁵, —N(R⁵)(COOR⁵) and —S(O)$_n$NR⁵R⁵; and wherein n is 1 or 2;

preferably 2;

and pharmaceutically acceptable derivative thereof; provided R² is not 4-amino-2-methylquinol-6-yl when R¹ is 4-amino-2-methylquinol-6-yl and when X is NH; further provided X is not —N(CH₃)— when R¹ is 1-methyl-5-benzimidazolyl and when R² is 3-aminosulfonylphenyl. The invention also relates to compounds of Formula IV

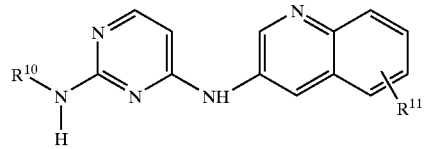

IV wherein R¹⁰ is selected from phenyl, naphthyl, and 5–10 membered heterocyclyl; wherein R¹⁰ is optionally substituted with 1–4 substituents selected from R¹³;

preferably 3,4,5-trimethoxyphenyl, 3,4-dimethoxyphenyl, 3,5-dimethoxyphenyl, 3,4-dimethoxy-6-cyanophenyl, 2,5-dimethoxyphenyl, 2-methoxyphenyl, 3-methoxyphenyl, 4-methoxyphenyl, 3-(dimethylaminoethyl)-4-methoxyphenyl, 4-methoxy-2-nitrophenyl, 2-methoxy-4-nitrophenyl, 3,4-dimethoxy-6-methylphenyl, 4-(3-dimethylamino-propoxy)-phenyl, 4-(1-tert-butoxycarbonyl-piperazin-4-yl)phenyl, 4-(4-piperazinyl)phenyl, 3,5-dimethoxy-4-[2-(4-methyl-piperazin-1-yl)-ethoxy]-phenyl, 3,5-dimethoxy-4-[3-(4-methyl-piperazin-1-yl)-propoxy]-phenyl, 3-methoxy-4-[2-(4-methyl-piperazin-1-yl)-ethoxy]-phenyl, 3-methoxy-4-[3-(4-methyl-piperazin-1-yl)-propoxy]-phenyl, 3,4-dimethoxy-5-[3-(4-methyl-piperazin-1-yl)-propoxy]-phenyl, 3-methoxy-4-(1-methyl-piperidin-4-ylmethoxy)-phenyl, 3-methoxy-4-[2-(1-methyl-piperidin-4-yl)-ethoxy]-phenyl, 3-fluoro-4-(4-methyl-piperazin-1-yl)-phenyl, 3-fluoro-4-(3-piperidin-1-yl-propoxy)-phenyl, 4-(4-isopropyl-piperazin-1-yl)-phenyl, 2-methyl-4-(4-methyl-piperazin-1-yl)-phenyl, 2-fluoro-4,5-dimethoxy-phenyl, 2-methyl-4-[3-(4-methyl-piperazin-1-yl)-propoxy]-phenyl, 2-methyl-4-(3-piperidin-1-ylpropoxy)-phenyl, 3,5-dimethoxy-4-(2-piperidin-1-yl-ethoxy)-phenyl, 3,5-dimethoxy-4-(2-morpholin-4-yl-ethoxy)-phenyl, 4-[2-(4-methyl-piperazin-1-yl)-ethoxy]-phenyl, 3-fluoro-4-[3-(4-methyl-piperazin-1-yl)-propoxy]-phenyl, 3-fluoro-4-[2-(4-methyl-piperazin-1-yl)-ethoxy]-phenyl, 3-fluoro-4-(2-piperidin-1-yl-ethoxy)-phenyl, 4-(1-tert-butoxycarbonyl-piperazin-4-yl)-3-difluoromethoxy-phenyl, 2-ethoxycarbonylbutyl-4,5-dimethoxyphenyl, 2-carboxybutyl-4,5-dimethoxyphenyl, 3-methoxy-4-(2-{4-[4-(quinolin-3-ylamino)-pyrimidin-2-yl]-piperazin-1-yl}-ethoxy)-phenyl, 3-methoxy-4-(2-{1-[4-(quinolin-3-ylamino)-pyrimidin-2-yl]-piperidin-4-yl}-ethoxy)-phenyl, 3,4-diethoxyphenyl, 3-methoxy-4-(pyrrolidin-1-ylcarbonylethenyl)phenyl, 3-methoxy-4-(pyrrolidin-1-ylcarbonylethyl)phenyl, 3-methoxy-4-(pyrrolidin-1-ylpropyl)phenyl, 4-[3-(piperidin-1-yl)propoxy]phenyl, 4-(2-(piperidin-1-yl)ethoxy)phenyl, 6-benzimidazolyl, 4-(methylcarbonylaminosulfonyl)phenyl, 4-(N,N'-di-propylaminosulfonyl)phenyl, 3-butylaminosulfonylphenyl, 3-hydroxypropylaminosulfonylphenyl, 3-[(2-thiazolyl)aminosulfonyl]phenyl, 3-aminosulfonylphenyl, 4-aminosulfonylphenyl, 4-methylsulfonylphenyl, 3-quinolyl, 6-quinolyl, 6-hydroxy-3-quinolyl, indol-4-yl, benzothiazol-6-yl, benzothiazol-5-yl, 1,2,3-benzotriazol-5-yl, 4-(4-morpholinyl)phenyl, 4-(4-methylpiperzin-1-yl)phenyl, 3-methoxy-4-(4-morpholinyl)phenyl, 4-methoxycarbonylphenyl, 3-methoxycarbonylphenyl, 4-(dimethylamino)phenyl, 3-(dimethylamino)phenyl, 4-(dimethylamino)-2-methylphenyl, 3-ethylphenyl, 4-ethylphenyl, 4-nitrophenyl, 4-(methylcarbonylamino)phenyl, 3-(methylcarbonylamino)phenyl, 4-methylcarbonylphenyl, 3-aminocarbonylphenyl, 4-aminocarbonylphenyl, 4-aminocarbonyl-3-methoxyphenyl, 3-fluoro-4-methoxyphenyl, 3-chloro-4-methoxyphenyl, 3-trifluoromethoxyphenyl, 4-trifluoromethoxyphenyl, 3-chloro-4-trifluoromethoxyphenyl, 3,5-ditrifluoromethylphenyl, 3-fluoro-5-trifluoromethylphenyl, 4-fluoro-3-trifluoromethylphenyl, 3-methoxy-5-trifluoromethylphenyl, 3-methoxy-4-pentafluoroethylphenyl, 5-indazolyl, 6-indazolyl, 1-methyl-indazol-5-yl, 3-pyridyl, 6-methoxy-3-pyridyl, 2-(4-morpholinyl)-5-pyridyl, 4-bromo-2-fluorophenyl, 2-fluorophenyl, 3-fluorophenyl, 4-fluorophenyl, 2-bromophenyl, 3-bromophenyl, 4-bromophenyl, 3-chloro-4-fluorophenyl, 3-chlorophenyl, 3,4-dichlorophenyl, 3,5-dichlorophenyl, 4-chlorophenyl, 3-ethynylphenyl, 3-cyanophenyl, 2,2-difluoro-1,3-benzodioxol-5-yl, 1,3-benzodioxol-5-yl, 2-methyl-1,3-dioxo-isoindol-5-yl, 3-(oxazol-5-yl)phenyl, 4-(oxazol-5-yl)phenyl, 3-methoxy-4-(oxazol-5-yl)phenyl, 2-naphthyl, 5-indolyl, 1-acetyl-2,3-dihydro-3,3-dimethylindol-6-yl, and 2,3-dihydro-3,3-dimethylindol-6-yl;

more preferably 3,4,5-trimethoxyphenyl, 3-(dimethylaminoethyl)-4-methoxyphenyl, 3-(1,3-oxazol-5-yl)phenyl, 4-[3-(piperidin-1-yl)propoxy]phenyl, 3-methoxy-4-(pyrrolidin-1-ylpropyl)phenyl, and 3,4-dimethoxy-6-methylphenyl;

wherein $R^{11}$ is one or more substituents selected from H, $C_1$–$C_4$ alkyl, $C_1$–$C_4$ haloalkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, —$OR^{14}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

preferably H, hydroxy, methyl, acetyl, trifluoromethyl, methoxy, phenyl and trifluoromethoxy;

more preferably H, methoxy, and trifluoromethoxy;

wherein $R^{11}$ can be attached in either ring of the quinolyl substituent; preferably at position 6 or 7 of the quinolyl ring;

wherein $R^{12}$ is selected from H, $C_{1-6}$-alkyl, $C_{1-6}$-haloalkyl, $C_1$–$C_3$ alkyl substituted with 1–3 substituents independently selected from optionally substituted phenyl and optionally substituted 5–6 membered heterocyclyl;

wherein optionally substituted phenyl and optionally substituted 5–6 membered heterocyclyl are substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl optionally substituted with one or more substituents selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl; and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;

wherein $R^{13}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; and wherein $R^{14}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable derivatives thereof.

The invention also relates to compounds of Formula V

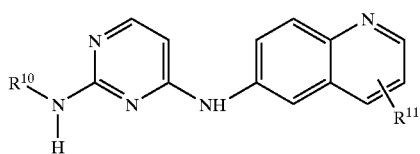

wherein $R^{10}$ is selected from phenyl, naphthyl, and 5–10 membered heterocyclyl; wherein $R^{10}$ is optionally substituted with 1–4 substituents selected from $R^{13}$;

preferably 3,4,5-trimethoxyphenyl, 3,4-dimethoxyphenyl, 3,5-dimethoxyphenyl, 3,4-dimethoxy-6-cyanophenyl, 2,5-dimethoxyphenyl, 2-methoxyphenyl, 3-methoxyphenyl, 4-methoxyphenyl, 3-(dimethylaminoethyl)-4-methoxyphenyl, 4-methoxy-2-nitrophenyl, 2-methoxy-4-nitrophenyl, 3,4-dimethoxy-6-methylphenyl, 4-(3-dimethylamino-propoxy)-phenyl, 4-(1-tert-butoxycarbonyl-piperazin-4-yl)phenyl, 4-(4-piperazinyl)phenyl, 3,5-dimethoxy-4-[2-(4-methyl-piperazin-1-yl)-ethoxy]-phenyl, 3,5-dimethoxy-4-[3-(4-methyl-piperazin-1-yl)-propoxy]-phenyl, 3-methoxy-4-[2-(4-methyl-piperazin-1-yl)-ethoxy]-phenyl, 3-methoxy-4-[3-(4-methyl-piperazin-1-yl)-propoxy]-phenyl, 3,4-dimethoxy-5-[3-(4-methyl-piperazin-1-yl)-propoxy]-phenyl, 3-methoxy-4-(1-methyl-piperidin-4-ylmethoxy)-phenyl, 3-methoxy-4-[2-(1-methyl-piperidin-4-yl)-ethoxy]-phenyl, 3-fluoro-4-(4-methyl-piperazin-1-yl)-phenyl, 3-fluoro-4-(3-piperidin-1-yl-propoxy)-phenyl, 4-(4-isopropyl-piperazin-1-yl)-phenyl, 2-methyl-4-(4-methyl-piperazin-1-yl)-phenyl, 2-fluoro-4,5-dimethoxy-phenyl, 2-methyl-4-[3-(4-methyl-piperazin-1-yl)-propoxy]-phenyl, 2-methyl-4-(3-piperidin-1-yl-propoxy)-phenyl, 3,5-dimethoxy-4-(2-piperidin-1-yl-ethoxy)-phenyl, 3,5-dimethoxy-4-(2-morpholin-4-yl-ethoxy)-phenyl, 4-[2-(4-methyl-piperazin-1-yl)-ethoxy]-phenyl, 3-fluoro-4-[3-(4-methyl-piperazin-1-yl)-propoxy]-phenyl, 3-fluoro-4-[2-(4-methyl-piperazin-1-yl)-ethoxy]-phenyl, 3-fluoro-4-(2-piperidin-1-yl-ethoxy)-phenyl, 4-(1-tert-butoxycarbonyl-piperazin-4-yl)-3-difluoromethoxy-phenyl, 2-ethoxycarbonylbutyl-4,5-dimethoxyphenyl, 2-carboxybutyl-4,5-dimethoxyphenyl, 3-methoxy-4-(2-{4-[4-(quinolin-3-ylamino)-pyrimidin-2-yl]-piperazin-1-yl)-ethoxy)-phenyl, 3-methoxy-4-(2-{1-[4-(quinolin-3-ylamino)-pyrimidin-2-yl]-piperidin-4-yl}-ethoxy)-phenyl, 3,4-diethoxyphenyl, 3-methoxy-4-(pyrrolidin-1-ylcarbonylethenyl)phenyl, 3-methoxy-4-(pyrrolidin-1-ylcarbonylethyl)phenyl, 3-methoxy-4-(pyrrolidin-1-ylpropyl)phenyl, 4-[3-(piperidin-1-yl)propoxy]phenyl, 4-(2-(piperidin-1-yl)ethoxy)phenyl, 6-benzimidazolyl, 4-(methylcarbonylaminosulfonyl)phenyl, 4-(N,N'-di-propylaminosulfonyl)phenyl, 3-butylaminosulfonylphenyl, 3-hydroxypropylaminosulfonylphenyl, 3-[(2-thiazolyl)aminosulfonyl]phenyl, 3-aminosulfonylphenyl, 4-aminosulfonylphenyl, 4-methylsulfonylphenyl, 3-quinolyl, 6-quinolyl, 6-hydroxy-3-quinolyl, indol-4-yl, benzothiazol-6-yl, benzothiazol-5-yl, 1,2,3-benzotriazol-5-yl, 4-(4-morpholinyl)phenyl, 4-(4-methylpiperzin-1-yl)phenyl, 3-methoxy-4-(4-morpholinyl)phenyl, 4-methoxycarbonylphenyl, 3-methoxycarbonylphenyl, 4-(dimethylamino)phenyl, 3-(dimethylamino)phenyl, 4-(dimethylamino)-2-methylphenyl, 3-ethylphenyl, 4-ethylphenyl, 4-nitrophenyl, 4-(methylcarbonylamino)phenyl, 3-(methylcarbonylamino)phenyl, 4-methylcarbonylphenyl, 3-aminocarbonylphenyl, 4-aminocarbonylphenyl, 4-aminocarbonyl-3-methoxyphenyl, 3-fluoro-4-methoxyphenyl, 3-chloro-4-methoxyphenyl, 3-trifluoromethoxyphenyl, 4-trifluoromethoxyphenyl, 3-chloro-4-trifluoromethoxyphenyl, 3,5-ditrifluoromethylphenyl, 3-fluoro-5-trifluoromethylphenyl, 4-fluoro-3-trifluoromethylphenyl, 3-methoxy-5-trifluoromethylphenyl, 3-methoxy-4-pentafluoroethylphenyl, 5-indazolyl, 6-indazolyl, 1-methyl-indazol-5-yl, 3-pyridyl, 6-methoxy-3-pyridyl, 2-(4-morpholinyl)-5-pyridyl, 4-bromo-2-fluorophenyl, 2-fluorophenyl, 3-fluorophenyl, 4-fluorophenyl, 2-bromophenyl, 3-bromophenyl, 4-bromophenyl, 3-chloro-4-fluorophenyl, 3-chlorophenyl, 3,4-dichlorophenyl, 3,5-dichlorophenyl, 4-chlorophenyl, 3-ethynylphenyl, 3-cyanophenyl, 2,2-difluoro-1,3-benzodioxol-5-yl, 1,3-benzodioxol-5-yl, 2-methyl-1,3-dioxo-isoindol-5-yl, 3-(oxazol-5-yl)phenyl, 4-(oxazol-5-yl)phenyl, 3-methoxy-4-(oxazol-5-yl)phenyl, 2-naphthyl, 5-indolyl, 1-acetyl-2,3-dihydro-3,3-dimethylindol-6-yl, and 2,3-dihydro-3,3-dimethylindol-6-yl;

more preferably 3,4,5-trimethoxyphenyl, 3-(dimethylaminoethyl)-4-methoxyphenyl, 3-(1,3-oxazol-5-yl)phenyl, 4-[3-(piperidin-1-yl)propoxy]phenyl, 3-methoxy-4-(pyrrolidin-1-ylpropyl)phenyl, and 3,4-dimethoxy-6-methylphenyl;

wherein $R^{11}$ is one or more substitutents selected from H, $C_1$–$C_4$ alkyl, $C_1$–$C_4$ haloalkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, —$OR^{14}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

preferably H, hydroxy, methyl, acetyl, trifluoromethyl, methoxy, phenyl and trifluoromethoxy;

more preferably H, methoxy, and trifluoromethoxy;

wherein $R^{11}$ can be attached in either ring of the quinolyl substituent; preferably at position 6 or 7 of the quinolyl ring;

wherein $R^{12}$ is selected from H, $C_{1-6}$-alkyl, $C_{1-6}$-haloalkyl, $C_1$–$C_3$ alkyl substituted with 1–3 substituents independently selected from optionally substituted phenyl and optionally substituted 5–6 membered heterocyclyl;

wherein optionally substituted phenyl and optionally substituted 5–6 membered heterocyclyl are substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$- alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl optionally substituted with one or more substituents selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl; and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;

wherein $R^{13}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; and wherein $R^{14}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and pharmaceutically acceptable derivatives thereof;

provided $R^{10}$ is not 4-amino-2-methylquinol-6-yl when $R^{11}$ is 4-amino-2-methyl substitution.

The invention also relates to compounds of Formula VI

VI

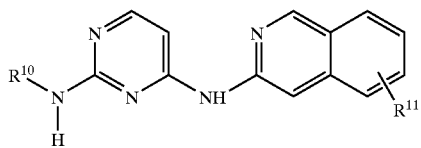

wherein $R^{10}$ is selected from phenyl, naphthyl, and 5–10 membered heterocyclyl; wherein $R^{10}$ is optionally substituted with 1–4 substituents selected from $R^{13}$;

preferably 3,4,5-trimethoxyphenyl, 3,4-dimethoxyphenyl, 3,5-dimethoxyphenyl, 3,4-dimethoxy-6-cyanophenyl, 2,5-dimethoxyphenyl, 2-methoxyphenyl, 3-methoxyphenyl, 4-methoxyphenyl, 3-(dimethylaminoethyl)-4-methoxyphenyl, 4-methoxy-2-nitrophenyl, 2-methoxy-4-nitrophenyl, 3,4-dimethoxy-6-methylphenyl, 4-(3-dimethylamino-propoxy)-phenyl, 4-(1-tert-butoxycarbonyl-piperazin-4-yl)phenyl, 4-(4-piperazinyl)phenyl, 3,5-dimethoxy-4-[2-(4-methyl-piperazin-1-yl)-ethoxy]-phenyl, 3,5-dimethoxy-4-[3-(4-methyl-piperazin-1-yl)-propoxy]-phenyl, 3-methoxy-4-[2-(4-methyl-piperazin-1-yl)-ethoxy]-phenyl, 3-methoxy-4-[3-(4-methyl-piperazin-1-yl)-propoxy]-phenyl, 3,4-dimethoxy-5-[3-(4-methyl-piperazin-1-yl)-propoxy]-phenyl, 3-methoxy-4-(1-methyl-piperidin-4-ylmethoxy)-phenyl, 3-methoxy-4-[2-(1-methyl-piperidin-4-yl)-ethoxy]-phenyl, 3-fluoro-4-(4-methyl-piperazin-1-yl)-phenyl, 3-fluoro-4-(3-piperidin-1-yl-propoxy)-phenyl, 4-(4-isopropyl-piperazin-1-yl)-phenyl, 2-methyl-4-(4-methyl-piperazin-1-yl)-phenyl, 2-fluoro-4,5-dimethoxy-phenyl, 2-methyl-4-[3-(4-methyl-piperazin-1-yl)-propoxy]-phenyl, 2-methyl-4-(3-piperidin-1-yl-propoxy)-phenyl, 3,5-dimethoxy-4-(2-piperidin-1-yl-ethoxy)-phenyl, 3,5-dimethoxy-4-(2-morpholin-4-yl-ethoxy)-phenyl, 4-[2-(4-methyl-piperazin-1-yl)-ethoxy]-phenyl, 3-fluoro-4-[3-(4-methyl-piperazin-1-yl)-propoxy]-phenyl, 3-fluoro-4-[2-(4-methyl-piperazin-1-yl)-ethoxy]-phenyl, 3-fluoro-4-(2-piperidin-1-yl-ethoxy)-phenyl, 4-(1-tert-butoxycarbonyl-piperazin-4-yl)-3-difluoromethoxyphenyl, 2-ethoxycarbonylbutyl-4,5-dimethoxyphenyl, 2-carboxybutyl-4,5-dimethoxyphenyl, 3-methoxy-4-(2-{4-[4-(quinolin-3-ylamino)-pyrimidin-2-yl]-piperazin-1-yl}-ethoxy)-phenyl, 3-methoxy-4-(2-{1-[4-(quinolin-3-ylamino)-pyrimidin-2-yl]-piperidin-4-yl}-ethoxy)-phenyl, 3,4-diethoxyphenyl, 3-methoxy-4-(pyrrolidin-1-ylcarbonylethenyl)phenyl, 3-methoxy-4-(pyrrolidin-1-ylcarbonylethyl)phenyl, 3-methoxy-4-(pyrrolidin-1-ylpropyl)phenyl, 4-[3-(piperidin-1-yl)propoxy]phenyl, 4-(2-(piperidin-1-yl)ethoxy)phenyl, 6-benzimidazolyl, 4-(methylcarbonylaminosulfonyl)phenyl, 4-(N,N'-di-propylaminosulfonyl)phenyl, 3-butylaminosulfonylphenyl, 3-hydroxypropylaminosulfonylphenyl, 3-[(2-thiazolyl)aminosulfonyl]phenyl, 3-aminosulfonylphenyl, 4-aminosulfonylphenyl, 4-methylsulfonylphenyl, 3-quinolyl, 6-quinolyl, 6-hydroxy-3-quinolyl, indol-4-yl, benzothiazol-6-yl, benzothiazol-5-yl, 1,2,3-benzotriazol-5-yl, 4-(4-morpholinyl)phenyl, 4-(4-methylpiperzin-1-yl)phenyl, 3-methoxy-4-(4-morpholinyl)phenyl, 4-methoxycarbonylphenyl, 3-methoxycarbonylphenyl, 4-(dimethylamino)phenyl, 3-(dimethylamino)phenyl, 4-(dimethylamino)-2-methylphenyl, 3-ethylphenyl, 4-ethylphenyl, 4-nitrophenyl, 4-(methylcarbonylamino)phenyl, 3-(methylcarbonylamino)phenyl, 4-methylcarbonylphenyl, 3-aminocarbonylphenyl, 4-aminocarbonylphenyl, 4-aminocarbonyl-3-methoxyphenyl, 3-fluoro-4-methoxyphenyl, 3-chloro-4-methoxyphenyl, 3-trifluoromethoxyphenyl, 4-trifluoromethoxyphenyl, 3-chloro-4-trifluoromethoxyphenyl, 3,5-ditrifluoromethylphenyl, 3-fluoro-5-trifluoromethylphenyl, 4-fluoro-3-trifluoromethylphenyl, 3-methoxy-5-trifluoromethylphenyl, 3-methoxy-4-pentafluoroethylphenyl, 5-indazolyl, 6-indazolyl, 1-methyl-indazol-5-yl, 3-pyridyl, 6-methoxy-3-pyridyl, 2-(4-morpholinyl)-5-pyridyl, 4-bromo-2-fluorophenyl, 2-fluorophenyl, 3-fluorophenyl, 4-fluorophenyl, 2-bromophenyl, 3-bromophenyl, 4-bromophenyl, 3-chloro-4-fluorophenyl, 3-chlorophenyl, 3,4-dichlorophenyl, 3,5-dichlorophenyl, 4-chlorophenyl, 3-ethynylphenyl, 3-cyanophenyl, 2,2-difluoro-1,3-benzodioxol-5-yl, 1,3-benzodioxol-5-yl, 2-methyl-1,3-dioxo-isoindol-5-yl, 3-(oxazol-5-yl)phenyl, 4-(oxazol-5-yl)phenyl, 3-methoxy-4-(oxazol-5-yl)phenyl, 2-naphthyl, 5-indolyl, 1-acetyl-2,3-dihydro-3,3-dimethylindol-6-yl, and 2,3-dihydro-3,3-dimethylindol-6-yl;

more preferably 3,4,5-trimethoxyphenyl, 3-(dimethylaminoethyl)-4-methoxyphenyl, 3-(1,3-oxazol-5-yl)phenyl, 4-[3-(piperidin-1-yl)propoxy]phenyl, 3-methoxy-4-(pyrrolidin-1-ylpropyl)phenyl, and 3,4-dimethoxy-6-methylphenyl;

wherein $R^{11}$ is one or more substitutents selected from H, $C_1$–$C_4$ alkyl, $C_1$–$C_4$ haloalkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, —$OR^{14}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$ —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

preferably H, hydroxy, methyl, acetyl, trifluoromethyl, methoxy, phenyl and trifluoromethoxy;

more preferably H, methoxy, and trifluoromethoxy;

wherein $R^{11}$ can be attached in either ring of the quinolyl substituent; preferably at position 6 or 7 of the quinolyl ring;

wherein $R^{12}$ is selected from H, $C_{1-6}$-alkyl, $C_{1-6}$-haloalkyl, $C_1$–$C_3$ alkyl substituted with 1–3 substituents independently selected from optionally substituted phenyl and optionally substituted 5–6 membered heterocyclyl;

wherein optionally substituted phenyl and optionally substituted 5–6 membered heterocyclyl are substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl optionally substituted with one or more substituents selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl; and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;

wherein $R^{13}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; and wherein $R^{14}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable derivatives thereof.

A family of specific compounds of particular interest within Formula I consists of compounds and pharmaceutically-acceptable salts thereof as follows:

$N^4$-quinolin-3-yl-$N^2$-(3,4,5-trimethoxyphenyl)pyrimidine-2,4-diamine;

$N^4$-quinolin-3-yl-$N^2$-(5-benzimidazolyl)pyrimidine-2,4-diamine;

$N^4$-quinolin-6-yl-$N^2$-(5-benzimidazolyl)pyrimidine-2,4-diamine;

$N^4$-quinolin-3-yl-$N^2$-(5-indazolyl)pyrimidine-2,4-diamine;

$N^4$-quinolin-6-yl-$N^2$-(5-indazolyl)pyrimidine-2,4-diamine;

$N^4$-quinolin-3-yl-$N^2$-(6-indazolyl)pyrimidine-2,4-diamine;

$N^4$-quinolin-6-yl-$N^2$-(6-indazolyl)pyrimidine-2,4-diamine;

$N^4$-quinolin-3-yl-$N^2$-(2,5-dimethoxyphenyl)pyrimidine-2,4-diamine;

$N^4$-quinolin-3-yl-$N^2$-(3,4-dimethoxyphenyl)pyrimidine-2,4-diamine;

$N^4$-quinolin-3-yl-$N^2$-(3-quinolinyl)pyrimidine-2,4-diamine;

$N^4$-quinolin-6-yl-$N^2$-(3-quinolinyl)pyrimidine-2,4-diamine;

$N^4$-quinolin-3-yl-$N^2$-(6-quinolinyl)pyrimidine-2,4-diamine;

$N^4$-quinolin-6-yl-$N^2$-(6-quinolinyl)pyrimidine-2,4-diamine;

$N^4$-quinolin-6-yl-$N^2$-(3,4,5-trimethoxyphenyl)-pyrimidine-2,4-diamine;

$N^2$-(3-aminosulfonylphenyl)-$N^4$-quinolin-6-yl-pyrimidine-2,4-diamine;

$N^2$-(3-aminosulfonylphenyl)-$N^4$-quinolin-3-yl-pyrimidine-2,4-diamine;

$N^2$-(4-aminosulfonylphenyl)-$N^4$-quinolin-6-yl-pyrimidine-2,4-diamine;

$N^2$-(4-aminosulfonylphenyl)-$N^4$-quinolin-3-yl-pyrimidine-2,4-diamine;

$N^2$-(3,4-dimethoxy-6-methylphenyl)-$N^4$-quinolin-6-yl-pyrimidine-2,4-diamine; and $N^2$-(3,4-dimethoxy-6-methylphenyl)-$N^4$-quinolin-3-yl-pyrimidine-2,4-diamine.

A family of specific compounds of particular interest within Formula I' consists of compounds and pharmaceutically-acceptable salts thereof as follows:

$N^4$-Quinolin-3-yl-$N^2$-(3,4,5-trimethoxyphenyl)pyrimidine-2,4-diamine;

$N^4$-quinolin-6-yl-$N^2$-(3,4,5-trimethoxyphenyl)-pyrimidine-2,4-diamine;

$N^2$-(3,4-dimethoxy-6-methylphenyl)-$N^4$-quinolin-3-yl-pyrimidine-2,4-diamine;

N²-(6-(4-morpholinyl)-3-pyridinyl)-N⁴-(3-quinolinyl)-2,4-pyrimidinediamine;
N²-(4-bromo-2-fluorophenyl)-N⁴-(3-quinolinyl)-2,4-pyrimidinediamine;
N²-(4-bromophenyl)-N⁴-(3-quinolinyl)-2,4-pyrimidinediamine;
N²-(4-(4-methyl-1-piperazinyl)phenyl)-N⁴-(3-quinolinyl)-2,4-pyrimidinediamine;
N⁴-(3-Isoquinolinyl)-N²-(3,4,5-tris(methoxy)phenyl)-2,4-pyrimidinediamine;
N⁴-(3-Isoquinolinyl)-N²-(2-methyl-4,5-bis(methoxy)phenyl)-2,4-pyrimidinediamine;
2-(Methoxy)-4-((4-(3-quinolinylamino)-2-pyrimidinyl)amino)benzamide;
N²-[4-(3-Piperidin-1-yl-propoxy)-phenyl]-N⁴-quinolin-3-yl-pyrimidine-2,4-diamine;
N²-(4-((2-(1-Piperidinyl)ethyl)oxy)phenyl)-N⁴-(3-quinolinyl)-2,4-pyrimidinediamine;
N²-(3-(2-(Dimethylamino)ethyl)-4-(methoxy)phenyl)-N⁴-(3-quinolinyl)-2,4-pyrimidinediamine;
N²-(3-(1,3-oxazol-5-yl)phenyl)-N⁴-(3-quinolinyl)-2,4-pyrimidinediamine;
N²-(3-(1,3-oxazol-5-yl)phenyl)-N⁴-(6-quinolinyl)-2,4-pyrimidinediamine;
N²-(3-(methoxy)-4-(1,3-oxazol-5-yl)phenyl)-N⁴-(3-quinolinyl)-2,4-pyrimidinediamine;
N²-(1-acetyl-3,3-dimethyl-2,3-dihydro-1H-indol-6-yl)-N⁴-(3-quinolinyl)-2,4-pyrimidinediamine;
N⁴-(2-Methyl-6-quinolinyl)-N²-(3,4,5-tris(methoxy)phenyl)-2,4-pyrimidinediamine;
N⁴-(1-Methoxy-isoquinolin-3-yl)-N-2-(3,4,5-trimethoxy-phenyl)-pyrimidine-2,4-diamine;
N²-[3-Methoxy-4-(2-{4-[4-(quinolin-3-ylamino)-pyrimidin-2-yl]-piperazin-1-yl}-ethoxy)-phenyl]-N-quinolin-3-yl-pyrimidine-2,4-diamine;
N²-(3-Methoxy-4-morpholin-4-yl-phenyl)-N⁴-quinolin-3-yl-pyrimidine-2,4-diamine;
N²-(3,4,5-Trimethoxyphenyl)-N⁴-(6-methoxy-quinolin-3-yl)-2,4-pyrimidinediamine;
N²-(2-Methyl-4,5-dimethoxyphenyl)-N⁴-(6-methoxy-quinolin-3-yl)-2,4-pyrimidinediamine;
N²-(3,4,5-Trimethoxyphenyl)-N⁴-(6-trifluoromethoxy-quinolin-3-yl)-2,4-pyrimidinediamine;
N²-(2-Methyl-4,5-dimethoxyphenyl)-N⁴-(6-trifluoromethoxy-quinolin-3-yl)-2,4-pyrimidinediamine;
3-(2-Methoxy-4-[4-(quinolin-3-ylamino)-pyrimidin-2-ylamino]-phenyl}-1-pyrrolidin-1-yl-propenone;
3-{2-Methoxy-4-[4-(quinolin-3-ylamino)-pyrimidin-2-ylamino]-phenyl}-1-pyrrolidin-1-yl-propanone;
N²-[3-Methoxy-4-(3-pyrrolidin-1-yl-propyl)-phenyl]-N⁴-quinolin-3-yl-pyrimidine-2,4-diamine; and
N²-[3-Methoxy-4-(2-{1-[4-(quinolin-3-ylamino)-pyrimidin-2-yl]-piperidin-4-yl}-ethoxy)-phenyl]-N⁴-quinolin-3-yl-pyrimidine-2,4-diamine.

Indications

Compounds of the present invention would be useful for, but not limited to, the prevention or treatment of cancer and related diseases. The compounds of the invention have kinase inhibitory activity, such as IGF-1R inhibitory activity. The compounds of the invention are useful in therapy as antineoplasia agents.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful for promoting apoptosis.

The compounds of this invention may also act as inhibitors of other protein kinases, e.g. ErbB, KDR, CDK-2, LCK, CDK-5, IKK, JNK3, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats. As used herein, the compounds of the present invention include the pharmaceutically acceptable derivatives thereof.

Definitions

The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to treat neoplasia.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The terms "ring" and "ring system" refer to a ring comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

Leaving groups are species that may be detached from a molecule during a reaction and are known in the art. Examples of such groups include, but are not limited to, halogen groups (e.g., I, Br, F, Cl), sulfonate groups (e.g., mesylate, tosylate), sulfide groups (e.g., $SCH_3$), and the like. Nucleophiles are species that may be attached to a molecule during reaction and are known in the art. Examples of such groups include, but are not limited to, amines, Grignard reagents, anionic species (e.g., alkoxides, amides, carbanions) and the like.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 5 substituents such as lower alkyl, hydroxyl, halo, lower haloalkyl, nitro, cyano, lower alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The term "alkylsulfonyl" embraces sulfonyl radicals substituted with an alkyl radical. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, and ethylsulfonyl.

The terms "sulfamyl," "aminosulfonyl" and "sulfonamidyl," denotes a sulfonyl radical substituted with an amine radical, (—$SO_2NH_2$).

The terms "carboxy" or "carboxyl", whether used alone or with other terms, such as "carboxyalkyl", denotes —$CO_2H$.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "heterocyclylalkylenyl" embraces heterocyclyl-substituted alkyl radicals. Preferable heterocyclyl alkylenyl radicals are "Lower heterocyclylalkylenyl" radicals having heterocyclyl radicals attached to alkyl radicals having one to six carbon atoms. More preferred are heterocyclyl-$C_1$–$C_2$-alkylenyl radicals such as morpholinylmethyl, methylpiperdinylmethyl, methylpiperazinylmethyl, and the like.

The term "carbonyl", whether used alone or with other terms, such as "aminocarbonyl", denotes —(C=O)—.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl, such as N-methylaminomethyl, N,N-dimethylaminoethyl, N,N-diethylaminomethyl and the like.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above. The aryl portion may be further substituted.

The term "heteroaryloxy" embraces optionally substituted heteroaryl radicals, as defined above, attached to an oxygen atom.

The term "heteroarylalkoxy" embraces heteroarylalkyl radicals attached through an oxygen atom. More preferred heteroarylalkoxy radicals are "lower heteroarylalkoxy" radicals having optionally substituted heteroarylalkyl radicals attached to lower alkoxy radical as described above.

The term "aminocarbonyl" denotes an amide group of the formula —C(=O)$NH_2$.

The term "alkoxycarbonyl" denotes an ester group, where a carbonyl radical is substituted with an alkoxy radical. More preferred are "lower alkoxycarbonyl" having lower alkoxy radicals as described above attached to a carbonyl radical.

The term "alkylcarbonyl" denotes carbonyl groups which have been substituted with an alkyl radical. More preferred are $C_1$–$C_6$-alkylcarbonyl radicals, such as methylcarbonyl, ethylcarbonyl and propylcarbonyl.

The terms "N-alkylaminocarbonyl" and "N,N-dialkylaminocarbonyl" denote aminocarbonyl radicals substituted with one or two alkyl radicals, respectively. More preferred are "lower alkylaminocarbonyl" having lower alkyl radicals as described above attached to an aminocarbonyl radical.

A "pharmaceutically acceptable prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulas described herein.

The term "comprising" is meant to be open ended, including the indicated component but not excluding other elements.

The phrase "Formula I–VI" includes subformulas such as I'.

The present invention preferably includes compounds that selectively inhibit IGF-1R.

The present invention also comprises the use of a compound of the invention, or pharmaceutically acceptable derivative thereof, in the manufacture of a medicament for the treatment either acutely or chronically of an apoptosis mediated disease state, including those described previously. The compounds of the present invention are useful in the manufacture of an anti-cancer medicament. The compounds of the present invention are also useful in the manufacture of a medicament to attenuate or prevent disorders through inhibition of IGF-1R.

The present invention comprises a pharmaceutical composition comprising a therapeutically-effective amount of a compound of Formulas I–VI in association with a least one pharmaceutically-acceptable carrier, adjuvant or diluent.

The present invention also comprises a method of treating apoptosis related disorders, in a subject, the method comprising treating the subject having or susceptible to such disorder with a therapeutically-effective amount of a compound of the present invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert $C_{1-921}$, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), EGFR inhibitors such as Iressa, KDR inhibitors, COX-2 inhibitors including celecoxib, rofecoxib, parecoxib, valdecoxib, and etoricoxib, NSAID's, SOD mimics or $\alpha_v\beta_3$ inhibitors.

The present invention comprises a process for the preparation of a compound of Formula I–VI.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Compounds of the present invention can possess, in general, tautomeric forms, which are included in the family of compounds in Formula I–VI.

Also included in the family of compounds of Formula I–VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–VI may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, gluconic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane proprionic, pantothenic, toluenesulfonic, salicylic, sulfanilic, stearic, succinic, tartaric, thiocyanic, and undecanoic.

Suitable pharmaceutically-acceptable base addition salts of compounds of Formula I–VI include metallic salts, such as salts made from alkali metals and alkaline earth metals including, for example, aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, ammonia, triethylamine, trimethylamine. All of these salts may be prepared by conventional means from the corresponding compound of the invention by reacting, for example, the appropriate acid or base with the compound of Formula I–VI.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977).

Combinations of substituents and variables envisioned by this invention are only those that result in the formation of stable compounds. The term "stable", as used herein, refers to compounds which possess stability sufficient to allow preparation.

As used herein, the compounds of this invention, including the compounds described herein, are defined to include pharmaceutically acceptable derivatives or prodrugs thereof.

Pharmaceutically acceptable salts of the compounds of this invention include those derived from pharmaceutically acceptable inorganic and organic acids and bases. Other acids, such as oxalic, while not in themselves pharmaceutically acceptable, may be employed in the preparation of salts useful as intermediates in obtaining the compounds of the invention and their pharmaceutically acceptable acid addition salts. This invention also envisions the quaternization of any basic nitrogen-containing groups of the compounds disclosed herein. Water or oil-soluble or dispersible products may be obtained by such quaternization.

The invention relates to a process for making a compound of any of the formulas described herein, comprising reacting a pyrimidine of one or more of the formulas:

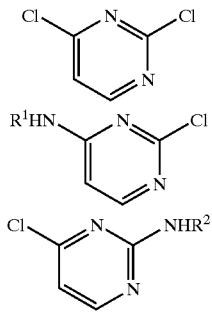

with an appropriate nucleophilic agent or agents, wherein the groups in said formulas are as defined herein.

The invention also relates to a process for making a compound of any of the formulas described herein, comprising reacting a pyrimidine of one or more of the formulas:

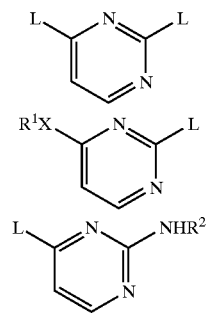

with an appropriate nucleophilic agent or agents, wherein L is defined as a leaving group and the groups in said formulas are as defined herein.

General Synthetic Procedures

The compounds of the invention can be synthesized according to the following procedures of Schemes 1–8, wherein the substituents are as defined for Formulas I–VI, above, except where further noted.

Scheme 1

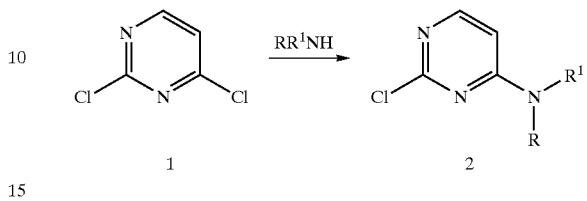

Monoamine substituted pyrimidines 2 can be prepared according to the method set out in Scheme 1. 2,4-Dichloropyrimidine 1 is coupled with heteroarylamines, in the presence of base, such as NaH, and a solvent, such as DMF or THF, at a temperature of about 0° C. to about RT to give (2-chloro-pyrimidin-4-yl)amine 2.

Alternatively, 2,4-dichloropyrimidine 1 is coupled with an amine in the presence of NaOt-Bu, in a solvent, such as t-BuOH, at a temperature about RT to yield monoamine-substituted pyrimidines 2.

Scheme 2

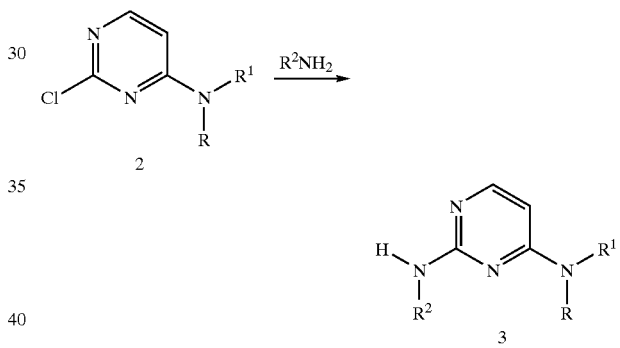

Monoamine substituted pyrimidines 2 are reacted with an amine having an active hydrogen, such as $R^2NH_2$, in solvent, such as acetone and water, and in the presence of acid, such as conc. HCl, to give the diamine substituted pyrimidine 3.

Alternatively, the reaction can be performed in a solvent such as IPA or DMSO, with or without DIEA or in a solvent such as IPA or DMSO with or without Et$_3$N.TFA, or in a solvent such as HOAc.

Preferably the reaction is heated, more preferably at a temperature of about >50° C., even more preferably at a temperature of about 90–100° C.

Scheme 3

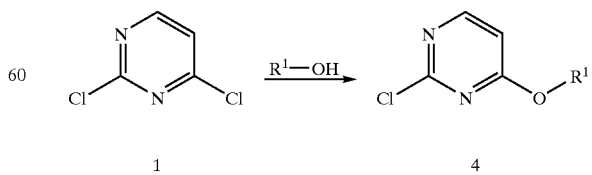

Heteroaryloxy substituted pyrimidines 2 can be prepared according to the method set out in Scheme 3. 2,4-

Dichloropyrimidine 1 is coupled with heteroaryl alcohols, in the presence of base, such as Na$_2$CO$_3$, and a solvent, such as EtOH, at a temperature of about 0° C. to about RT to give 2-chloropyrimidin-4-yl ether 4.

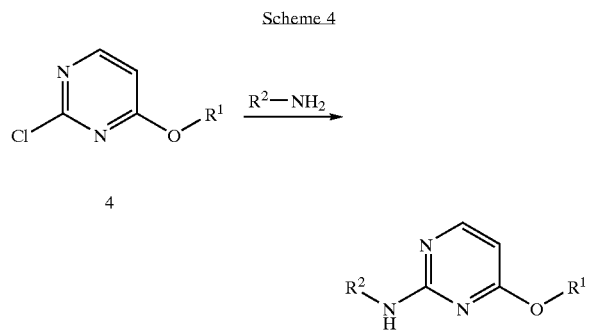

Ether substituted pyrimidines 4 are reacted with an amine having an active hydrogen such as R$^2$NH$_2$, in a solvent such as DMSO, to give the amine/ether substituted pyrimidine 5.

Preferably the reaction is heated, more preferably at a temperature of about >50° C., even more preferably at a temperature of about 90–100° C.

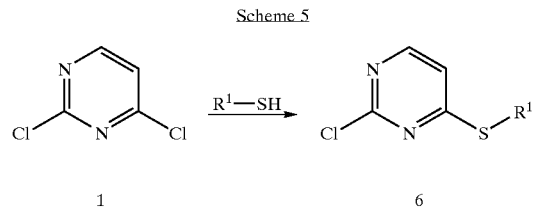

Heteroarylthio substituted pyrimidines 6 can be prepared according to the method set out in Scheme 5. 2,4-Dichloropyrimidine 1 is coupled with heteroaryl thiols, in the presence of base, such as Na$_2$CO$_3$, and a solvent, such as EtOH, at a temperature of about 0° C. to about RT to give 2-chloro-pyrimidin-4-yl thioether 6.

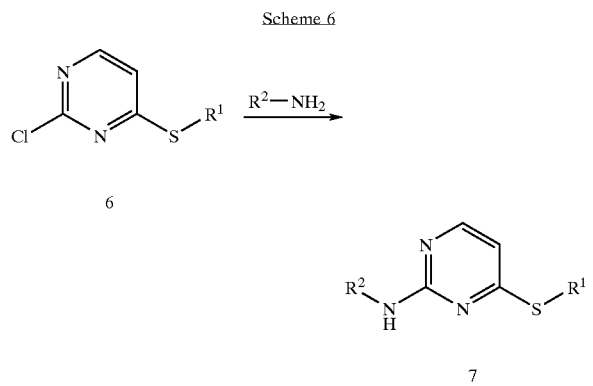

Thioether substituted pyrimidines 6 are reacted with an amine having an active hydrogen such as R$^2$NH$_2$, in a solvent such as DMSO, to give the amine/thioether substituted pyrimidine 7.

Preferably the reaction is heated, more preferably at a temperature of about >50° C., even more preferably at a temperature of about 90–100° C.

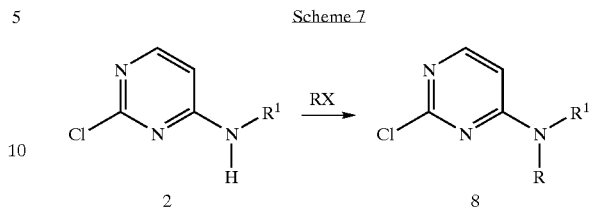

Tertiary-amine substituted pyrimidines 8 can be prepared reacted with alkyl halides, in the presence of base, such as NaH, and a solvent, such as DMF, at a temperature of about 0° C. to about RT to give (2-chloro-pyrimidin-4-yl)amine 8.

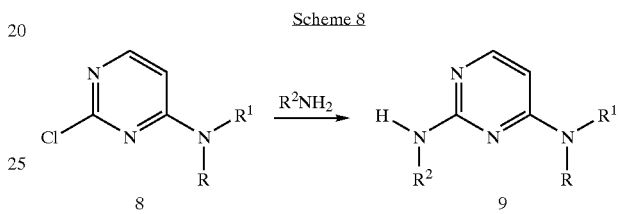

Monoamine substituted pyrimidines 8 are reacted with a heterocyclic group having an active hydrogen such as R$^2$NH$_2$, such as in solvent, such as acetone and water, and in the presence of acid, such as conc. HCl, to give the diamine substituted pyrimidine 9.

Alternatively, the reaction can be performed in a solvent such as IPA or DMSO, with or without DIEA or in a solvent such as IPA or DMSO with or without Et$_3$N.TFA, or in a solvent such as HOAc.

Preferably the reaction is heated, more preferably at a temperature of about >50° C., even more preferably at a temperature of about 90–100° C.

If one or more other functional groups, for example carboxy, hydroxy, amino, or mercapto, are or need to be protected in a compound of Formulas I–VI, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g. EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH, IPA or 1-propanol, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. AcOH, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I–VI, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I–VI. These detailed descriptions fall within the scope, and serve to exemplify, the above described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

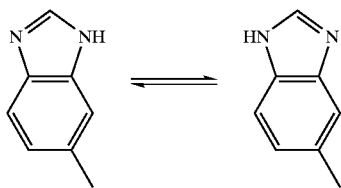

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

Analytical Methods:

Unless otherwise indicated all HPLC analyses were run on an HP-1000 or HP-1050 system with an HP Zorbax SB-$C_{18}$ (5μ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush. The peaks of interest eluted on the LC profiles at the times indicated.

LC-MS Methods:

Method A:

1. Samples were run on an HP-1100 system with an HP Zorbax SB-$C_8$ (5μ) reverse-phase column (4.6×50 mm) run at 30° C. with a flow rate of 0.75 mL/min.
2. The mobile phase used solvent A ($H_2O$/0.1% AcOH) and solvent B ($CH_3CN$/0.1% AcOH) with a 10 min gradient from 10% to 90% $CH_3CN$. The gradient was followed by a 1 min return to 10% $CH_3CN$ and a 2 min flush.
3. The peaks of interest eluted on the LC profiles at the times indicated.

Method B:

1. Samples were run on an HP-1100 system with an HP Zorbax SB-$C_8$ (5μ) reverse-phase column (4.6×50 mm) run at 30° C. with a flow rate of 1.5 mL/min.
2. The mobile phase used solvent A ($H_2O$/0.1% AcOH) and solvent B ($CH_3CN$/0.1% AcOH) with a 5 min gradient from 10% to 90% $CH_3CN$. The gradient was followed by a 0.5 min return to 10% $CH_3CN$ and a 1.5 min flush.

Preparative HPLC: Where indicated compounds of interest were purified via preparative HPLC using a Gilson workstation with a 30×100 mm column at 30 mL/min. The mobile phase used solvent A ($H_2O$/0.1% TFA) and solvent B ($CH_3CN$/0.1% TFA) with a 15 min gradient from 5% to 100% $CH_3CN$. The gradient was followed by a 2 min return to 5% $CH_3CN$.

Proton NMR Spectra:

Unless otherwise indicated all $^1H$ NMR spectra were run on an Varian series Mercury 300 or 400 MHz instrument. All observed protons are reported as parts per million (ppm) downfield from tetramethylsilane (TMS) or other internal reference in the appropriate solvent indicated.

The following abbreviations are used:

| | |
|---|---|
| AcOH | acetic acid |
| $CH_3CN$ | acetonitrile |
| ATP | adenosine triphosphate |
| $NH_4Cl$ | aminonium chloride |
| $NH_4OH$ | ammonium hydroxide |
| BINAP | 2,2'-bis (diphenylphosphino)-1,1'binaphthyl |
| $BH_3$ | borane |

-continued

| | |
|---|---|
| BSA | bovine serum albumin |
| DDQ | 2,3-dichloro-5,6-dicyano-1,4-benzoquinone |
| $CH_2Cl_2$ | dichloromethane |
| DIEA | diisopropylethylamine |
| DIAD | diisopropyl azodicarboxylate |
| EDC | 1-(3-dimethylaminopropyl)-3-ethylcarbodiimide hydrochloride |
| DMF | dimethylformamide |
| DMSO | dimethyl sulfoxide |
| DPPA | diphenylphosporyl azide |
| DTT | dithiothreitol |
| EtOH | ethanol |
| EtOAc | ethyl acetate |
| $Et_2O$ | ethyl ether |
| $FeSO_4$ | ferric sulfate |
| g | gram |
| h | hour |
| HBr | hydrobromic acid |
| HCl | hydrochloric acid |
| $H_2$ | hydrogen |
| HOBt | hydroxybenzotriazole |
| IPA | isopropanol |
| LAH | lithium aluminum hydride |
| LiOH | lithium hydroxide |
| $MgSO_4$ | magnesium sulfate |
| $MnCl_2$ | manganese chloride |
| MeOH | methanol |
| MeI | methyl iodide |
| mg | milligram |
| mL | milliliter |
| $\mu l$ | microliter |
| min | minutes |
| $N_2$ | nitrogen |
| Pd/C | palladium on carbon |
| $Pd(OAc)_2$ | palladium acetate |
| $Pd(PPh_3)_4$ | palladium tetrakis triphenylphosphine |
| $Pd_2(dba)_3$ | tris (dibenzylideneacetone) di-palladium |
| $POCl_3$ | phosphoryl chloride |
| $PCl_5$ | phosphorous pentachloride |
| $P_2O_5$ | phosphorous pentoxide |
| Pt/C | platinum on carbon |
| $K_2CO_3$ | potassium carbonate |
| KOH | potassium hydroxide |
| KOt-Bu | potassium t-butoxide |
| RT | Room temperature |
| $NaHCO_3$ | sodium bicarbonate |
| $Na_2CO_3$ | sodium carbonate |
| NaCl | sodium chloride |
| NaCN | sodium cyanide |
| $NaCNBH_3$ | sodium cyanoborohydride |
| NaH | sodium hydride |
| NaOH | sodium hydroxide |
| NaI | sodium iodide |
| $Na_2SO_4$ | sodium sulfate |
| NaOt-Bu | sodium t-butoxide |
| t-BuOH | tert-butyl alcohol |
| t-BuOMe, MTBE | tert-butylmethylether |
| Boc | tert-butyloxycarbonyl |
| THF | tetrahydrofuran |
| TEA, $Et_3N$ | triethylamine |
| TFA | trifluoroacetic acid |
| $PPh_3$ | triphenyl phosphine |
| $H_2O$ | water |

Preparation A—(2-chloropyrimidin-4-yl)-quinolin-3-yl-amine

A mixture of 2,4-dichloropyrimidine (1.0 g, 6.7 mmol), 3-aminoquinoline (1.1 g, 7.79 mmol) and DIEA (2.0 mL, 11.5 mmol) in IPA (8 mL) was heated to reflux for 48 h. The mixture was poured into EtOAc (200 mL) and washed with $H_2O$ (100 mL). The organics were dried over anhydrous $Na_2SO_4$ and concentrated under reduced pressure. The crude was purified via medium pressure liquid chromatography using 50:50 EtOAc/hexanes followed by 100% EtOAc followed by 5:95 MeOH/$CH_2Cl_2$ followed by 1.0:10:90 conc. $NH_4OH/MeOH/CH_2Cl_2$ as the solvent system. (2-Chloropyrimidin-4-yl)-quinolin-3-yl-amine was obtained as a tan solid.

The following compounds were prepared from the corresponding amine in a manner similar to that described above:
(2-Chloropyrimidin-4-yl)-isoquinolin-3-yl-amine;
(3H-Benzimidazol-5-yl)-(2-chloro-pyrimidin-4-yl)-amine;
(2-Chloropyrimidin-4-yl)-quinolin-6-yl-amine (M+H—257);
1-[6-(2-Chloro-pyrimidin-4-ylamino)-3,3-dimethyl-2,3-dihydro-indol-1-yl]-ethanone [M+H—317];
(2-Chloro-pyrimidin-4-yl)-quinoxalin-6-yl-amine [M+H—258];
(2-Chloro-pyrimidin-4-yl)-(2-phenyl-quinolin-3-yl)-amine [M+H—333];
(2-Chloro-pyrimidin-4-yl)-(2-methyl-quinolin-6-yl)-amine [M+H—271];

Preparation B—2-Methoxy-4-nitrobenzamide

To a mixture of 2-methoxy-4-nitrobenzoic acid (2.0 g, 10.1 mmol) in $CH_2Cl_2$ (100 mL) was added oxalylchloride (2.7 mL, 31.1 mmol) followed by the addition of 1 mL DMF over 1 h. The organics were concentrated under reduced pressure and the residue dissolved in $CH_2Cl_2$ (50 mL). The organics were concentrated under reduced pressure and placed under vacuum. The residue dissolved into $CH_2Cl_2$ (40 mL) and cooled to 0° C. Ammonia gas was bubbled into the solution for approximately 10 min. The organics were concentrated under reduced pressure and the crude was purified via medium pressure liquid chromatography using $CH_2Cl_2$ followed by 3:97 MeOH/$CH_2Cl_2$ as the solvent system. The desired compound was obtained as an off-white solid.

Preparation C—4-Amino-2-methoxybenzamide

A mixture of 2-methoxy-4-nitrobenzamide (1.25 g, 6.37 mmol) and 5% Pd/C (200 mg) in 50 mL of EtOH was placed under a balloon of $H_2$. The mixture was stirred for 48 h. The catalyst was removed by suction filtration and the organics were concentrated to give the desired amine as a yellowish oil.

Preparation D—3H-Benzimidazol-5-ylamine

A mixture of 5-nitrobenzimidazole (10 g, 61.3 mmol) and 5% Pd/C (2.5 g) in 250 mL of EtOH was placed under a balloon of $H_2$. The mixture was stirred for 18 h. The catalyst was removed by suction filtration and the organics were concentrated to give the desired amine as a yellowish oil.

Preparation E—1-(3-Chloropropyl)-piperidine

A mixture of 1-bromo-3-chloropropane (65.6 g, 0.417 mol), piperidine (62 mL, 0.625 mol) in anhydrous THF (200 mL) was heated to reflux for 24 h. The mixture was cooled to RT and filtered to remove the solids formed. The organics were concentrated under reduced pressure. The residue was taken up in 2N HCl and washed twice with EtOAc (200 mL). The aqueous layer was made basic under EtOAc with 2N NaOH until pH 14. The compound was extracted into EtOAc (2×1L) and the combined organics dried over anhydrous $MgSO_4$ then concentrated under reduced pressure to give the desired compound as a yellowish oil.

Preparation F—1-[3-(4-nitro-phenoxy)-propyl]-piperidine

In a three-neck flask with an overhead mechanical stirrer, a mixture of 1-(3-chloropropyl)-piperidine (49.8 g, 0.308 mol), 4-nitrophenol (42.8 g, 0.308 mol) and $K_2CO_3$ (212 g, 1.53 mol), in anhydrous DMF (200 mL) was heated to 94° C. and stirred for 18 h. The mixture was cooled to RT then diluted with 2 L water. The organics were taken up in EtOAc (2 L) and washed twice with 2N NaOH (500 mL) then brine (200 mL). The combined organics were dried over anhydrous $MgSO_4$ then concentrated under reduced pressure to give 1-[3-(4-nitro-phenoxy)-propyl]-piperidine as a yellowish oil.

Preparation G—4-(3-Piperidin-1-yl-propoxy)-phenylamine

A mixture of 1-[3-(4-nitro-phenoxy)-propyl]-piperidine (15.5 g, 58.6 mmol) and 10% Pd/C (12.5 g) in 150 mL of EtOH was placed under a balloon of $H_2$. The mixture was stirred for 18 h. The catalyst was removed by suction filtration and the organics concentrated to give 4-(3-piperidin-1-yl-propoxy)-phenylamine as a yellowish oil.

Preparation H—3-Methoxy-4-oxazol-5-yl-phenylamine

3-Methoxy-4-oxazol-5-yl-phenylamine was prepared as described in U.S. Pat. No. 5,932,600.

Preparation I—N-(2-Bromo-5-nitrophenyl)-acetamide

2-Bromo-5-nitroaniline (42.54 g, 196 mmol) was dissolved into glacial AcOH (1.3 L) under air at RT. $Ac_2O$ was added, and the reaction was stirred at RT overnight, giving a white precipitate. The reaction was diluted with water (6 L). The precipitate formed was collected by vacuum filtration, washed with water, then placed under high vacuum to dry, giving the desired product as an off-white solid.

Preparation J—N-(2-Bromo-5-nitrophenyl)-N-(2-methylallyl)-acetamide

A suspension of NaH (14.1 g, 352.5 mmol, 60% dispersion in mineral oil) in DMF (400 mL) under $N_2$ was cooled to −65° C. N-(2-Bromo-5-nitrophenyl)-acetamide (30.44 g, 117.5 mmol) was dissolved into DMF (400 mL), then added to the NaH suspension, portionwise, via syringe, over 90 min, resulting in an opaque red color. This mixture was stirred for 45 min, then warmed to 0° C. 3-Bromo-2-methylpropene (23.7 mL, 2.35 mmol) was added as a solution in DMF (100 mL) via a pressure equalizing dropping funnel over 30 min, which caused the mixture to turn black. The mixture was stirred overnight with gradual warming to RT. The reaction was quenched upon pouring into ice water (~1 L). The mixture was extracted with EtOAc (3×750 mL). The combined EtOAc extracts were washed with saturated $NaHCO_3$, brine, dried over $Na_2SO_4$, filtered, then concentrated under reduced pressure giving a black oil. This oil was eluted through a 38×7 cm column of silica gel with a 5%, 10%, 15%, 20%, 25%, 30%, and 35% EtOAc:Hexane step gradient (1 L each step) giving a dark brown waxy solid.

Preparation K—1-(3,3-Dimethyl-6-nitro-2,3-dihydro-indol-1-yl)-ethanone

N-(2-Bromo-5-nitrophenyl)-N-(2-methyl-allyl)-acetamide (10.1 g, 39.0 mmol), sodium formate (3.18 g, 46.8 mmol), sodium acetate (8.0 g, 97.5 mmol.), and tetraethylammonium chloride hydrate (6.79 g, 41.0 mmol,) were combined and treated with DMF (100 mL) under air at RT. The mixture was immediately degassed under vacuum with stirring for 20 min. $Pd(OAc)_2$ (0.94 g, 4.2 mmol) was then added. The mixture was placed under argon and stirred at 80° C. overnight. The mixture was concentrated under reduced pressure and treated with a saturated $NaHCO_3$ solution. This mixture was extracted 3× with EtOAc (300 mL). The EtOAc extracts were washed with water and brine, combined, dried over $Na_2SO_4$, filtered, and concentrated under reduced pressure giving the desired compound as a brown solid.

Preparation L—1-(6-Amino-3,3-Dimethyl-2,3-dihydro-indol-1-yl)-ethanone 1-(3,3-Dimethyl-6-nitro-2,3-dihydro-indol-1-yl)-ethanone (7.64 g, 32.8 mmol) was dissolved in EtOH (500 mL) under $N_2$ at RT. The solution was degassed under vacuum with stirring. A catalytic amount of 10% Pd/C was added, the reaction vessel was charged with a $H_2$ atmosphere (balloon pressure), and the mixture was stirred vigorously overnight at RT. The reaction was quenched by filtering through Celite® with MeOH. The filtrate was concentrated under reduced pressure, then dried under high vacuum to give the desired compound as a dark brown solid.

Preparation M—6-Nitroquinoxaline

A mixture of 4-nitro-1,2-phenylenediamine (4.0 g, 26.1 mmol) and glyoxal (6 mL, 40% solution in water) in $CH_3CN$ (200 mL) was stirred at 50° C. for 18 h. The mixture was diluted with 250 mL water and the organics extracted twice with 200 mL EtOAc. The combined organics were dried over anhydrous $MgSO_4$ and the organics were concentrated under reduced pressure. The crude was purified via medium pressure liquid chromatography using $CH_2Cl_2$ followed by 2:98 MeOH/$CH_2Cl_2$ followed 5:95 MeOH/$CH_2Cl_2$ as the solvent system. The desired compound was obtained as a tan solid.

Preparation N—6-Aminoquinoxaline

A mixture of 6-nitroquinoxaline (1.5 g, 8.56 mmol), iron metal (2.86 g, 51.2 mmol), iron sulfate heptahydrate (4.08 g, 17.1 mmol) and 2 g Celite in water (50 mL) was heated to reflux for 3.5 h. The mixture was made basic with 2 N NaOH and EtOAc was added (100 mL). After stirring, the mixture was filtered through a pad of Celite, followed by washing with EtOAc (50 mL). The combined organics were separated dried over anhydrous $Na_2SO_4$ and the organics were concentrated under reduced pressure. The material was used without any additional purification.

Preparation O—3-Nitro-2-phenyl-quinoline

A mixture of benzoylnitromethane (700 mg, 4.23 mmol) and 2-aminobenzaldehyde (500 mg, 4.13 mmol) in water (25 mL) was heated to 100° C. for 3 h. The mixture was poured into EtOAc (1500 mL) and washed with brine (50 mL). The organics were dried over anhydrous $MgSO_4$ and the organics were concentrated under reduced pressure. The desired product was obtained as an off white solid.

Preparation P—2-Phenyl-quinolin-3-ylamine

A mixture of 3-nitro-2-phenyl-quinoline (0.9 g, 3.6 mmol) and 10% Pd/C (200 mg) in 10 mL of EtOH was placed under a balloon atmosphere of $H_2$ and stirred for 18 h. The catalyst was removed by suction filtration and the organics were concentrated to give the desired compound as a yellowish oil.

Preparation Q—6-(2-Chloropyrimidin-4-yloxy)-quinoline

A mixture of 2,4-dichloropyrimidine (1.0 g, 6.7 mmol), 6-hydroxyquinoline (1.0 g, 6.89 mmol) and $Na_2CO_3$ (2.84 g, 26.8 mmol) in EtOH (50 mL) was stirred for 18 h at RT. The solids were removed by suction filtration and the organics were concentrated under reduced pressure. The crude was purified via medium pressure liquid chromatography using a linear gradient starting from 0:100 MeOH/$CH_2Cl_2$ ending with 10:90 MeOH/$CH_2Cl_2$ as the solvent system. The desired compound was obtained as a white solid.

Preparation R—(4-Dipropylsulfamoyl-phenyl)-carbamic acid tert-butyl ester

A mixture of Probenecid [4-[(dipropylamino)sulfonyl] benzoic acid] (2.0 g, 7.0 mmol), TEA (2.9 mL, 21.0 mmol) and DPPA (1.7 mL, 7.7 mmol) in toluene (15 mL) and t-BuOH (5 mL) was heated 90° C. for 3 h. The mixture was poured into EtOAc (100 mL) and washed with water (50 mL). The organics were dried over anhydrous $MgSO_4$ and the organics were concentrated under reduced pressure. The crude was purified via medium pressure liquid chromatography using $CH_2Cl_2$ followed by 5:95 MeOH/$CH_2Cl_2$ as the solvent system to give the desired material.

Preparation S—4-Amino-N,N-dipropyl-benzenesulfonamide (4-Dipropylsulfamoyl-phenyl)-carbamic acid tert-butyl ester (1.32 g, 3.7 mmol) in $CH_2Cl_2$ (25 mL) was added TFA (10 mL). The mixture was stirred at RT for 4 h. The organics were concentrated under reduced pressure, the residue taken up in sat NaHCO$_3$ (40 mL) and the organics extracted into EtOAc (150 mL). The organics were dried over anhydrous Na$_2$SO$_4$ and the organics concentrated under reduced pressure to give the desired compound as a white solid.

Preparation T—1-Methoxy-isoquinoin-3-ylamine

To a solution of 1-bromo-isoquinolin-3-ylamine (1.0 g, 4.48 mmol) in DMF (20 mL) and MeOH (5 mL) at RT was added KOt-Bu (2.51 g, 22.41 mmol). The mixture turned from yellow to red in color and was stirred for 3 days at RT. NH$_4$Cl (aq., sat., 10 mL) was added, followed by H$_2$O (50 mL) and the mixture was extracted with EtOAc (3×15 mL). The organic layers were combined, washed with brine, dried with MgSO$_4$ and filtered. After concentration, the crude reaction mixture was purified by chromatography on silica gel (9:1 Hexanes:EtOAc) to afford pure 1-methoxy-isoquinoin-3-ylamine.

Preparation U—(2-Chloro-pyrimidin-4-yl)-(1-methoxy-isoquinolin-3-yl)-amine

To a slurry of 1-methoxy-isoquinoin-3-ylamine (0.682 g, 3.92 mmol) and 2,4-dichloropyrimidine (0.583 g, 3.92 mmol) in IPA (10 mL) was added DIEA (0.683 mL, 3.92 mmol). The reaction was heated in a sealed tube at 110° C. for 8 h, then an additional portion of DIEA (0.5 mL, 2.88 mmol) was added. The mixture was heated for another 24 h at 110° C., during which time needle-like crystals precipitated from solution. The mixture was filtered and washed with hexanes (3×5 mL) to afford pure (2-chloro-pyrimidin-4-yl)-(1-methoxy-isoquinolin-3-yl)-amine.

EXAMPLE 1

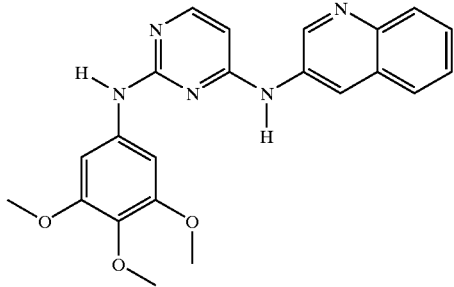

N$^4$-Quinolin-3-yl-N$^2$-(3,4,5-trimethoxyphenyl)pyrimidine-2,4-diamine

A mixture of (2-chloro-pyrimidin-4-yl)-quinolin-3-yl-amine (100 mg, 0.39 mmol) and 3,4,5-trimethoxyaniline was suspended in acetone (7 mL) and water (2 mL) with 2 drops of conc. HCl. The mixture was heated in a sealed tube to reflux overnight. The mixture was poured into EtOAc (100 mL) and sat. aq. NaHCO$_3$. The organics were separated, dried over anhydrous Na$_2$SO$_4$ and concentrated under reduced pressure. The crude was purified via preparative HPLC. MS m/z=404. Calc'd for C$_{22}$H$_{21}$N$_5$O$_3$: 403.16.

EXAMPLES 2–20

Examples 2–20 were prepared from the corresponding amines in a manner similar to that described above for Example 1:

2. N$^4$-quinolin-3-yl-N$^2$-(6-benzimidazolyl)pyrimidine-2,4-diamine [M+H—354. Calc'd for C$_{20}$H$_{15}$N$_7$: 353.388];
3. N$^4$-quinolin-6-yl-N$^2$-(6-benzimidazolyl)pyrimidine-2,4-diamine [M+H—354. Calc'd for C$_{20}$H$_{15}$N$_7$: 353.388];
4. N$^4$-quinolin-3-yl-N$^2$-(5-indazolyl)pyrimidine-2,4-diamine [M+H—354. Calc'd for C$_{20}$H$_{15}$N$_7$: 353.388];
5. N$^4$-quinolin-6-yl-N$^2$-(5-indazolyl)pyrimidine-2,4-diamine [M+H—354. Calc'd for C$_{20}$H$_{15}$N$_7$: 353.388];
6. N$^4$-quinolin-3-yl-N$^2$-(6-indazolyl)pyrimidine-2,4-diamine [M+H—354. Calc'd for C$_{20}$H$_{15}$N$_7$: 353.388];
7. N$^4$-quinolin-6-yl-N$^2$-(6-indazolyl)pyrimidine-2,4-diamine [M+H—354. Calc'd for C$_{20}$H$_{15}$N$_7$: 353.388];
8. N$^4$-quinolin-3-yl-N$^2$-(2,5-dimethoxyphenyl)pyrimidine-2,4-diamine [M+H—374. Calc'd for C$_{21}$H$_{19}$N$_5$O$_2$: 373.414];
9. N$^4$-quinolin-3-yl-N$^2$-(3,4-dimethoxyphenyl)pyrimidine-2,4-diamine [M+H—374. Calc'd for C$_{21}$H$_{19}$N$_5$O$_2$: 373.414];
10. N$^4$-quinolin-3-yl-N$^2$-(3-quinolinyl)pyrimidine-2,4-diamine [M+H—365. Calc'd for C$_{22}$H$_{16}$N$_6$: 364.41];
11. N$^4$-quinolin-6-yl-N$^2$-(3-quinolinyl)pyrimidine-2,4-diamine [M+H—365. Calcd for C$_{22}$H$_{16}$N$_6$: 364.41];
12. N$^4$-quinolin-3-yl-N$^2$-(6-quinolinyl)pyrimidine-2,4-diamine [M+H—365. Calc'd for C$_{22}$H$_{16}$N$_6$: 364.41];
13. N$^4$-quinolin-6-yl-N$^2$-(6-quinolinyl)pyrimidine-2,4-diamine [M+H—365. Calc'd for C$_{22}$H$_{16}$N$_6$: 364.41];
14. N$^4$-quinolin-6-yl-N$^2$-(3,4,5-trimethoxyphenyl)-pyrimidine-2,4-diamine [M+H—404. Calc'd for C$_{22}$H$_{21}$N$_5$O$_3$: 403.44];
15. N$^2$-(3-aminosulfonylphenyl)-N$^4$-quinolin-6-yl-pyrimidine-2,4-diamine [M+H—393. Calc'd for C$_{19}$H$_{16}$N$_6$O$_2$S: 392.441];
16. N$^2$-(3-aminosulfonylphenyl)-N$^4$-quinolin-3-yl-pyrimidine-2,4-diamine [M+H—393. Calc'd for C$_{19}$H$_{16}$N$_6$O$_2$S: 392.441];
17. N$^2$-(4-aminosulfonylphenyl)-N$^4$-quinolin-6-yl-pyrimidine-2,4-diamine [M+H—393. Calc'd for C$_{19}$H$_{16}$N$_6$O$_2$S: 392.441];
18. N$^2$-(4-aminosulfonylphenyl)-N$^4$-quinolin-3-yl-pyrimidine-2,4-diamine [M+H—393. Calc'd for C$_{19}$H$_{16}$N$_6$O$_2$S: 392.441];
19. N$^2$-(3,4-dimethoxy-6-methylphenyl)-N$^4$-quinolin-6-yl-pyrimidine-2,4-diamine [M+H—388. Calc'd for C$_{22}$H$_{21}$N$_5$O$_2$: 387.441]; and
20. N$^2$-(3,4-dimethoxy-6-methylphenyl)-N$^4$-quinolin-3-yl-pyrimidine-2,4-diamine [M+H—388. Calc'd for C$_{22}$H$_{21}$N$_5$O$_2$: 387.441].

EXAMPLES 21–64

Examples 21–64 were prepared from the corresponding amines in a manner similar to that described above for Example 1.

(2-Chloro-pyrimidin-4-yl)-quinolin-3-yl-amine (0.58 mmol) and 1–2 equivalents of the appropriate amine were mixed in a solution of IPA (2 mL) and HCl (1–2 equiv., 4 M in dioxane), and heated under stirring at 120° C. in a sealed tube for 15–48 h. The reaction was monitored by TLC (Silicagel Merck F 254 (CH$_2$Cl$_2$/MeOH, 90/10 v/v or EtOAc/MeOH 90/10 v/v). The mixture was cooled to RT and sat. aq. NaHCO$_3$ solution (3 mL) was added. Depending on the solubility of the reaction product, work up procedure A or B was performed.

Work up procedure A: If the desired product was soluble in CH$_2$Cl$_2$ or EtOAc, the mixture containing the sat. aq. NaHCO$_3$ solution was extracted with EtOAc (10 mL) or CH$_2$Cl$_2$ (10 mL). The organic layer was dried over Na$_2$SO$_4$ and the solvent was evaporated. The crude material was purified by silica gel (silica gel 60, Merck) chromatography (CH$_2$Cl$_2$/IPA 90/10 v/v).

Work up procedure B: If the desired product was insoluble in CH$_2$Cl$_2$ or EtOAc, the mixture containing the sat. aq. NaHCO$_3$ solution was washed with medium to non-polar solvents (EtOAc, or Et$_2$O, 10 mL), 2 times to remove the soluble undesired byproducts.

| Example | Structure | Mass Calc'd | Mass Obs. |
|---------|-----------|-------------|-----------|
| 21 | N²-(3-pyridinyl)-N⁴-(3-quinolinyl)-2,4-pyrimidinediamine | 314 | 315.59 |
| 22 | N²-(2-fluorophenyl)-N⁴-(3-quinolinyl)-2,4-pyrimidinediamine | 331 | 332.56 |
| 23 | N²-(3-fluorophenyl)-N⁴-(3-quinolinyl)-2,4-pyrimidinediamine | 331 | 332.56 |
| 24 | N²-(4-fluorophenyl)-N⁴-(3-quinolinyl)-2,4-pyrimidinediamine | 331 | 332.56 |
| 25 | N²-(6-(methoxy)-3-pyridinyl)-N⁴-(3-quinolinyl)-2,4-pyrimidinediamine | 344 | 345.57 |
| 26 | N²-(3-chlorophenyl)-N⁴-(3-quinolinyl)-2,4-pyrimidinediamine | 347 | 348.52 |

| Example | Structure | Mass Calc'd | Mass Obs. |
|---|---|---|---|
| 27 | N²-(4-chlorophenyl)-N⁴-(3-quinolinyl)-2,4-pyrimidinediamine | 347 | 348.52 |
| 28 | N²-(1H-indol-4-yl)-N⁴-(3-quinolinyl)-2,4-pyrimidinediamine | 352 | 353.57 |
| 29 | N²-(1H-1,2,3-benzotriazol-5-yl)-N⁴-(3-quinolinyl)-2,4-pyrimidinediamine | 354 | 355.56 |
| 30 | 3-((4-(3-quinolinylamino)-2-pyrimidinyl)amino)-benzamide | 356 | 357.57 |
| 31 | N²-(4-(dimethylamino)phenyl)-N⁴-(3-quinolinyl)-2,4-pyrimidinediamine | 356 | 357.60 |
| 32 | N²-(3-(dimethylamino)phenyl)-N⁴-(3-quinolinyl)-2,4-pyrimidinediamine | 356 | 357.60 |

-continued

| Example | Structure | Mass Calc'd | Mass Obs. |
| --- | --- | --- | --- |
| 33 | $N^2$-(4-nitrophenyl)-$N^4$-(3-quinolinyl)-2,4-pyrimidinediamine | 358 | 359.53 |
| 34 | $N^2$-(3-fluoro-4-(methoxy)phenyl)-$N^4$-(3-quinolinyl)-2,4-pyrimidinediamine | 361 | 362.55 |
| 35 | $N^2$-(3-chloro-4-fluorophenyl)-$N^4$-(3-quinolinyl)-2,4-pyrimidinediamine | 365 | 366.50 |
| 36 | N-(4-((4-(3-quinolinylamino)-2-pyrimidinyl)amino)phenyl)acetamide | 370 | 371.56 |
| 37 | N-(3-((4-(3-quinolinylamino)-2-pyrimidinyl)amino)phenyl)acetamide | 370 | 371.56 |

| Example | Structure | Mass Calc'd | Mass Obs. |
|---|---|---|---|
| 38 | N²-(1,3-benzothiazol-6-yl)-N⁴-(3-quinolinyl)-2,4-pyrimidinediamine | 370 | 371.51 |
| 39 | methyl 4-((4-(3-quinolinylamino)-2-pyrimidinyl)amino)-benzoate | 371 | 372.54 |
| 40 | methyl 3-((4-(3-quinolinylamino)-2-pyrimidinyl)amino)-benzoate | 371 | 372.54 |
| 41 | N²-(3-chloro-4-(methoxy)phenyl)-N⁴-(3-quinolinyl)-2,4-pyrimidinediamine | 377 | 378.50 |
| 42 | N-(3,4-dichropheflyl)-N⁴-(3-quinolinyl)-2,4-pyrimidinediamine | 382 | 382.45 |

| Example | Structure | Mass Calc'd | Mass Obs. |
|---|---|---|---|
| 43 | N-(3,5-dichlorophenyl)-N$^4$-(3-quinolinyl)-2,4-pyrimidinediamine | 382 | 382.45 |
| 44 | N$^2$-(4-methoxy-2-nitrophenyl)-N$^4$-(3-quinolinyl)-2,4-pyrimidinediamine | 388 | 389.51 |
| 45 | N$^2$-(2-methoxy-4-nitrophenyl)-N$^4$-(3-quinolinyl)-2,4-pyrimidinediamine | 388 | 389.52 |
| 46 | N$^2$-(2,2-difluoro-1,3-benzodioxol-5-yl)-N$^4$-(3-quinolinyl)-2,4-pyrimidinediamine | 393 | 394.48 |
| 47 | 4,5-bis(methoxy)-2-((4-(3-quinolinylamino)-2-pyrimidinyl)amino)-benzonitrile | 398 | 399.52 |

-continued

| Example | Structure | Mass Calc'd | Mass Obs. |
|---|---|---|---|
| 48 | 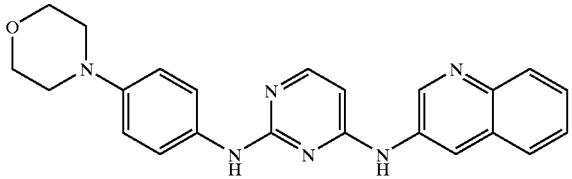<br>N²-(4-(4-morpholinyl)phenyl)-N⁴-(3-quinolinyl)-2,4-pyrimidinediamine | 398 | 399.56 |
| 49 | 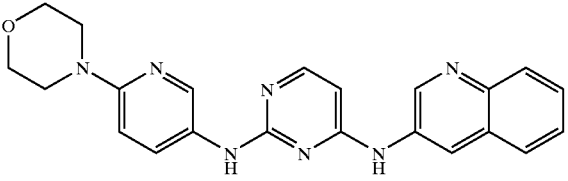<br>N²-(6-(4-morpholinyl)-3-pyridinyl)-N⁴-(3-quinolinyl)-2,4-pyrimidinediamine | 399 | 400.56 |
| 50 | 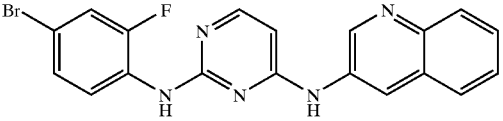<br>N²-(4-bromo-2-fluorophenyl)-N⁴-(3-quinolinyl)-2,4-pyrimidinediamine | 409 | 410.40 |
| 51 | 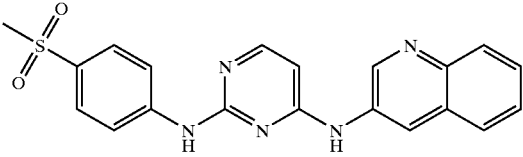<br>N²-(4-(methylsulfonyl) phenyl)-N⁴-(3-quinolinyl)-2,4-pyrimidinediamine | 391 | 392.50 |
| 52 | 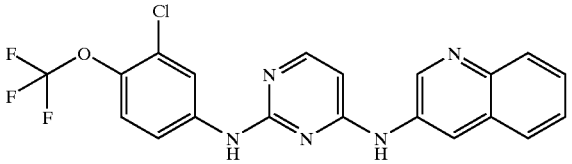<br>N²-(3-chloro-4-trifluoromethoxy)phenyl)-N⁴-(3-quinolinyl)-2,4-pyrimidinediamine | 431 | 432.41 |

| Example | Structure | Mass Calc'd | Mass Obs. |
|---|---|---|---|
| 53 | N²-(4-diethylamino-2-methylphenyl)-N⁴-(3-quinolinyl)-2,4-pyrimidinediamine | 398 | 399.60 |
| 54 | N-butyl-3-((4-(3-quinolinylamino)-2-pyrimidinyl)amino)-benzenesulfonamide | 448 | 449.49 |
| 55 | 2-((3-((4-(3-quinolinylamino)-2-pyrimidinyl)amino)phenyl)sulfonyl)ethanol | 421 | 422.48 |
| 56 | 4-((4-(3-quinolinylamino)-2-pyrimidinyl)amino)-N-(1,3-thiazol-2-yl)benzenesulfonamide | 475 | 476.38 |

-continued

| Example | Structure | Mass Calc'd | Mass Obs. |
|---|---|---|---|
| 57 | N-(3-bromophenyl)N⁴-(3-quinolinyl)-2,4-pyrimidinediamine | 392 | 392.43 |
| 58 | 2-methyl-5-((4-(3-quinolinylamino)-2-pyrimidinyl)amino)-1H-isoindole-1,3(2H)-dione | 396 | 397.52 |
| 59 | 1-(4-((4-(3-quinalinylamino)-2-pyrimidinyl)amino)phenyl)ethanone | 355.399 | 356.56 |
| 60 | N²-(4-bromophenyl)-N⁴-(3-quinolinyl)-2,4-pyrimidinediamine | 392 | 392.43 |
| 61 | N²-(1H-indol-5-yl)-N⁴-(3-quinolinyl)-2,4-pyrimidinediamine | 352 | 353.00 |
| 62 | 4-((4-(3-quinolinylamino)-2-pyrimidinyl)amino)-benzamide | 356 | 357.12 |

| Example | Structure | Mass Calc'd | Mass Obs. |
|---|---|---|---|
| 63 | N-acetyl-4-((4-(3-quinolinylamino)-2-pyrimidinyl)amino)-benzenesulfonamide | 434 | 434.90 |
| 64 | $N^2$-(2-bromophenyl)-$N^4$-(3-quinolinyl)-2,4-pyrimidinediamine | 392 | 391.80 |

EXAMPLE 65

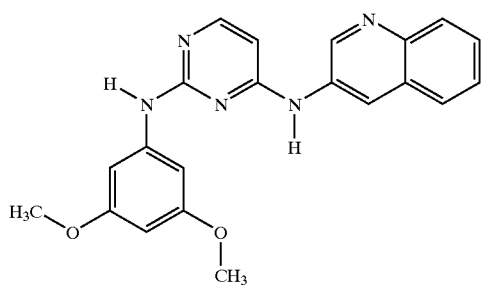

$N^4$-Quinolin-3-yl-$N^2$-(3,5-dimethoxyphenyl)pyrimidine-2,4-diamine

A mixture of (2-chloro-pyrimidin-4-yl)-quinolin-3-yl-amine (70 mg 0.272 mmol) and 3,5-dimethoxyaniline (42 mg, 0.274 mmol) was suspended in a sealed tube with 0.3 mL of a solution of DMSO containing $Et_3N$-TFA (50 mg). The resulting mixture was heated at 100° C. for 3 h, cooled to RT, diluted with 0.4 mL DMSO and purified via preparative HPLC to give $N^4$-quinolin-3-yl-$N^2$-(3,5-dimethoxyphenyl)pyrimidine-2,4-diamine as a yellow solid. M+H—374. Calc'd for $C_{21}H_{19}N_5O_2$: 373.414.

EXAMPLES 66–86

Examples 66–86 were prepared from the corresponding amines in a manner similar to that described above for Example 65.

| Example | Structure | Mass Calc'd | Mass Obs. | Notes |
|---|---|---|---|---|
| 66 | $N^4$-Quinolin-6-yl-$N^2$-(3,4-dimethoxyphenyl)-pyrimidine-2,4-diamine | 373 | 374 | light yellow solid |

-continued

| Example | Structure | Mass Calc'd | Mass Obs. | Notes |
|---|---|---|---|---|
| 67 | N⁴-Quinolin-6-yl-N²-(2,5-dimethoxyphenyl)-pyrimidine-2,4-diamine | 373 | 374 | light yellow solid |
| 68 | N²-(1,3-benzodioxol-5-yl)-N4-(3-quinolinyl)-2,4-pyrimidinediamine | 357 | 358 | light yellow solid |
| 69 | N²-(2-methoxyphenyl)-N⁴-(3-quinolinyl)-2,4-pyrimidinediamine | 343 | 344 | yellow solid |
| 70 | N²-(2-methoxyphenyl)-N⁴-(6-quinolinyl)-2,4-pyrimidinediamine | 343 | 344 | yellow solid |

-continued

| Example | Structure | Mass Calc'd | Mass Obs. | Notes |
|---|---|---|---|---|
| 71 | N²-(3-methoxyphenyl)-N⁴-(3-quinolinyl)-2,4-pyrimidinediamine | 343 | 344 | yellow solid |
| 72 | N²-(3-methoxyphenyl)-N⁴-(6-quinolinyl)-2,4-pyrimidinediamine | 343 | 344 | yellow solid |
| 73 | N²-(4-methoxyphenyl)-N⁴-(3-quinolinyl)-2,4-pyrimidinediamine | 343 | 344 | Yellow solid |
| 74 | N²-(4-methoxyphenyl)-N⁴-(6-quinolinyl)-2,4-pyrimidinediamine | 343 | 344 | light yellow solid |

-continued

| Example | Structure | Mass Calc'd | Mass Obs. | Notes |
|---|---|---|---|---|
| 75 | N²-(3,4-bis(ethoxy)phenyl)-N⁴-(3-quinolinyl)-2,4-pyrimidinediamine | 401 | 402 | Tan solid |
| 76 | N²-(3,4-bis(ethoxy)phenyl)-N⁴-(6-quinolinyl)-2,4-pyrimidinediamine | 401 | 402 | yellow solid |
| 77 | N²-(3,5-bis(trifluoromethyl)phenyl)-N⁴-(3-quinolinyl)-2,4-pyrimidinediamine | 449 | 450 | Tan solid |

-continued

| Example | Structure | Mass Calc'd | Mass Obs. | Notes |
|---|---|---|---|---|
| 78 | 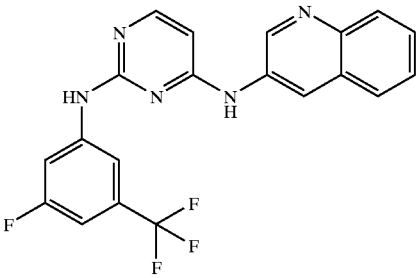<br>N²-(3-fluoro-5-(trifluoromethyl)phenyl)-N⁴-(3-quinolinyl)-2,4-pyrimidinediamine | 399 | 400 | Tan solid |
| 79 | 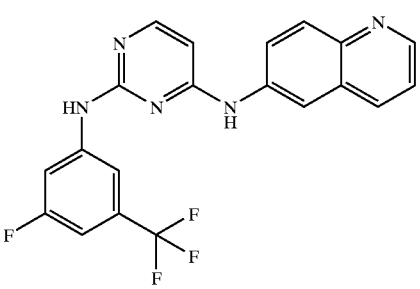<br>N²-(3-fluoro-5-(trifluoromethyl)phenyl)-N⁴-(6-quinolinyl)-2,4-pyrimidinediamine | 399 | 400 | off-white solid |
| 80 | 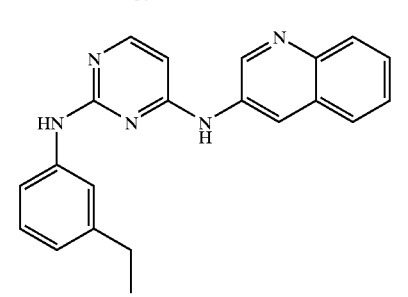<br>N²-(3-ethylphenyl)-N⁴-(3-quinolinyl)-2,4-pyrimidinediamine | 341 | 342 | white solid |
| 81 | 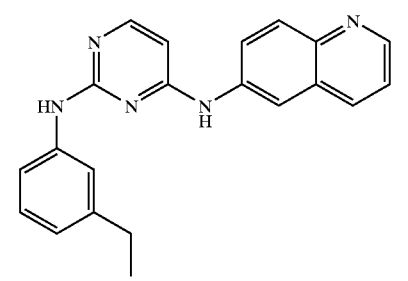<br>N²-(3-ethylphenyl)-N⁴-(6-quinolinyl)-2,4-pyrimidinediamine | 341 | 342 | yellow solid |

-continued
| Example | Structure | Mass Calc'd | Mass Obs. | Notes |
|---|---|---|---|---|
| 82 | 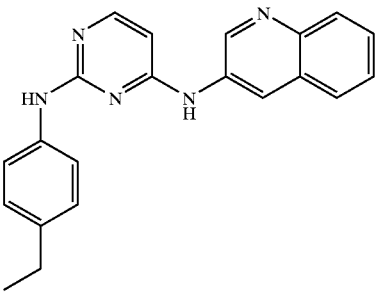<br>N²-(4-ethylphenyl)-N⁴-(3-quinolinyl)-2,4-pyrimidinediamine | 341 | 342 | off-white solid |
| 83 | 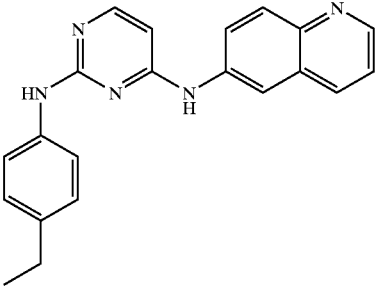<br>N²-(4-ethylphenyl)-N⁴-(6-quinolinyl)-2,4-pyrimidinediamine | 341 | 342 | yellow solid |
| 84 | 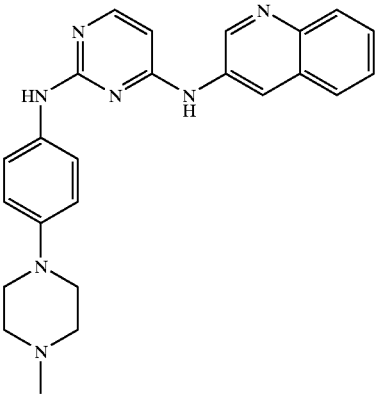<br>N²-(4-(4-methyl-1-piperazinyl)phenyl)-N⁴-(3-qulnolinyl)-2,4-pyrimidinediamine | 411 | 413 | Brown solid |

| Example | Structure | Mass Calc'd | Mass Obs. | Notes |
|---|---|---|---|---|
| 85 | N²-(3-Trifluoromethyl-5-methoxyphenyl)-N⁴-(3-quinolino)-2,4-pyrimidinediamine | 411.4 | 412.4 | |
| 86 | N²-(3-trifluoromethyl-4-methoxyphenyl)-N⁴-(3-quinolino)-2,4-pyrimidinediamine | 411.4 | 412.4 | |

EXAMPLE 87

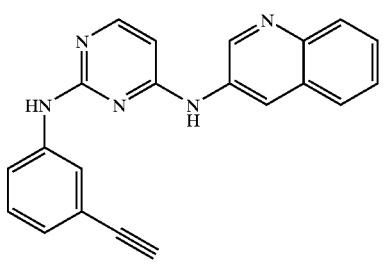

$N^2$-(3-Ethynylphenyl)-$N^4$-(3-quinolinyl)-2,4-pyrimidinediamine

A mixture of (2-chloro-pyrimidin-4-yl)-quinolin-3-yl-amine (70 mg 0.272 mmol) and 3-ethynylaniline (33 mg, 0.282 mmol) was suspended in a sealed tube with 0.3 mL of DMSO. The resulting mixture was heated at 100° C. for 2 h, cooled to RT, diluted with $CH_2Cl_2$. The precipitate was collected by suction filtration then dried under vacuum to give the desired product as an off-white solid. M+H—338; Calc'd for $C_{21}H_{15}N_5$: 337.13.

EXAMPLES 88–90

Examples 88–90 were prepared from the corresponding amines in a manner similar to that described above for Example 87.

| Example | Structure | Mass Calc'd | Mass Obs. | Notes |
|---|---|---|---|---|
| 88 | 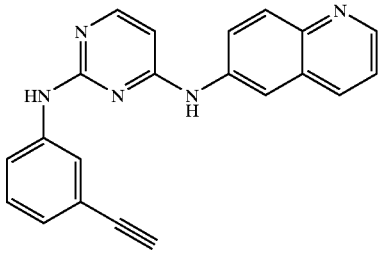<br>N²-(3-Ethynylphenyl)-N⁴-(6-quinolinyl)-2,4-pyrimidinediamine | 337 | 338 | off-white solid |
| 89 | 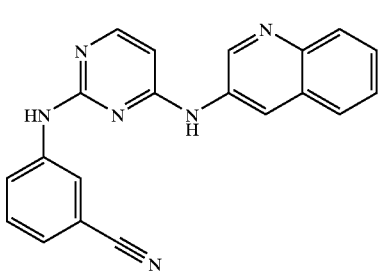<br>3-((4-(3-quinolinylamino)-2-pyrimidinyl)amino)-benzonitrile | 338 | 339 | Tan solid |
| 90 | 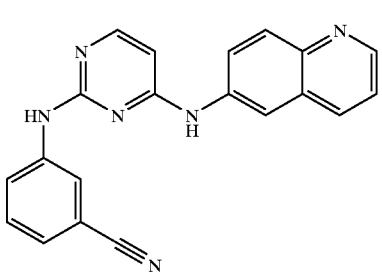<br>3-((4-(6-quinolinylamino)-2-pyrimidinyl)amino)-benzonitrile | 338 | 339 | yellow solid |

EXAMPLE 91

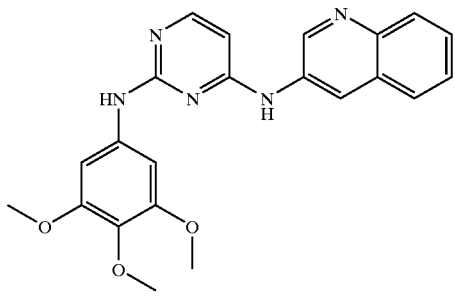

N⁴-(3-Isoquinolinyl)-N²-(3,4,5-tris(methoxy)phenyl)-2,4-pyrimidinediamine

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 2:98 MeOH/CH$_2$Cl$_2$ followed 5:95 MeOH/CH$_2$Cl$_2$ as the solvent system. The desired product was obtained as a tan solid. M+H—404; Calc'd for C$_{22}$H$_{21}$N$_5$O3—403.

EXAMPLE 92

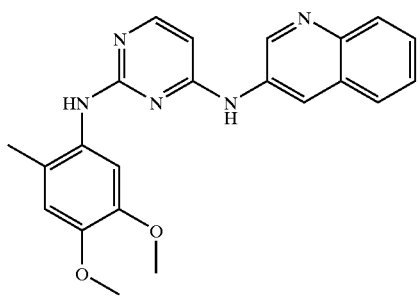

$N^4$-(3-Isoquinolinyl)-$N^2$-(2-methyl-4,5-bis(methoxy)phenyl)-2,4-pyrimidinediamine The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 4:96 MeOH/CH$_2$Cl$_2$ as the solvent system. The desired product was obtained as a brown solid. M+H—388; Calc'd for $C_{22}H_{21}N_5O_2$— 387.

EXAMPLE 93

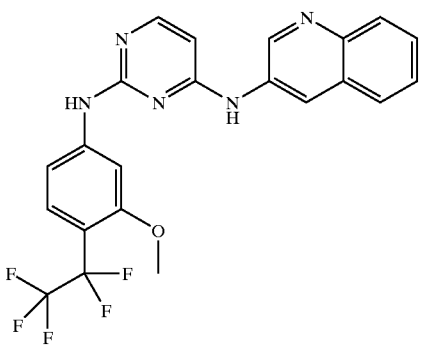

$N^2$-(3-(Methoxy)-4-(pentafluoroethyl)phenyl)-$N^4$-(3-quinolinyl)-2,4-pyrimidinediamine The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 5:95 MeOH/CH$_2$Cl$_2$ as the solvent system. The desired product was obtained as a brown solid. M+H—462; Calc'd for $C_{22}H_{16}F_5N_5O$: 461.13.

EXAMPLE 94

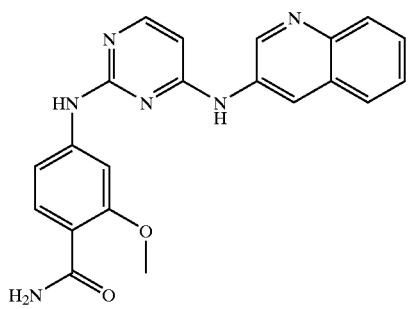

2-(Methoxy)-4-((4-(3-quinolinylamino)-2-pyrimidinyl)amino)benzamide

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 4:96 MeOH/CH$_2$Cl$_2$ followed by 1.0:10:90 conc. NH$_4$OH/MeOH/CH$_2$Cl$_2$ as the solvent system. The desired product was obtained as a tan solid. M+H—387; Calc'd for $C_{21}H_{18}N_6O_2$—386.

EXAMPLE 95

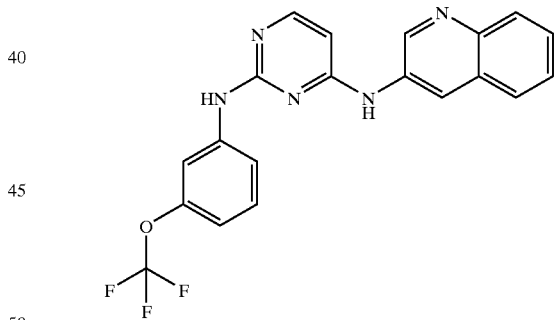

$N^4$-(3-Quinolinyl)-$N^2$-(3-(trifluoromethoxy)phenyl)-2,4-pyrimidinediamine

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 1:99 MeOH/CH$_2$Cl$_2$ followed by 3:97 MeOH/CH$_2$Cl$_2$ as the solvent system. The desired product was obtained as a white solid. M+H—398; Calc'd for $C_{20}H_{14}F_3N_5O$—397.

EXAMPLE 96

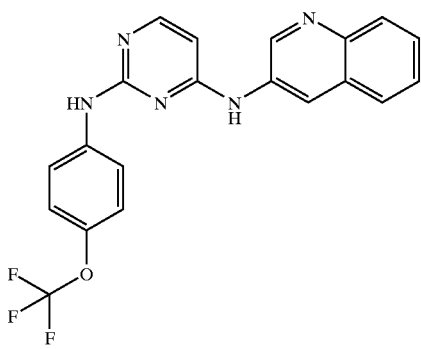

N⁴-(3-Quinolinyl)-N²-(4-(trifluoromethoxy)phenyl)-2,4-pyrimidinediamine

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 1:99 MeOH/CH$_2$Cl$_2$ followed by 3:97 MeOH/CH$_2$Cl$_2$ as the solvent system. The desired product was obtained as a white solid. M+H—398; Calc'd for C$_{20}$H$_{14}$F$_3$N$_5$O—397.

EXAMPLE 97

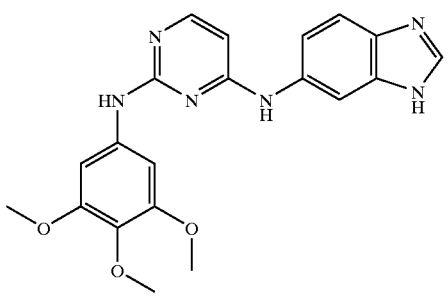

N⁴-(1H-Benzimidazol-6-yl)-N²-(3,4,5-tris(methoxy)phenyl)-2,4-pyrimidinediamine

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using 3:97 MeOH/CH$_2$Cl$_2$ followed by 5:95 MeOH/CH$_2$Cl$_2$ followed by 1.0:10:90 conc. NH$_4$OH/MeOH/CH$_2$Cl$_2$ as the solvent system. The desired product was obtained as a black solid. M+H—393; Calc'd for C$_{20}$H$_{20}$N$_6$O$_3$—392.

EXAMPLE 98

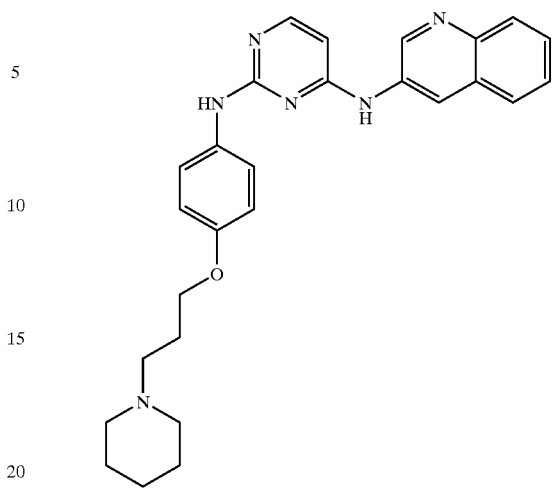

N²-[4-(3-Piperidin-1-yl-propoxy)-phenyl]-N⁴-4-quinolin-3-yl-pyrimidine-2,4-diamine A mixture of (2-chloro-pyrimidin-4-yl)-quinolin-3-yl-amine (958 mg 3.41 mmol) and 4-(3-piperidin-1-yl-propoxy)-phenylamine (800 mg, 3.41 mmol) was suspended in a sealed tube with 0.6 mL of DMSO. The resulting mixture was heated at 90° C. for 72 h, cooled to RT, diluted with EtOAc. The precipitate was collected by suction filtration then dried under vacuum. The crude was purified via medium pressure liquid chromatography using 5:95 MeOH/CH$_2$Cl$_2$ followed by 10:90 MeOH/CH$_2$Cl$_2$ followed by 15:85 MeOH/CH$_2$Cl$_2$ as the solvent system. The desired product was obtained as a tan solid. M+H—455; Calc'd for C$_{27}$H$_{30}$N$_6$O—454.

EXAMPLE 99

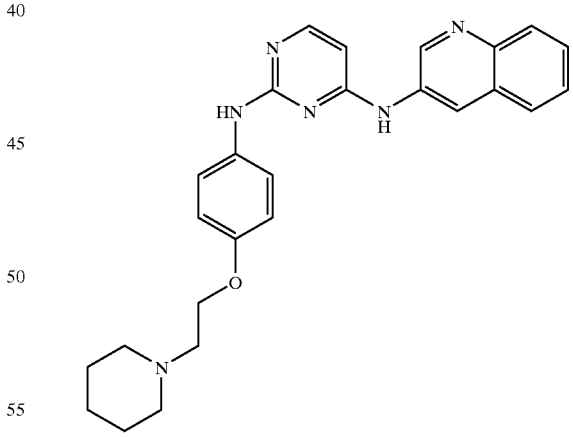

N²-(4-((2-(1-Piperidinyl)ethyl)oxy)phenyl)-N⁴-(3-quinolinyl)-2,4-pyrimidinediamine The compound was prepared from the corresponding amine in a manner similar to that described for examples 87 and 98. The crude was purified via medium pressure liquid chromatography using 3:97 MeOH/CH$_2$Cl$_2$ followed by 10:90 MeOH/CH$_2$Cl$_2$ as the solvent system. The desired product was obtained as a tan solid. M+H—441; Calc'd for C$_{26}$H$_{28}$N$_6$O—440.

EXAMPLE 100

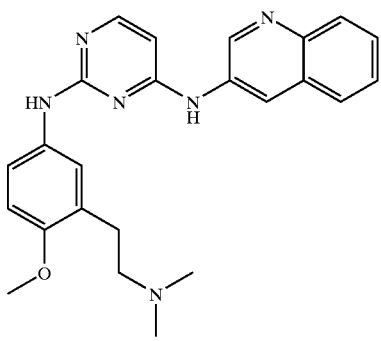

N²-(3-(2-(Dimethylamino)ethyl)-4-(methoxyphenyl)-N⁴-(3-quinolinyl)-2,4-pyrimidinediamine Step A 2-Bromomethyl-1-methoxy-4-nitro-benzene (25 g) was dissolved in warm EtOH (45 mL) and stirred while slowly adding a solution of NaCN (6.0 g in 12 mL water) at 70° C. After the addition was complete, the reaction was stirred at 70° C. for 90 min. The inorganic solid, which separated on cooling, was collected and washed well with $CH_3CN$. The $CH_3CN$ filtrate was filtered again giving further inorganic solid, and again washed with $CH_3CN$. The final $CH_3CN$ filtrate was evaporated giving a red-brown solid. This solid was triturated with $CH_2Cl_2$ until the washings were colorless. Evaporation of the $CH_2Cl_2$ filtrate gave (2-methoxy-5-nitrophenyl)-acetonitrile as a red-brown solid, which was used without further purification.

Step B

The crude (2-methoxy-5-nitrophenyl)-acetonitrile (Step A) was stirred and heated with 20 mL of 12 M HCl at reflux for 3 h and then at 60° C. overnight. After cooling, the product was extracted into $CH_2Cl_2$ (3×40 mL), washed with water then extracted into 3M NaOH. The basic extracts were washed with $CH_2Cl_2$, acidified (6M HCl) and the solid was collected, washed well with water and dried in air giving pure 2-(2-methoxy-5-nitrophenyl)acetic acid. Evaporation of the $CH_2Cl_2$ extracts and retreating the residual solid with 50 mL of 12M HCl/20 mL water under reflux for 6 h followed by purification as above gave additional pure 2-(2-methoxy-5-nitrophenyl)acetic acid.

Step C 2-(2-Methoxy-5-nitrophenyl)acetic acid (17.1 g, 1 eq, Step B), EDC (18.6 g, 1.2 eq.), $Et_3N$ (9.8 g, 13.6 mL, 1.2 eq) and dimethylamine hydrochloride (7.9 g, 1.2 eq.) in 150 mL of $CH_2Cl_2$ were stirred together with exclusion of air overnight. $CH_2Cl_2$ (150 mL) was added and the mixture was washed twice with 1M HCl, twice with 1M NaOH, water and brine. Removal of the solvent under reduced pressure followed by silica gel chromatography (90:10 $CH_2Cl_2$:EtOAc) afforded pure 2-(2-methoxy-5-nitrophenyl)-N,N-dimethyl-acetamide as a white solid.

Step D 2-(2-Methoxy-5-nitrophenyl)-N,N-dimethyl-acetamide (15.0 g, Step C) was added to 126 mL of 1M $BH_3$-THF (2 eq.) under $N_2$ and the resulting mixture was heated at reflux. After 2 h, additional $BH_3$-THF was added (120 mL) followed by 0.2 mL of boron trifluoride etherate and heating was continued for 13 h. Evaporation and azeotroping the residue from MeOH 3× gave a semi-solid residue which was washed with MeOH and filtered to give the boric acid salt of [2-(2-methoxy-5-nitrophenyl)-ethyl]-dimethyl-amine as a white solid.

Step E

To a solution of [2-(2-methoxy-5-nitrophenyl)-ethyl]-dimethyl-amine (1.0 g, Step D) dissolved in EtOH (20 mL) was added 10% Pd/C (0.1 g). The reaction vessel was capped with a rubber septum and $H_2$ gas was introduced through a balloon/needle. The reaction was stirred vigorously overnight at RT, and which time it was filtered through sand/Celite®. Concentration of the crude mixture provided a beige oil which was purified by chromatography on silica gel (97:3 $CH_2Cl_2$:MeOH) to afford pure 3-(2-dimethylamino-ethyl)-4-methoxy-phenylamine as a white solid.

Step F

The title compound was prepared from the corresponding amine prepared in Step E in a manner similar to that described for Example 87 to give the desired product as a tan solid. M+H—415; Calc'd for $C_{24}H_{26}N_6O$—414.

EXAMPLE 101

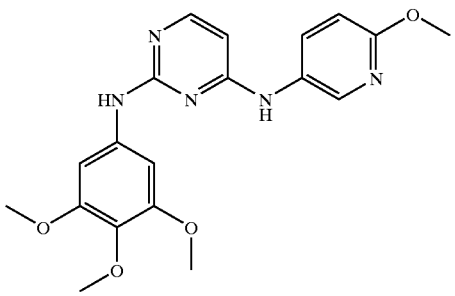

N⁴-(6-(Methoxy)-3-pyridinyl)-N²-(3,4,5-tris(methoxy)phenyl)-2,4-pyrimidinediamine A mixture of 2,4-dichloropyrimidine (50 mg, 0.34 mmol), 5-amino-2-methoxypyridine (42 mg, 0.34 mmol) and DIEA (0.2 mL) in IPA (1.5 mL) was heated to reflux for 3 h in a sealed tube. Trimethoxyaniline (62 mg, 0.34 mmol) was added with 0.2 mL of DMSO. The resulting mixture was heated at 95° C. overnight allowing the solvent to evaporate. The crude was taken up in DMSO then purified via preparative HPLC to give the desired compound as an off-white solid. M+H—384; Calc'd for $C_{19}H_{21}N_5O_4$—383.

EXAMPLE 102

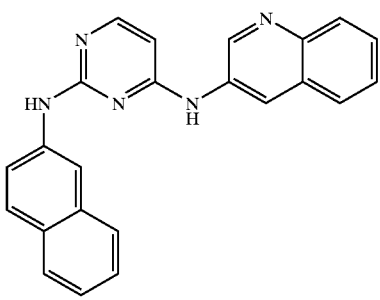

N²-(2-Naphthalenyl)-N⁴-(3-quinolinyl)-2,4-pyrimidinediamine

The compound was prepared from the corresponding amine in a manner similar to that described above for Example 87. The crude was purified via medium pressure liquid chromatography using linear gradient starting from 0:0:100 conc. $NH_4OH/MeOH/CH_2Cl_2$ ending with 1.0:10:90 conc. $NH_4OH/MeOH/CH_2Cl_2$ as the solvent system. The desired product was obtained as a white solid. M+H—364; Calc'd for $C_{23}H_{17}N_5$—363.

The following compounds were prepared from the corresponding amine in a manner similar to that described for Example 87 using IPA to dilute the mixture. The precipitate was collected by suction filtration then dried under vacuum to give the desired products.

| Example | Structure | Mass Calc'd | Mass Obs. | Notes |
|---|---|---|---|---|
| 103 | $N^2$-(2-Naphthalenyl)-$N^4$-(6-quinolinyl)-2,4-pyrimidinediamine | 363 | 364 | tan solid |
| 104 | $N^2$-(3-(1,3-oxazol-5-yl)phenyl)-$N^4$-(3-quinolinyl)-2,4-pyrimidinediamine | 380 | 381 | Tan solid |
| 105 | $N^2$-(3-(1,3-oxazol-5-yl)phenyl)-$N^4$-(6-quinolinyl)-2,4-pyrimidinediamine | 380 | 381 | Tan solid |

| Example | Structure | Mass Calc'd | Mass Obs. | Notes |
|---|---|---|---|---|
| 106 | 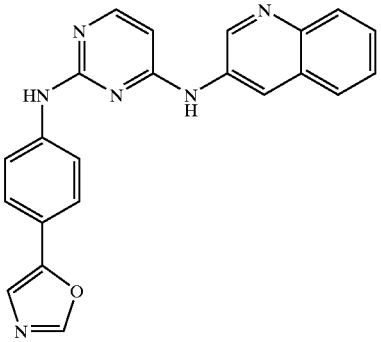<br>N²-(4-(1,3-oxazol-5-yl)phenyl)-N⁴-(3-quinolinyl)-2,4-pyrimidinediamine | 380 | 301 | Tan solid |
| 107 | 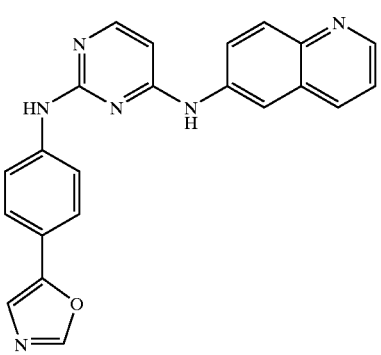<br>N²-(4-(1,3-oxazol-5-yl)phenyl)-N⁴-(6-quinolinyl)-2,4-pyrimidinediamine | 380 | 381 | Tan solid |
| 108 | 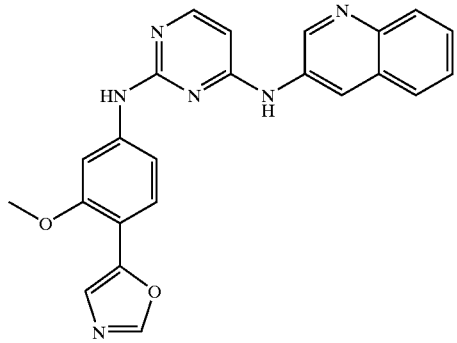<br>N²-(3-methoxy-4-(1,3-oxazol-5-yl)pheflyl)-N⁴-(3-quinoliflyl)-2,4-pyrimidinediamine | 410 | 411 | Tan solid |

-continued

| Example | Structure | Mass Calc'd | Mass Obs. | Notes |
|---------|-----------|-------------|-----------|-------|
| 109 | N²-(3-methoxy-4-(1,3-oxazol-5-yl)phenyl)-N⁴-(3-quinolinyl)-2,4-pyrimidinediamine | 410 | 411 | Colorless solid |
| 110 | N²-(1-acetyl-3,3-dimethyl-2,3-dihydro-1H-indol-6-yl)-N⁴-(3-quinolinyl)-2,4-pyrimidinediamine | 424 | 425 | Tan solid |
| 111 | N²-(1-acetyl-3,3-dimethyl-2,3-dihydro-1H-indol-6-yl)-N⁴-(6-quinolinyl)-2,4-pyrimidinediamine | 424 | 425 | Tan solid |

EXAMPLE 112

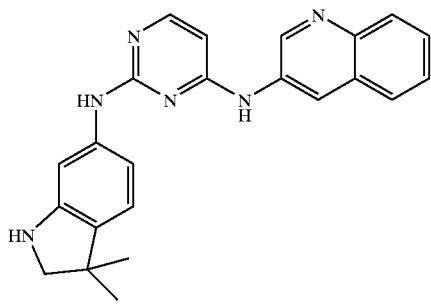

N²-(3,3-Dimethyl-2,3-dihydro-1H-indol-6-yl)-N⁴-(3-quinolinyl)-2,4-pyrimidinediamine A mixture of N²-(1-acetyl-3,3-dimethyl-2,3-dihydro-1H-indol-6-yl)-N⁴-(3-quinolinyl)-2,4-pyrimidinediamine (Example 110, 170 mg, 0.266 mmol) was dissolved in EtOH (6 mL) and 10 drops conc. HCl were added. The mixture was heated to reflux in a sealed tube for 72 h. The crude mixture was poured into EtOAc (125 mL) and sat NaHCO₃ (20 mL). The organics were dried over anhydrous MgSO₄ and concentrated under reduced pressure. The crude product was purified via medium pressure liquid chromatography using linear gradient starting from 0:100 MeOH/CH₂Cl₂ ending with 10:90 MeOH/CH₂Cl₂ as the solvent system to yield the desired product as a tan solid. M+H—383; Calc'd for $C_{23}H_{22}N_6$—382.

EXAMPLE 113

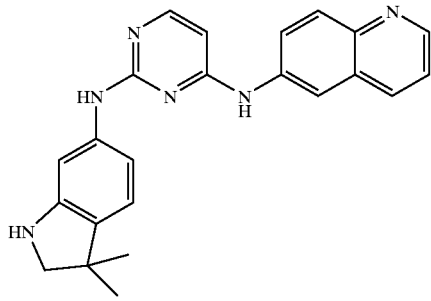

N²-(3,3-Dimethyl-2,3-dihydro-1H-indol-6-yl)-N⁴-(6-quinolinyl)-2,4-pyrimidinediamine A mixture of N²-(1-acetyl-3,3-dimethyl-2,3-dihydro-1H-indol-6-yl)-N⁴-(6-quinolinyl)-2,4-pyrimidinediamine (Example 111, 150 mg, 0.353 mmol) was dissolved in EtOH (6 mL) and 10 drops conc. HCl were added. The mixture was heated to reflux in a sealed tube for 72 h. The crude mixture was poured into EtOAc (125 mL) and sat NaHCO₃ (20 mL). The organics were dried over anhydrous MgSO₄ and concentrated under reduced pressure. The crude product was purified via medium pressure liquid chromatography using linear gradient starting from 0:100 MeOH/CH₂Cl₂ ending with 10:90 MeOH/CH₂Cl₂ as the solvent system to yield the desired product as a light yellow solid. M+H—383; Calc'd for $C_{23}H_{22}N_6$—382.

EXAMPLE 114

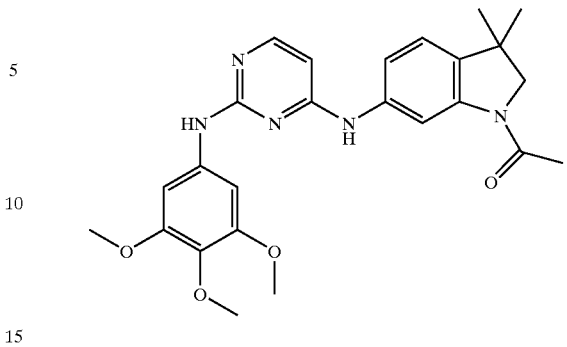

N⁴-(1-Acetyl-3,3-dimethyl-2,3-dihydro-1H-indol-6-yl)-N²-(3,4,5-tris(methoxy)phenyl)-2,4-pyrimidinediamine The compound was prepared from 1-[6-(2-chloro-pyrimidin-4-ylamino)-3,3-dimethyl-2,3-dihydro-indol-1-yl]-ethanone in a manner similar to that described above for Example 87. The crude mixture was poured into EtOAc (30 mL) and sat NaHCO₃ (10 mL). The organics were dried over anhydrous MgSO₄ and concentrated under reduced pressure. The crude was purified via medium pressure liquid chromatography using CH₂Cl₂ followed by 1:99 MeOH/CH₂Cl₂ followed 3:97 MeOH/CH₂Cl₂ as the solvent system to yield the desired product as a purple solid. M+H—464; Calc'd for $C_{25}H_{29}N_5O_4$—463.

EXAMPLE 115

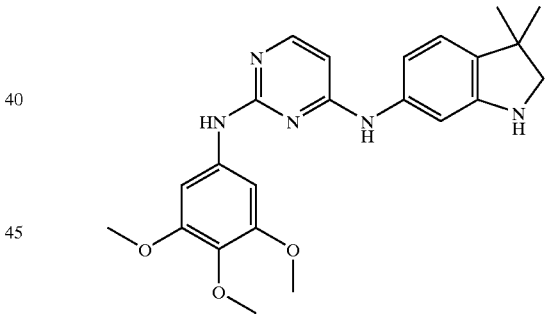

N⁴-(3,3-Dimethyl-2,3-dihydro-1H-indol-6-yl)-N²-(3,4,5-tris(methoxy)phenyl)-2,4-pyrimidinediamine A mixture of N⁴-(1-acetyl-3,3-dimethyl-2,3-dihydro-1H-indol-6-yl)-N²-(3,4,5-tris(methoxy)phenyl)-2,4-pyrimidinediamine (Example 114, 170 mg, 0.266 mmol) was dissolved in EtOH (6 mL) and 10 drops conc. HCl were added. The mixture was heated to reflux in a sealed tube for 72 h. The crude mixture was poured into EtOAc (125 mL) and sat NaHCO₃ (20 mL). The organics were dried over anhydrous MgSO₄ and concentrated under reduced pressure. The crude was purified via medium pressure liquid chromatography using linear gradient starting from 0:100 MeOH/CH₂Cl₂ ending with 10:90 MeOH/CH₂Cl₂ as the solvent system to provide the desired product as a purple solid. M+H—422; Calc'd for $C_{23}H_{27}N_5O_3$—421.

EXAMPLE 116

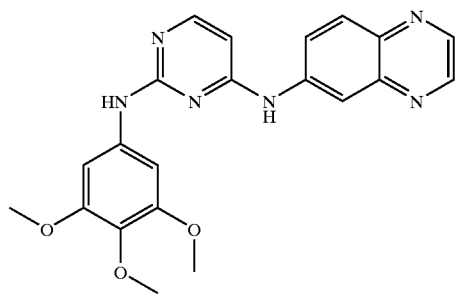

N$^4$-(6-Quinoxalinyl)-N$^2$-(3,4,5-tris(methoxy)phenyl)-2,4-pyrimidinediamine

The compound was prepared from the corresponding amine in a manner similar to that described for Example 87. The crude product was taken up in DMSO then purified via preparative HPLC to give the desired compound as a light yellow solid. M+H—405; Calc'd for C$_{21}$H$_{20}$N$_6$O$_3$—404.

EXAMPLE 117

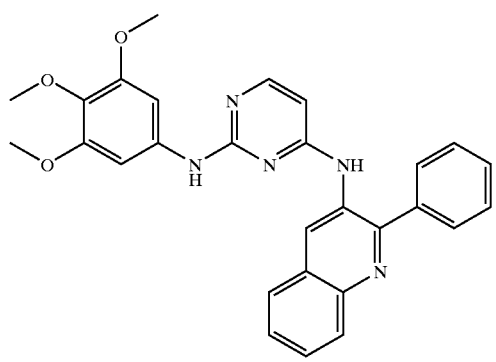

N$^4$-(2-Phenyl-3-quinolinyl)-N$^2$-(3,4,5-tris(methoxy)phenyl)-2,4-pyrimidinediamine The compound was prepared from the corresponding amine in a manner similar to that described for Example 87. The crude mixture was poured into EtOAc (200 mL) and sat NaHCO$_3$ (10 mL). The organics were dried over anhydrous MgSO$_4$ and concentrated under reduced pressure. The crude was purified via medium pressure liquid chromatography using 50:50 EtOAc/hexanes followed by 100% EtOAc as the solvent system. The desired product was obtained as an off-white solid. M+H—480; Calc'd for C$_{28}$H$_{25}$N$_5$O$_3$—479.

EXAMPLE 118

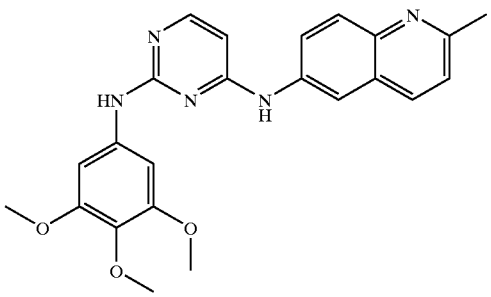

N$^4$-(2-Methyl-6-quinolinyl)-N$^2$-(3,4,5-tris(methoxy)phenyl)-2,4-pyrimidinediamine The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using CH$_2$Cl$_2$ followed by 1:99 MeOH/CH$_2$Cl$_2$ followed 3:97 MeOH/CH$_2$Cl$_2$ as the solvent system. The desired product was obtained as an off-white solid. M+H—418; Calc'd for C$_{23}$H$_{23}$N$_5$O$_3$—417.

EXAMPLE 119

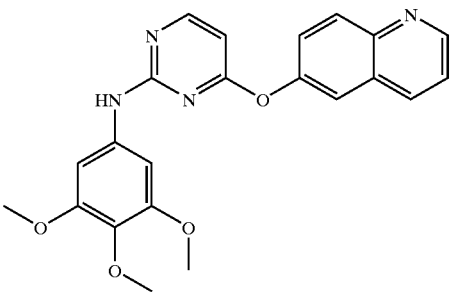

4-(6-Quinolinyloxy)-N-(3,4,5-tris(methoxy)phenyl)-2-pyrimidinamine

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via preparative HPLC to give the desired product as an off-white solid. M+H—405; Calc'd for C$_{22}$H$_{20}$N$_4$O$_4$—404.

EXAMPLE 120

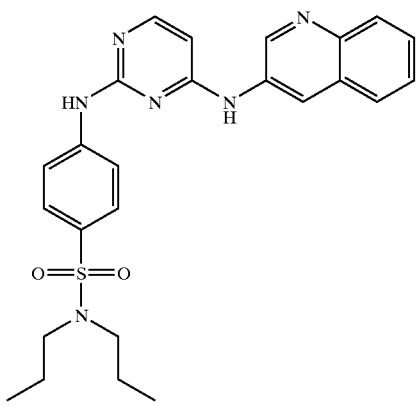

N,N-Dipropyl-4-((4-(3-quinolinylamino)-2-pyrimidinyl)amino)benzenesulfonamide

The compound was prepared from the corresponding amine in a manner similar to that described for Example 87. The crude mixture was poured into EtOAc (30 mL) and sat NaHCO$_3$ (10 mL). The organics were dried over anhydrous MgSO$_4$ and concentrated under reduced pressure. The crude was purified via medium pressure liquid chromatography using CH$_2$Cl$_2$ followed by 1:99 MeOH/CH$_2$Cl$_2$ followed 3:97 MeOH/CH$_2$Cl$_2$ as the solvent system. The desired product was obtained as a white solid. M+H—477; C$_{25}$H$_{28}$N$_6$O$_2$S—476.

EXAMPLE 121

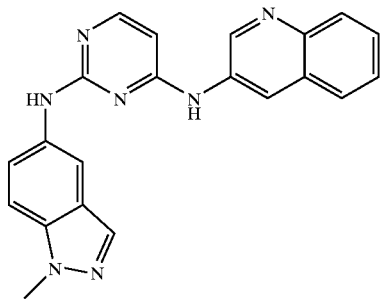

N$^2$-(1-Methyl-1H-indazol-5-yl)-N$^4$-quinolin-3-yl-pyrimidine-2,4-diamine

The title compound was prepared by the method described in Example 87 using the appropriate aniline reagent, which was prepared by the reduction of the corresponding nitro derivative (H$_2$, Pd/C, MeOH, EtOAc, EtOH). MS m/z=368.0. Calc'd for C$_{21}$H$_{17}$N$_7$: 367.

EXAMPLE 122

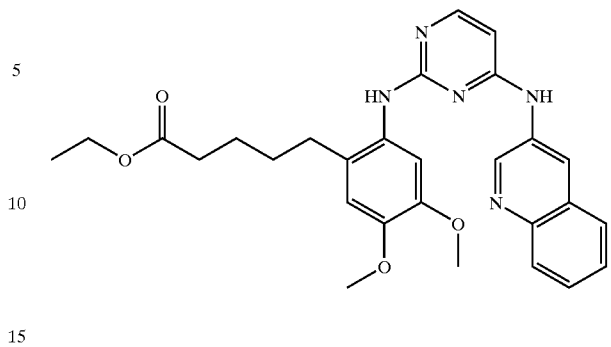

5-{4,5-Dimethoxy-2-[4-(quinolin-3-ylamino)-pyrimidin-2-ylamino]-phenyl}-pentanoic acid ethyl ester Step A: Preparation of 5-(4,5-dimethoxy-2-nitro-phenyl)-penta-2,4-dienoic acid ethyl ester.

To a suspension of NaH (0.24 g, 6.0 mmol) in THF (30 mL) at 0° C. was added a solution of triethyl 4-phosphonocrotonate (1.0 g, 4.0 mmol) in THF (5 mL) dropwise. The solution was warmed to RT and stirred for 1 h. Nitroveratraldehyde (0.844 g, 4.0 mmol) was added to the mixture in one portion and the reaction was stirred for an additional 30 min at RT. NH$_4$Cl (aq., sat., 3 mL) was added slowly to quench the reaction, followed by H$_2$O (30 mL). The THF solvent was removed under reduced pressure and the resulting mixture was extracted with EtOAc (3×10 mL). The organic extracts were combined, washed with brine, dried with MgSO$_4$ and filtered. The solvent was removed under reduced pressure and the mixture was purified by chromatography on silica gel to afford the title compound.

Step B: Preparation of 5-(2-amino-4,5-dimethoxy-phenyl)-pentanoic acid ethyl ester.

To a solution of 5-(4,5-dimethoxy-2-nitro-phenyl)-penta-2,4-dienoic acid ethyl ester (Step A, 0.5 g, 1.63 mmol) in EtOH (15 mL) at RT was added Pd/C (0.05 g). The flask was capped with a rubber septum and H$_2$ pressure was applied through a balloon/needle. The reaction was stirred at RT for 12 h, at which time the mixture was filtered through sand/Celite®. The solvent was removed under reduced pressure to afford the title compound.

Step C: Preparation of 5-{4,5-dimethoxy-2-[4-(quinolin-3-ylamino)-pyrimidin-2-ylamino]-phenyl}-pentanoic acid ethyl ester.

The title compound was prepared by the method described in Example 87 using 5-(2-amino-4,5-dimethoxy-phenyl)-pentanoic acid ethyl ester from Step B above. MS m/z=502.3. Calc'd for C$_{28}$H$_{31}$N$_5$O$_4$: 501.59.

EXAMPLE 123

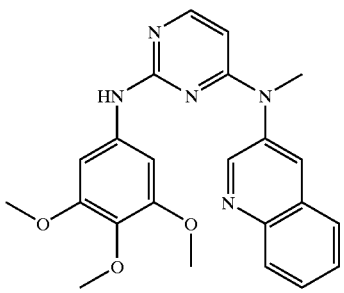

N⁴-Methyl-N⁴-quinolin-3-yl-N²-(3,4,5-trimethoxy-phenyl)-pyrimidine-2,4-diamine

Step A: Preparation of (2-chloro-pyrimidin-4-yl)-methyl-quinolin-3-yl-amine.

To a solution of (2-chloro-pyrimidin-4-yl)-quinolin-3-yl-amine (0.400 g, 1.64 mmol) in DMF (7 mL) at 0° C. was added MeI (0.133 mL, 2.13 mmol) and NaH (60% dispersion in mineral oil, 0.079 g, 1.97 mmol). The reaction mixture was warmed to RT, accompanied by the appearance of a yellow color and solid precipitate. After stirring for 1 h at RT, H₂O (25 mL) was added and the mixture was extracted with EtOAc (3×10 mL). The combined organic layers were washed with brine, dried with MgSO₄, filtered and concentrated under reduced pressure. Chromatography on silica gel (1:1 EtOAc:Hexanes) provided the title compound.

Step B: Preparation of N⁴-methyl-N⁴-quinolin-3-yl-N²-(3, 4,5-trimethoxy-phenyl)-pyrimidine-2,4-diamine The title compound was prepared by the method described in Example 87 using the appropriate aniline reagent. MS m/z=418.3. Calc'd for $C_{23}H_{23}N_5O_3$: 417.47.

The following compounds were prepared by a method similar to that described in Example 123.

| Example | Structure | Mass Calc'd | Mass Obs. |
|---|---|---|---|
| 124 | 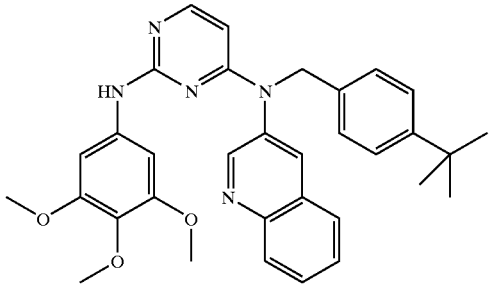<br>N⁴-(4-t-Butyl-benzyl)-N⁴-quinolin-3-yl-N²-(3,4,5-trimethoxy-phenyl)-pyrimidine-2,4-diamine | 549.68 | 550.5 |
| 125 | 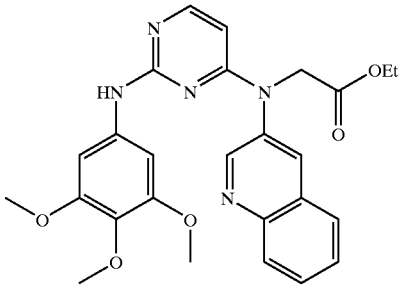<br>{Quinolin-3-yl-[2-(3,4,5-trimethoxy-phenylamino)-pyrimidin-4-yl]-amino}-acetic acid ethyl ester | 489.54 | 490.4 |

-continued
| Example | Structure | Mass Calc'd | Mass Obs. |
|---|---|---|---|
| 126 | 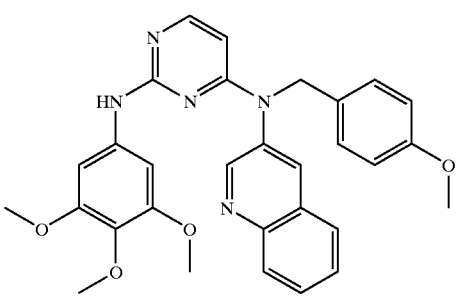 N4-(4-Methoxy-benzyl)-N4-quinolin-3-yl)-N2-(3,4,5-trimethoxy-phenyl)-pyrimidine-2,4-diamine | 523.60 | 524.5 |
| 127 | 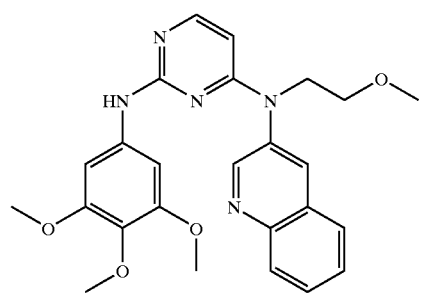 N4-(2-Methoxy-ethyl-N4-quinolin-3-yl-N2-(3,4,5-trimethoxy-phenyl)-pyrimidine-2,4-diamine | 461.53 | 462.5 |
| 128 | 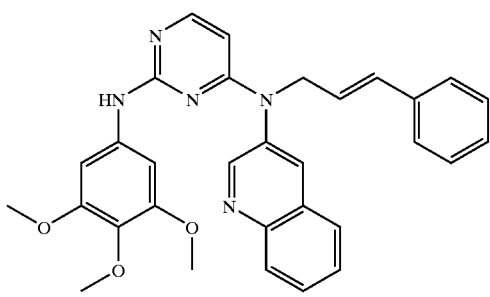 N4-(3-Phenyl-allyl)-N4-quinolin-3-yl-N2-(3,4,5-trimethoxy-phenyl)-pyrimidine-2,4-diamine | 519.61 | 520.4 |

| Example | Structure | Mass Calc'd | Mass Obs. |
| --- | --- | --- | --- |
| 129 | 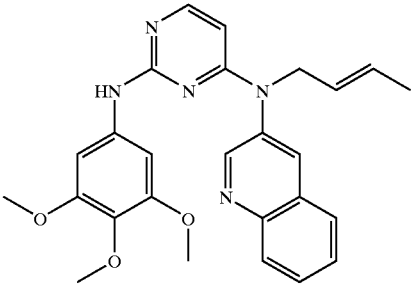<br>N⁴-But-2-enyl-N⁴-quinolin-3-yl)-N²-(3,4,5-trimethoxy-phenyl)-pyrimidine-2-4-diamine | 457.4 | 458.4 |

EXAMPLE 130

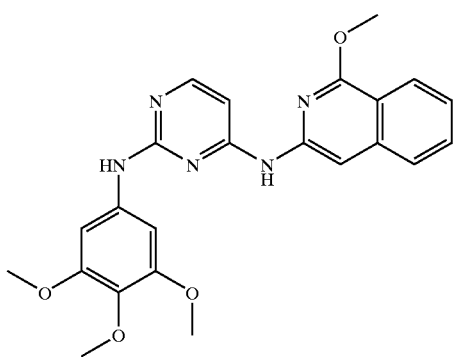

N⁴-(1-Methoxy-isoquinolin-3-yl)-N²-(3,4,5-trimethoxy-phenyl)-pyrimidine-2,4-diamine The title compound was prepared by the method described in Example 87 using the appropriate aniline reagent. MS m/z=434.2. Calc'd for $C_{23}H_{23}N_5O_4$: 433.47.

EXAMPLE 131

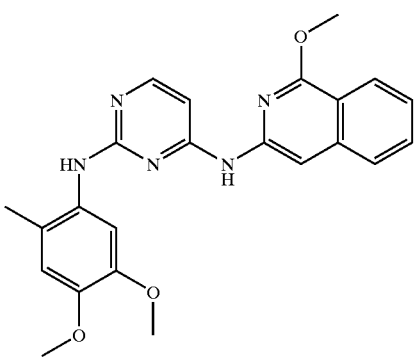

N²-(4,5-Dimethoxy-2-methyl-phenyl)-N⁴-(1-methoxy-isoquinolin-3-yl)-pyrimidine-2,4-diamine The title compound was prepared by the method described in Example 87 using the appropriate aniline reagent. MS m/z=418.2. Calc'd for $C_{23}H_{23}N_5O_3$: 417.47.

EXAMPLE 132

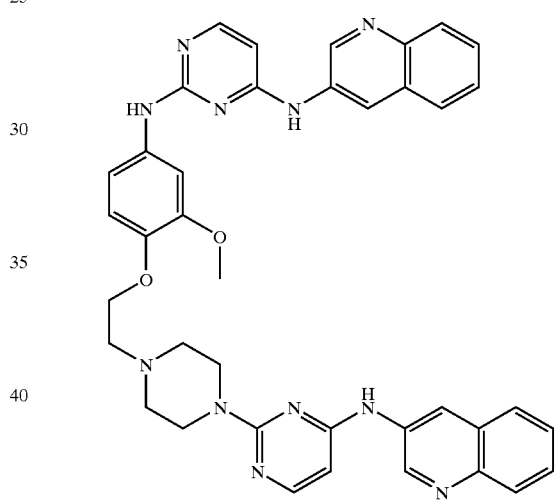

N²-[3-Methoxy-4-(2-{4-[4-(quinolin-3-ylamino)-pyrimidin-2-yl]-piperazin-1-yl}-ethoxy)-phenyl]-N⁴-quinolin-3-yl-pyrimidine-2,4-diamine Step A To a solution of 10 g (48.3 mmol) of 4-nitroguiacol in 500 mL of CH₃CN was added 16.7 g (121 mmol) of K₂CO₃. The resulting mixture was stirred at 20° C. for 10 min then 40.2 mL (483 mmol) of 1-bromo-2-chloroethane was added. The resulting mixture was heated at 80° C. overnight. The reaction was filtered and the solid was washed with CH₃CN and dried, giving 1-(2-chloroethoxy)-2-methoxy-4-nitrobenzene as a yellow solid.

Step B

A mixture of 1-(2-chloroethoxy)-2-methoxy-4-nitrobenzene (Step A, 1 eq), N-methylpiperazine (3 eq) and K₂CO₃ (2.5 eq) in CH₃CN was stirred and heated under reflux until HPLC indicated the reaction was complete. The resulting solid was filtered, rinsed well with CH₂Cl₂ and the filtrate and washings were combined, concentrated and purified by column chromatography giving 1-[2-(2-methoxy-4-nitro-phenoxy)-ethyl]-4-methyl-piperazine.

Step C

1-[2-(2-Methoxy-4-nitro-phenoxy)-ethyl]-4-methyl-piperazine (Step B) was converted into 3-methoxy-4-[2-(4-methyl-piperazin-1-yl)-ethoxy]-phenylamine by standard catalytic hydrogenation.

Step D

The title compound was prepared by the method described in Example 87 using 3-methoxy-4-[2-(4-methyl-piperazin-1-yl)-ethoxy]-phenylamine (Step C). MS m/z= 693.0. Calc'd for $C_{39}H_{37}N_{11}O_2$: 691.80.

EXAMPLE 133

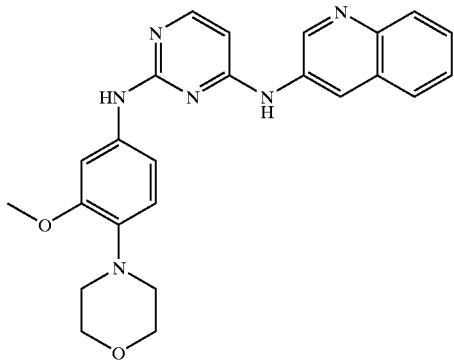

$N^2$-(3-Methoxy-4-morpholin-4-yl-phenyl)-$N^4$-quinolin-3-yl-pyrimidine-2,4-diamine Step A: Preparation of 4-(2-methoxy-4-nitro-phenyl)-morpholine To a mixture of 1-bromo-2-methoxy-4-nitro-benzene (2.5 g, 10.8 mmol), $Pd_2(dba)_3$ (0.124 g, 0.215 mmol), NaOt-Bu (1.55 g, 16.2 mmol) and BINAP (0.202 g, 0.323 mmol) in toluene (20 mL) at 20° C. was added morpholine (1.5 mL, 17.2 mmol) over 10 min. The mixture was stirred at 80° C. for 3 h when TLC indicated no starting material remained. The mixture was evaporated under reduced pressure followed by the addition of $H_2O$ (50 mL). $CH_2Cl_2$ extraction (3×15 mL), followed by drying of the combined organic layers with $MgSO_4$ afforded, after filtration and concentration, an orange oil. Chromatography on silica gel (97:3 $CH_2Cl_2$/MeOH) yielded pure compound.

Step B: Preparation of 3-methoxy-4-morpholin-4-yl-phenylamine

To a solution of 4-(2-methoxy-4-nitro-phenyl)-morpholine (Step A, 1.0 g, 4.2 mmol) in EtOH (25 mL) at 20° C. was added Pd/C (100 mg). The flask was capped with a rubber septum and $H_2$ pressure applied through a balloon/needle. The reaction was stirred at 20° C. for 12 h, filtered through sand/Celite® and concentrated. Purification by chromatography of the crude mixture (97:3 $CH_2Cl_2$:MeOH) afforded 3-methoxy-4-morpholin-4-yl-phenylamine as a purple solid.

Step C: Preparation of $N^2$-(3-methoxy-4-morpholin-4-yl-phenyl)-$N^4$-quinolin-3-yl-pyrimidine-2,4-diamine The title compound was prepared by the method described in Example 87 using 3-methoxy-4-morpholin-4-yl-phenylamine (Step B). MS m/z=429.3. Calc'd for $C_{24}H_{24}N_6O_2$: 428.50.

EXAMPLE 134

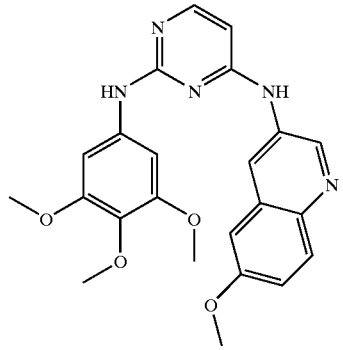

$N^4$-(6-Methoxy-quinolin-3-yl)-$N^2$-(3,4,5-tris(methoxy)phenyl)-2,4-pyrimidinediamine Step A A mixture of p-methoxyaniline (35 g, 0.28 mol) and diethyl ethoxymethylene malonate (74 g, 0.34 mol) was stirred 2 h at 100° C. under reduce pressure. The crude 6-methoxy-4-hydroxy-3-ethoxycarbonylquinoline was used in the next step without further purification.

Step B

To a stirred solution of the crude 6-methoxy-4-hydroxy-3-ethoxycarbonylquinoline (Step A, 74 g, 0.25 M) in dry toluene (300 mL) was added $POCl_3$ (46.6 mL, 0.5 mol) followed by $PCl_5$ (26 g, 0.125 mol). The mixture was heated at reflux for 6 h. The toluene and the excess of $POCl_3$ were removed under vacuum. The solid residue was suspended into a mixture of 1N NaOH and ice. The resulting solid was filtered off, washed several times with water, then with a minimum amount of MeOH, and dried over $P_2O_5$ to give 6-methoxy-4-chloro-3-ethoxycarbonylquinoline as a white solid.

Step C

To a suspension of 6-methoxy-4-chloro-3-ethoxycarbonyl-quinoline (Step B, 20 g, 0.075 mol) in 1/1 EtOAc/AcOH (560 mL) in a Parr hydrogenation apparatus bottle kept under inert atmosphere was added Pt/C 10% (2 g). The mixture was hydrogenated under 60 psi hydrogen at RT for 2 h using a Parr hydrogenation apparatus. The resulting mixture was diluted with MeOH and filtered. The solid was washed several times with a 1/1 MeOH/$CH_2Cl_2$ mixture and the solvents were removed under vacuum. The resulting solid was suspended into $CH_2Cl_2$ and 2N NaOH was added. The mixture was stirred at RT for 30 min. The organic layer was recovered and washed once with 2 N NaOH and twice with water to give crude 6-methoxy-3-ethoxycarbonyl-1,2,3,4-tetrahydroquinoline, which was directly used in the next step.

Step D

To a stirred solution of 6-methoxy-3-carboxyethyl-1,2,3,4-tetrahydroquinoline (Step C, 17.6 g, 0.074 mol) in $CH_2Cl_2$ (330 mL) cooled at 5° C., was added DDQ (42.2 g, 0.186 mol) portion-wise. The reaction was stirred at RT for 2 h, then diluted with MTBE (600 mL), washed twice with 1N NaOH and twice with water. Flash chromatography in 20% EtOAc/Hexane yielded 6-methoxy-3-ethoxycarbonylquinoline.

Step E

To a stirred solution of 6-methoxy-3-ethoxycarbonylquinoline (Step D, 6 g, 0.026 mol) in EtOH (65 mL) was added at RT a 2N aqueous solution of NaOH (26 mL, 0.052 mol). The reaction mixture was stirred at RT overnight. After concentration under vacuum, the mixture was acidified with 1N HCl and the resulting solid was filtered off, washed with water and dried over $P_2O_5$ to give 6-methoxy-3-carboxyquinoline.

Step F

To a stirred suspension of 6-methoxy-3-carboxyaminoquinoline (Step E, 4.8 g, 0.021 mol) in toluene (109 mL) was added DPPA (5.83 mL, 0.026 mol) followed by TEA (3.6 mL, 0.026 mol). The reaction was stirred at RT for 30 min. t-BuOH (8.22 mL, 0.086 mL) was added then the mixture was heated at reflux for 8 h. The solution was diluted with EtOAc and washed 2× with a saturated solution of $NH_4Cl$ and 2× with water. The EtOAc solution was dried over $MgSO_4$ and evaporated. The mixture was purified by flash chromatography using 20% EtOAc/hexane to give N-tert-butyloxycarbonyl-6-methoxy-3-aminoquinoline.

Step G

To a stirred solution of N-tert-butyloxycarbonyl-6-methoxy-3-aminoquinoline (Step F, 3 g, 0.011 mol) in $CH_2Cl_2$ (50 mL) cooled at 0° C. was added TFA (8.4 mL, 0.11 mL). The reaction mixture was warmed to RT and stirred for 8 h. The reaction mixture was concentrated under vacuum. The residue was suspended into MTBE. The yellow solid was filtered off and washed with MTBE. The dry yellow solid was suspended in NaOH 1N and the suspension was stirred for 15 min. The resulting slurry was filtered. The solid was washed with water and dried over $P_2O_5$ to give 6-methoxy-3-aminoquinoline as a white solid.

Step H

The 6-methoxy-3-aminoquinoline (Step G) was coupled to the 2,4-dichloropyridine using the general procedure described in Procedure A to afford 2-chloro-4-(6-methoxy-3-aminoquinolino)-1,3-pyrimidine as a brownish solid.

Step I

The title compound was prepared by the method described in Example 65 using 2-chloro-4-(6-methoxy-3-aminoquinolino)-1,3-pyrimidine and 3,4,5-trimethoxyaniline. MS (MH$^+$)=434.2, MW: 433.47 Calculated for: $C_{23}H_{23}N_5O_4$.

EXAMPLE 135

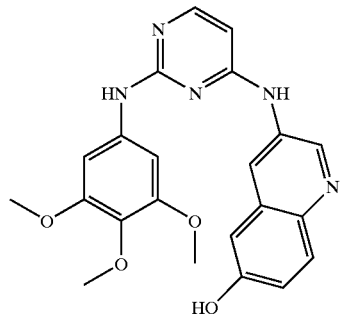

$N^4$-(6-Hydroxy-quinolin-3-yl)-$N^2$-(3,4,5-tris(methoxy)phenyl)-2,4-pyrimidinediamine Step A A stirred suspension of N-tert-butyloxycarbonyl-6-methoxy-3-aminoquinoline (Example 134, Step F) (0.274 g, 1 mmol) in HBr (48%, 2.5 mL) was heated at reflux for 48 h. The reaction was cooled to 0° C., and the yellow crystalline solid was filtered off and washed with a small amount of ice-cold water followed by acetone. The yellow crystalline solid was dried over $P_2O_5$ to give 6-hydroxy-3-aminoquinoline di-hydrobromide.

Step B

A mixture of 6-hydroxy-3-aminoquinoline di-hydrobromide (Step A, 0.064 g, 0.2 mmol), 2,4-dichloropyrimidine (0.036 g, 0.24 mmol) and DIEA (0.157 mL, 0.9 mmol) in IPA (1 mL) was heated at reflux over night. The reaction was cooled to RT and a yellow solid was filtered off and washed with IPA. The IPA solution was concentrated under vacuum and the residue was purified by flash chromatography in $CH_2Cl_2$/MeOH/$NH_4OH$. The less polar fractions were combined and solvents removed under vacuum. The residue was suspended in MeOH. The solid was filtered off and washed with MeOH to give 2-chloro-4-(6-hydroxy-3-aminoquinolino)-1,3-pyrimidine as a pale yellow solid.

Step C

The title compound was prepared by the method described in Example 65 using 2-chloro-4-(6-hydroxy-3-aminoquinolino)-1,3-pyrimidine (Step B) and 3,4,5-trimethoxyaniline. MS (MH$^+$)=420.1, MW: 419.44 Calculated for: $C_{22}H_{21}N_5O_4$.

EXAMPLE 136

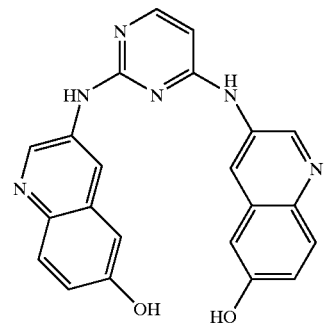

$N^2,N^4$-bis(6-Hydroxy-3-quinolinyl)-2,4-pyrimidinediamine

A mixture of 6-hydroxy-3-aminoquinoline di-hydrobromide (0.064 g, 0.2 mmol) and 2,4-dichloropyrimidine (0.148 g, 1 mmol) in IPA (1 mL) was heated at reflux overnight. The reaction was cooled to RT and a yellow solid was filtered off and washed with IPA. The solid was purified by flash chromatography in $CH_2Cl_2$/MeOH/$NH_4OH$ (90/10/1). The fractions containing the compound were combined and the solvents were removed under vacuum. The residue was purified by reverse-phase preparative HPLC ($CH_3CN$/water/TFA) to give the bis-trifluoroacetate of the title compound as a yellow solid. MS (MH$^+$)=397.2, Calc'd for: $C_{22}H_{16}N_6O_2$—396.4.

EXAMPLE 137

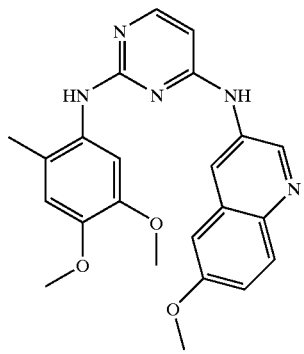

N⁴-(6-Methoxy-3-quinolinyl)-N²-(2-methyl-4,5-dimethoxyphenyl)-2,4-pyrimidinediamine The title compound was prepared by the method described in Example 65 using 2-chloro-4-(6-methoxy-3-aminoquinolino)-1,3-pyrimidine (Example 134 Step H) and 2-methyl-4,5-dimethoxyaniline. MS (MH⁺)=418.2; Calc'd for $C_{23}H_{23}N_5O_3$—417.47.

EXAMPLE 138

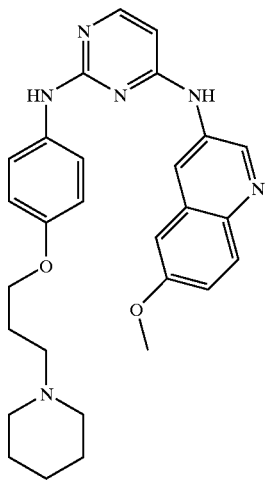

N⁴-(6-Methoxy-3-quinolinyl)-N²-[4-(3-(piperidin-1-yl)-propoxy)phenyl]-2,4-pyrimidinediamine The title compound was prepared by the method described in Example 65 using 2-chloro-4-(6-methoxy-3-aminoquinolino)-1,3-pyrimidine (Example 134 Step H) and 3-(piperidin-1-yl)-propoxy)aniline. MS (MH⁺)=485.4; Calc'd for $C_{28}H_{32}N_6O_2$—484.61.

EXAMPLE 139

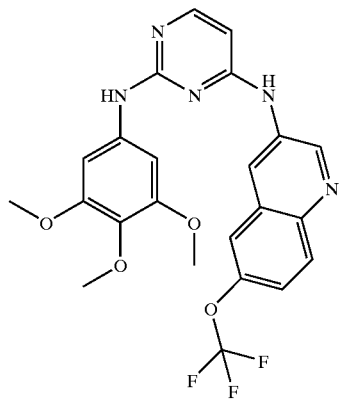

N²-(3,4,5-Tris(methoxy)phenyl)-N⁴-(6-trifluoromethoxy-3-quinolinyl)-2,4-pyrimidinediamine Step A 6-Trifluoromethoxy-4-hydroxy-3-ethoxycarbonylquinoline (3 g, 10 mmol) and POCl₃ (8 mL) were mixed together and the mixture was heated at reflux for 6 h. The excess POCl₃ was removed under vacuum. The solid residue was suspended in ice-cold 1N NaOH and the mixture was stirred for 15 min. The solid was filtered off, washed several times with water and dried over P₂O₅ to give 6-trifluoromethoxy-4-chloro-3-ethoxycarbonylquinoline as an off-white solid.

Steps B–F

6-Trifluoromethoxy-3-aminoquinoline was prepared from 6-trifluoromethoxy-4-chloro-3-ethoxycarbonylquinoline (Step A) following the general procedure described in Example 134 (steps C to C).

Step G

6-Trifluoromethoxy-3-aminoquinoline (Step F) was coupled to 2,4-dichloropyridine using the general procedure described in Procedure A to afford 2-chloro-4-(6-trifluoromethoxy-3-aminoquinolino)-1,3-pyrimidine as an off white solid.

Step H

The title compound was prepared by the method described in Example 65 using 2-chloro-4-(6-trifluoromethoxy-3-aminoquinolino)-1,3-pyrimidine (Step G) and 3,4,5-trimethoxyaniline. MS (MH⁺)=488.1; Calc'd for $C_{23}H_{20}F_3N_5O_4$— 487.44.

EXAMPLE 140

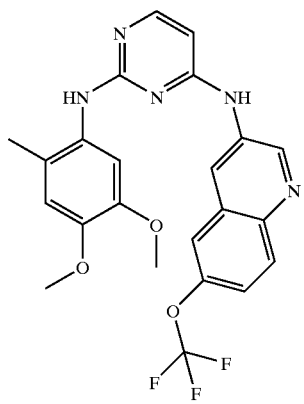

$N^2$-(2-Methyl-4,5-dimethoxyphenyl)-$N^4$-(6-trifluoromethoxy-3-quinolinyl)-2,4-pyrimidinediamine The title compound was prepared by the method described in Example 65 using 2-chloro-4-(6-trifluoromethoxy-3-aminoquinolino)-1,3-pyrimidine (Example 139 Step G) and 2-methyl-4,5-dimethoxyaniline. MS (MH$^+$)=472.1, MW: 471.44 Calc'd for $C_{23}H_{20}F_3N_5O_3$.

EXAMPLE 141

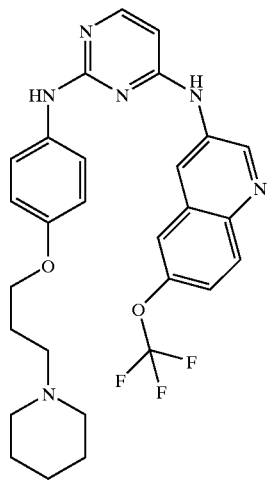

$N^2$-[4-(3-(Piperidin-1-yl)-propoxy)phenyl]-$N^4$-(6-trifluoromethoxy-3-quinolinyl)-2,4-pyrimidinediamine The title compound was prepared by the method described in Example 65 using 2-chloro-4-(6-trifluoromethoxy-3-aminoquinolino)-1,3-pyrimidine (Example 139 Step G) and 3-(piperidin-1-yl)-propoxy) aniline. MS (MH$^+$)=539.3, MW: 538.58 Calc'd for $C_{28}H_{29}F_3N_6O_2$.

EXAMPLE 142

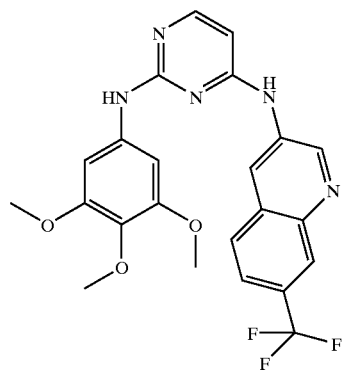

$N^2$-(3,4,5-Tris(methoxy)phenyl)-N-4-(7-trifluoromethyl-3-quinolinyl)-2,4-pyrimidinediamine Steps A, B, C, D, E, F 7-Trifluoromethyl-3-aminoquinoline was prepared from 7-trifluoromethyl-4-hydroxy-3-ethoxycarbonylquinoline following the general procedure described in Example 139 (steps A to F).

Step G

7-Trifluoromethyl-3-aminoquinoline was coupled to 2,4-dichloropyridine using the general procedure described in Procedure A to afford 2-chloro-4-(7-trifluoromethyl-3-aminoquinolino)-1,3-pyrimidine as an off white solid.

Step H

The title compound was prepared by the method described in Example 65 using 2-chloro-4-(7-trifluoromethyl-3-aminoquinolino)-1,3-pyrimidine (Step G) and 3,4,5-trimethoxyaniline. MS (MH$^+$)=472.1, MW: 471.44 Calculated for $C_{23}H_{20}F_3N_5O_3$.

EXAMPLE 143

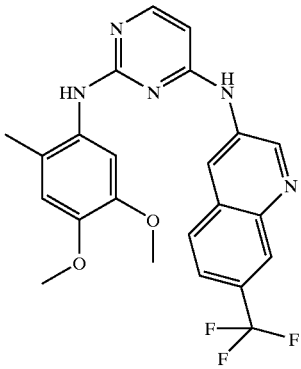

$N^2$-(2-Methyl-4,5-dimethoxyphenyl)-$N^4$-(7-trifluoromethyl-3-quinolinyl)-2,4-pyrimidinediamine The title compound was prepared by the method described in Example 65 using 2-chloro-4-(7-trifluoromethyl-3-aminoquinolino)-1,3-pyrimidine (Example 142 Step G) and 2-methyl-4,5-dimethoxyaniline. MS (MH$^+$)=456.1, MW: 455.44 Calc'd for $C_{23}H_{20}F_3N_5O_2$.

EXAMPLE 144

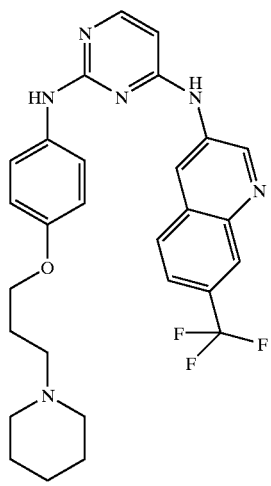

N²-[4-(3-(Piperidin-1-yl)-propoxy)phenyl]-N⁴-(7-trifluoromethyl-3-quinolinyl)-2,4-pyrimidinediamine The title compound was prepared by the method described in Example 65 using 2-chloro-4-(7-trifluorometyl-3-aminoquinolino)-1,3-pyrimidine (Example 142 Step G) and 3-(piperidin-1-yl)-propoxy)aniline. MS (MH⁺)=523.0, MW: 522.58 Calculated for $C_{28}H_{29}F_3N_6O$.

EXAMPLE 145

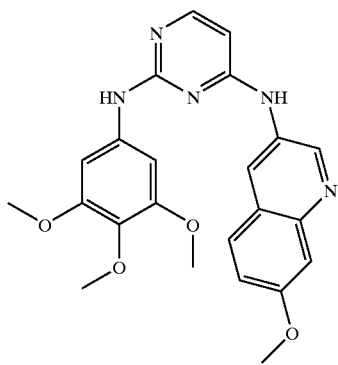

N²-(3,4,5-Tris(methoxy)phenyl)-N⁴-(7-methoxy-3-quinolinyl)-2,4-pyrimidinediamine

Step A

A mixture of m-methoxyaniline (35 g, 0.28 mol) and diethyl ethoxymethylene malonate (74 g, 0.34 mol) was stirred 2 h at 110° C. under reduce pressure. The mixture was heated at 240° C. under reduced pressure for an additional 2 h. The resulting solid was suspended in $CH_2Cl_2$, filtered off and washed with $CH_2Cl_2$ to yield 7-methoxy-4-hydroxy-3-ethoxycarbonylquinoline as a white solid.

Step B

7-Methoxy-4-hydroxy-3-ethoxycarbonylquinoline (Step A, 21 g, 0.08 mol) and $POCl_3$ (100 mL) were mixed together and the mixture was heated at reflux for 6 h. The excess $POCl_3$ was removed under vacuum. The solid residue was suspended in ice-cold 1N NaOH and the mixture was stirred for 15 min. The solid was filtered off, washed several times with water and then by a minimum amount of MeOH to give 7-methoxy-4-chloro-3-ethoxycarbonylquinoline as an off-white solid.

Step C

To a stirred suspension of 7-methoxy-4-chloro-3-ethoxycarbonylquinoline (Step B, 1.53 g, 5 mmol) in EtOH (15 mL) under inert atmosphere was added Pd/C 10% (153 mg). The mixture was stirred at RT under $H_2$ (atmospheric pressure) for 2 h. The mixture was filtered and solvent removed under vacuum to give crude 7-methoxy-3-ethoxycarbonylquinoline hydrochloride.

Step D

To a stirred solution of 7-methoxy-3-ethoxycarbonylquinoline hydrochloride (Step C, 1.45 g, 5.4 mmol) in EtOH (24 mL) was added at RT 2N NaOH (8 mL, 16 mmol). The reaction was stirred at RT overnight. After concentration under vacuum, the mixture was acidified with 1N HCl. The resulting solid was filtered off, washed with water and dried over $P_2O_5$ to give 7-methoxy-3-carboxyquinoline.

Steps E, F

7-Methoxy-3-aminoquinoline was prepared from 7-methoxy-3-carboxyquinoline (Step D) following the general procedure described for the synthesis of Example 134 (steps F and G).

Step G

7-Methoxy-3-aminoquinoline (Step F) was coupled to the 2,4-dichloropyridine using the general procedure described in Procedure A to afford 2-chloro-4-(7-methoxy-3-aminoquinolino)-1,3-pyrimidine as an off white solid.

Step H

The title compound was prepared by the method described in Example 65 using 2-chloro-4-(7-methoxy-3-aminoquinolino)-1,3-pyrimidine (Step G) and 3,4,5-trimethoxyaniline. MS (MH⁺)=434.1, MW: 433.47 Calculated for $C_{23}H_{23}N_5O_4$.

EXAMPLE 146

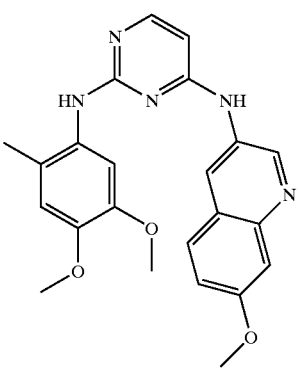

N²-(2-Methyl-4,5-dimethoxyphenyl)-N⁴-(7-methoxy-3-quinolinyl)-2,4-pyrimidinediamine The title compound was prepared by the method described in Example 65 using 2-chloro-4-(7-methoxy-3-aminoquinolino)-1,3-pyrimidine (Example 145 Step G) and 2-methyl-4,5-dimethoxyaniline. MS (MH⁺)=418.1, MW: 417.47 Calculated for $C_{23}H_{23}N_5O_3$.

EXAMPLE 147

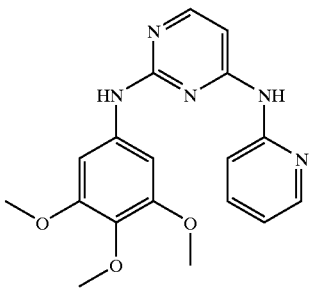

N⁴-Pyridin-2-yl-N²-(3,4,5-trimethoxy-phenyl)-pyrimidine-2,4-diamine

Step A

To a N₂ purged sealed tube, 2,4-dichloropyrimidine (1.0 g, 6.7 mmol, 1.2 eq.) and 2-aminopyridine (0.53 g, 5.6 mmol, 1.0 eq.) were added followed by 7 mL of anhydrous IPA. To the resulting suspension DIEA (0.98 mL, 5.6 mmol, 1.0 eq.) was added. The reaction was heated to 90–100° C. and stirred for 12 h. The reaction mixture was cooled to RT and the solvent was removed. The crude mixture was further purified by column chromatography (0–20% EtOAc in hexanes) providing pure (2-chloro-pyrimidin-4-yl)-pyridin-2-yl-amine.

Step B

To a mixture of (2-chloro-pyrimidin-4-yl)-pyridin-2-yl-amine (Step A, 50 mg, 0.24 mmol, 1.0 eq.) and trimethoxyaniline (53 mg, 0.29 mmol, 1.2 eq.) in DMSO (0.1 mL), 20 µl of a 1/1 (v/v) mixture of TFA/Et₃N was added. The reaction was heated to 90° C. for 2 h. The crude was purified by column chromatography (0–80% EtOAc in hexanes). The obtained oil was dissolved in a little MeOH, and water was slowly added. The resulting solids were filtered to give the title compound. MS m/z=354.3 (M+H)⁺ Calc'd for $C_{18}H_{19}N_5O_3$: 353.38.

EXAMPLE 148

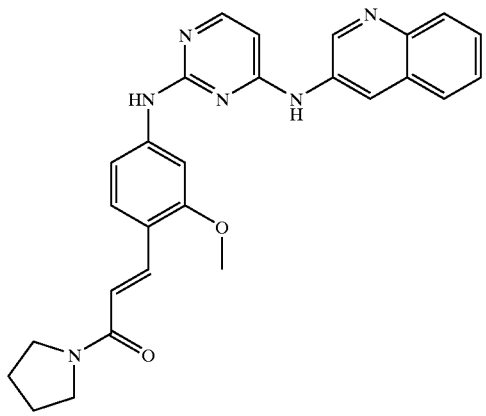

3-{2-Methoxy-4-[4-(quinolin-3-ylamino)-pyrimidin-2-ylamino]-phenyl}-1-pyrrolidin-1-yl-propenone Step A To a mixture of 2-iodo-5-nitroanisole (10 g, 36 mmol, 1.0 eq.) and 1-pyrrolidin-1-yl-propenone (6.3 g, 47 mmol, 1.3 eq.) in 100 mL of anhydrous toluene was added 10 mL of Et₃N followed by Pd(PPh₃)₄ (830 mg, 0.72 mol, 0.02 eq.) and Pd(OAc)₂ (80 mg, 0.36 mmol, 0.01 eq.). The mixture was degassed (3 times) using N₂, then heated to 120° C. and stirred for 16 h. The mixture was cooled to RT, filtered and concentrated. The resulting crude material was purified by column chromatography (20–100% EtOAc in hexanes) to obtain pure 3-(4-nitro-2-methoxy-phenyl)-1-pyrrolidin-1-yl-propenone.

Step B 3-(4-Nitro-2-methoxy-phenyl)-1-pyrrolidin-1-yl-propenone (1.0 g, 3.6 mmol, 1.0 eq., Step A) was suspended in 20 mL of MeOH and 10 mL of EtOH. The atmosphere was replaced with N₂ (3 times) and a catalytic amount of Pd/C was added. The N₂ was replaced by H₂ (3 times) and the reaction was stirred at balloon pressure for 16 h. 1,4-Dioxane (20 mL) was added (suspension becomes a solution) and more Pd/C was added. The mixture was stirred at RT and balloon pressure for another 16 h., filtered and concentrated. The crude was purified by column chromatography to give 3-(4-amino-2-methoxy-phenyl)-1-pyrrolidin-1-yl-propenone.

Step C

To a solution of (2-chloro-pyrimidin-4-yl)-quinolin-3-yl-amine (155 mg, 0.6 mmol, 1.0 eq.) and 3-(4-amino-2-methoxy-phenyl)-1-pyrrolidin-1-yl-propenone (Step B, 164 mg, 0.66 mmol, 1.1 eq.) in 0.5 mL of DMSO was added a 1/1 (v/v) mixture of TFA/Et₃N (123 µl, 0.66 mmol, 1.1 eq.). The reaction was heated to 100° C. and stirred for 16 h. The mixture was cooled and purified by column chromatography to provide the title compound. MS m/z=467.4 (M+H)⁺ Calc'd for $C_{27}H_{26}N_6O_2$: 466.55.

EXAMPLE 149

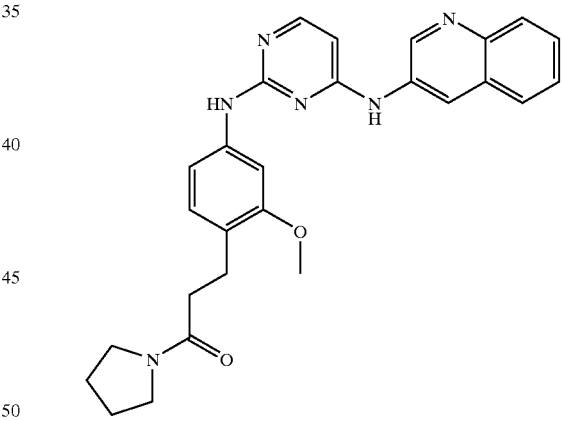

3-{2-Methoxy-4-[4-(quinolin-3-ylamino)-pyrimidin-2-ylamino]-phenyl}-1-pyrrolidin-1-yl-propanone Step A To a mixture of 2-iodo-5-nitroanisole (10 g, 36 mmol, 1.0 eq.) and 1-pyrrolidin-1-yl-propenone (6.3 g, 47 mmol, 1.3 eq.) in 100 mL of anhydrous toluene was added 10 mL of Et₃N followed by Pd(PPh₃)₄ (830 mg, 0.72 mol, 0.02 eq.) and Pd(OAc)₂ (80 mg, 0.36 mmol, 0.01 eq.). The mixture was degassed (3 times) using N₂. The mixture was heated to 120° C. and stirred for 16 h, cooled to RT, filtered and concentrated. The resulting crude material was purified by column chromatography (20–100% EtOAc in hexanes) to obtain pure 3-(4-nitro-2-methoxy-phenyl)-1-pyrrolidin-1-yl-propenone.

Step B 3-(4-Nitro-2-methoxy-phenyl)-1-pyrrolidin-1-yl-propenone (Step A, 3.5 g, 1.7 mmol, 1.0 eq.) was suspended in 20 mL of 1,4-dioxane and 40 mL of IPA. The atmosphere was replaced with $N_2$ (3 times) and a catalytic amount of Pd/C was added. The $N_2$ was replaced by $H_2$ (3 times) and the reaction mixture was stirred at 60 psi for 16 h. Filtered and concentrated to give pure 3-(4-amino-2-methoxy-phenyl)-1-pyrrolidin-1-yl-propan-1-one.

Step C

To a solution of (2-chloro-pyrimidin-4-yl)-quinolin-3-yl-amine (0.5 g, 1.8 mmol, 1.0 eq.) and 3-(4-amino-2-methoxy-phenyl)-1-pyrrolidin-1-yl-propan-1-one (0.47 g, 2.0 mmol, 1.1 eq. Step B) in 0.5 mL of DMSO was added a 1/1 (v/v) mixture of $TFA/Et_3N$ (337 µl, 1.8 mmol, 1.0 eq.). The reaction was heated to 100° C. and stirred for 16 h. The mixture was cooled, concentrated and purified by column chromatography (0–5% MeOH in $CH_2Cl_2$ with 1% of $NH_4OH$ (aq.)). Triturated with $CH_2Cl_2$ to provide the title compound. MS m/z=469.6 $(M+H)^+$ Calc'd for $C_{27}H_{28}N_6O_2$: 468.56.

EXAMPLE 150

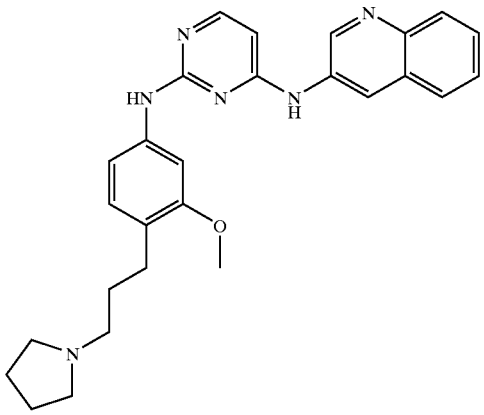

$N^2$-[3-Methoxy-4-(3-pyrrolidin-1-yl-propyl)-phenyl]-N-4-quinolin-3-yl-pyrimidine-2,4-diamine To a solution of 3-{2-methoxy-4-[4-(quinolin-3-ylamino)-pyrimidin-2-ylamino]-phenyl}-1-pyrrolidin-1-yl-propanone (Example 149) (0.1 g, 0.21 mmol, 1.0 eq.) in 5 mL of anhydrous THF was added LAH (22 mg, 6.0 mmol, 3.0 eq.). The reaction was heated to 80° C. and stirred 4 h. The mixture was cooled to RT, then 0° C. $H_2O$ (12 µl), 10% NaOH (aq., 21 µl) and $H_2O$ (33 µl) were added and stirred for 16 h. $Na_2SO_4$ (0.1 g) was added and stirred for 30 min, filtered over Celite® and concentrated. The crude was purified by column chromatography (0–5% MeOH in $CH_2Cl_2$ with 1% of $NH_4OH$ (aq.)) to provide the title compound. MS m/z=455.5 $(M+H)^+$ Calc'd for $C_{27}H_{30}N_6O$: 454.58.

EXAMPLE 151

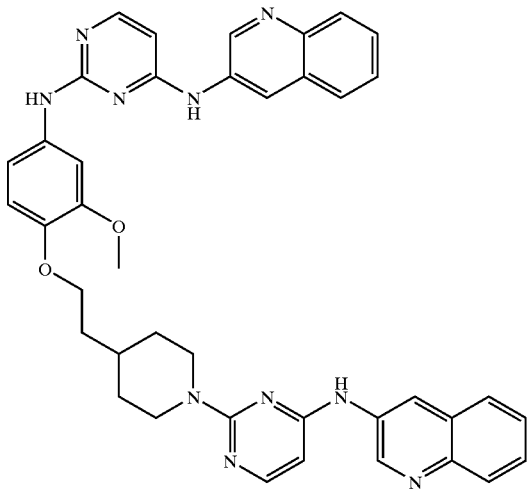

$N^2$-[3-Methoxy-4-(2-{1-[4-(quinolin-3-ylamino)-pyrimidin-2-yl]-piperidin-4-yl}-ethoxy)-phenyl]-$N^4$-quinolin-3-yl-pyrimidine-2,4-diamine

Step A

NaH (7.08 g, 177 mmol) (60% in oil) was washed with hexanes (3× under $N_2$), suspended in 250 mL of THF and cooled to 0° C. To this mixture was added 20.1 g (115 mmol) of trimethylphosphonoacetate in 20 mL of THF and the resulting mixture was stirred at 20° C. for 30 min. 1-Methylpiperid-4-one (10 g, 88.5 mmol) in 25 mL of THF was added and stirring was continued for 4 h. Water (5 mL) was carefully added and the mixture was poured into brine, extracted with 800 mL EtOAc. Drying and evaporation gave crude (1-methyl-piperidin-4-ylidene)-acetic acid methyl ester as a 1:1 mixture of isomers.

Step B (1-Methyl-piperidin-4-ylidene)-acetic acid methyl ester (Step A) was stirred under $H_2$ overnight (1.1 g of 10% Pd/C and 200 mL EtOH), filtered and evaporated to give (1-methyl-piperidin-4-yl)-acetic acid methyl ester as a yellow oil/white solid.

Step C

LAH (2.25 g, 59.3 mmol) was slowly added to 150 mL of THF. (1-Methyl-piperidin-4-yl)-acetic acid methyl ester (Step B) in 30 mL of THF was added dropwise to the LAH in THF and the resulting mixture was stirred for 4 h. Water (2.26 mL), 2.26 mL of 15% NaOH and 6.78 mL of water were carefully added and stirring was continued for 30 min. The mixture was filtered through Celite®, the solids were washed with EtOAc and the filtrate was evaporated, giving 2-(1-methyl-piperidin-4-yl)-ethanol as a yellow oil.

Step D

To a mixture of 3.0 g (17.7 mmol) of 4-nitroguiacol, 1.69 g (11.8 mmol) of N-methyl 4-piperidine-ethanol (Step C) and 4.64 g (17.7 mmol) of $Ph_3P$ in 60 mL of THF at 0° C. was added 3.49 mL (17.7 mmol) of DIAD. The resulting mixture was stirred at 0° C. for 30 min then at RT overnight, at which time a yellow precipitate had formed. The mixture was evaporated, taken up in EtOAc and extracted into 2M HCl. Basification of the aqueous extract with 5 M NaOH and extraction into EtOAc, followed by drying and evaporation to give crude compound, which was purified by chromatography (elution with 9:1 $CH_2Cl_2$-MeOH then 9:1 $CH_2Cl_2$-MeOH with 1% $Et_3N$) giving 3-methoxy-4-[2-(1-methyl-piperidin-4-yl)-ethoxy]-phenylamine as a yellow solid.

Step E

Standard catalytic hydrogenation of 3-methoxy-4-[2-(1-methyl-piperidin-4-yl)-ethoxy]-phenylamine (Step D) gave 3-methoxy-4-[2-(1-methyl-piperidin-4-yl)-ethoxy]-phenylamine as a red solid.

Step F

To a solution of (2-chloro-pyrimidin-4-yl)-quinolin-3-yl-amine (105 mg, 0.41 mmol, 1.0 eq.) and 3-methoxy-4-[2-(1-methyl-piperidin-4-yl)-ethoxy]-phenylamine (Step E, 119 mg, 0.45 mmol, 1.1 eq.) in 0.5 mL of DMSO was added a 1/1 (v/v) mixture of TFA/Et$_3$N (77 µl, 0.41 mmol, 1.0 eq.). The reaction mixture was heated to 100° C. and stirred for 16 h, cooled, concentrated and purified by column chromatography (0–5% MeOH in CH$_2$Cl$_2$ with 1% NH$_4$OH (aq.)). Trituration with CH$_2$Cl$_2$ provided the title compound. MS m/z=691.8 (M+H)$^+$ Calc'd for C$_{40}$H$_{38}$N$_{10}$O$_2$: 690.81.

EXAMPLE 152

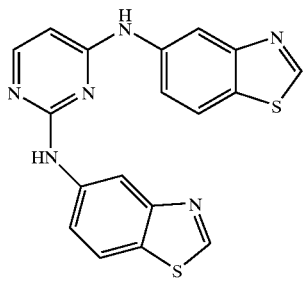

N$^2$-Benzo[b]benzothiazole-5-yl-N$^4$-benzothiazole-5-yl-pyrimidine-2,4-diamine To a round bottom flask, equipped with a magnetic stirrer was added 2,4-dichloropyrimidine (0.500 g, 0.0034 mole) and 10 mL of IPA. To the resulting mixture was added 5-aminobenzothiazole (0.654 g, 0.0044 mole), along with NaHCO$_3$ (0.857 g, 0.0102 mole). The mixture was heated to 80° C. for 8 h, cooled, and the solvent was removed in-vacuo. The mixture was diluted with EtOAc and H$_2$O, and transferred into a separatory funnel. The organics were collected, dried over Na$_2$SO$_4$, and concentrated in-vacuo. MeOH was added to the residue, and the precipitate was collected by filtration. After drying, the title compound was isolated as a yellow powder. MS: 377 (M+H); Calc'd for C$_{18}$H$_{12}$N$_6$S$_2$: 376.5.

EXAMPLE 153

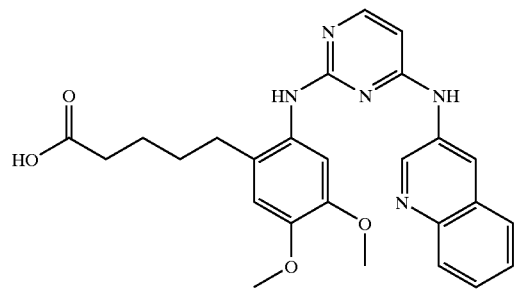

5-{4,5-Dimethoxy-2-[4-(quinolin-3-ylamino)-pyrimidin-2-ylamino]-phenyl}-pentanoic acid Step A: Preparation of 5-(2-Amino-4,5-Dimethoxy-phenyl)-pentanoic acid.

To a solution of 5-(2-amino-4,5-dimethoxy-phenyl)-pentanoic acid ethyl ester (Example 122, Step B) (0.1 g, 0.35 mmol) in THF (3 mL) was added NaOH (2 M, aqueous) (3 mL) and the mixture was stirred vigorously at RT for 12 h. The reaction was neutralized by the slow addition of HCl (2 N, aqueous) followed by removal of the THF under reduced pressure. The aqueous mixture was extracted with CH$_2$Cl$_2$ (3×10 mL) and the organic layers were combined, washed with brine, dried with MgSO$_4$, and filtered. Concentration under reduced pressure afforded the title compound as a brown solid that was carried on without purification.

Step B: Preparation of 5-{4,5-Dimethoxy-2-[4-(quinolin-3-ylamino)-pyrimidin-2-ylamino]-phenyl}-pentanoic acid.

The title compound was prepared by the method described in Example 87 using 5-(2-amino-4,5-dimethoxy-phenyl)-pentanoic acid from Step A above. MS m/z=474.2. Calc'd for C$_{26}$H$_{27}$N$_5$O$_4$: 473.54.

EXAMPLE 154

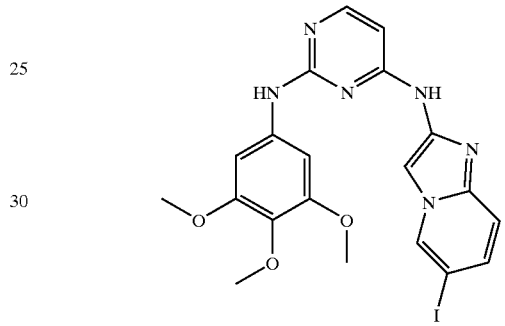

N$^4$-(6-Iodoimidazo[1,2-a]pyridin-2-yl)-N$^2$-(3,4,5-tris(methoxy)phenyl)-2,4-pyrimidinediamine Step A.

To a stirred suspension of 6-iodo-2-hydroxycarbonyl-imidazo[1,2-a]pyridine (0.5 g, 1.7 mmol) in CH$_2$Cl$_2$ (5 mL) was added, at RT, DPPA (0.56 mL, 2.6 mmol), and Et$_3$N (0.36 mL, 2.6 mmol). The reaction mixture was stirred at RT for 18 h. The reaction was stopped by addition of a saturated solution of NH$_4$Cl. The reaction mixture was diluted with CH$_2$Cl$_2$ and the layers separated. The aqueous layer was extracted twice with CH$_2$Cl$_2$. The combined organic layers were washed twice with H$_2$O and concentrated under vacuum. The crude acyl azide was directly used in the next step without further purification.

Step B:

A solution of the crude acyl azide (Step A) was heated at reflux for 4 h in t-BuOH (5 mL). The t-BuOH was removed under vacuum and the residue was purified by flash chromatography in 40% EtOAc/Hexane to give 6-iodo-2-[(tert-butoxycarbonyl)amino]-imidazo[1,2-a]pyridine.

Step C:

To a stirred solution of 6-iodo-2-[(tert-butoxycarbonyl)amino]-imidazo[1,2-a]pyridine (Step B, 0.32 g, 0.89 mmol) in CH$_2$Cl$_2$ (5 mL) cooled to 0° C. was added TFA (0.7 mL, 8.9 mmol). The reaction was stirred 18 h at RT. The solvents were removed under vacuum. The residue was dissolved in 2N NaOH and the solution stirred 2 h at RT. The mixture was extracted several times with CH$_2$Cl$_2$. The crude 6-iodo-2-aminoimidazo[1,2-a]pyridine was used in the next step without further purification.

Step D.

The 6-iodo-2-aminoimidazo[1,2-a]pyridine (Step C) was coupled to the 2,4-dichloropyridine using the general procedure described in Preparation A to afford 2-chloro-4-(6-iodo-2-aminoimidazo[1,2-a]pyridinyl)-1,3-pyrimidine as a brown solid.

Step E:

The title compound was prepared by the method described in Example 65 using 2-chloro-4-(6-iodo-2-aminoimidazo[1,2-a]pyridinyl)-1,3-pyrimidine (Step D) and 3,4,5-trimethoxyaniline. MS (MH$^+$)=519.0, MW: 520.33 Calc'd for $C_{20}H_{21}N_6O_3$.

Example 155

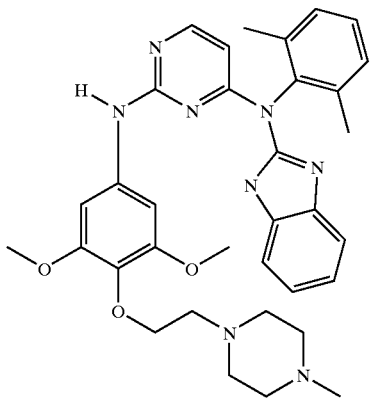

N$^4$-(1H-Benzimidazol-2-yl)-N$^2$-{3,5-dimethoxy-4-[2-(4-methyl-piperazin-1-yl)-ethoxy]-phenyl}-N$^4$-(2,6-dimethyl-phenyl)-pyrimidine-2,4-diamine Step A Trimethoxybenzene (100 g, 0.594 mol) was dissolved in AcOH (220 mL) and stirred while adding 70% HNO$_3$ (69 mL, 1.088 mol) over 20 min. The temperature was kept at 70° C. by cooling as necessary in a water bath. The cooling bath was removed after addition and the mixture remained at 65° C. for several min before cooling. Ice/water was added to precipitate a solid product which was washed well with water. 1M NaOH (500 mL) was added and stirred with the solid for 5 min. The solid was collected, washed with water until the washings were colorless and dried in air, giving 3,4,5-trimethoxynitrobenzene as pale yellow needles.

Step B

A mixture of 3,4,5-trimethoxynitrobenzene (Step A, 10.35 g, 48.5 mmol) and KOH (12.6 g, 194 mmol) was stirred and heated under reflux under N$_2$ for 48 h. The cooled mixture was filtered and the solid was washed with CH$_2$Cl$_2$ (3×) then EtOH (3×). The potassium 2,6-dimethoxy-4-nitrophenoxide as purple-pink leaflets was air dried.

Step C

A mixture of potassium 2,6-dimethoxy-4-nitrophenoxide (Step B, 3.3 g, 13.9 mmol), K$_2$CO$_3$ (5.8 g, 41.8 mmol), NaI (0.21 g, 1.39 mmol), and 1-bromo-2-chloroethane (11.6 mL, 139 mmol) in CH$_3$CN (50 mL) was stirred and heated under reflux under N$_2$ for 40 h when the color had turned pale brown. Filtration, washing the solids well with CH$_3$CN and evaporating the filtrate gave 3,5-dimethoxy-4-(2-chloroethoxy)nitrobenzene as a pale brown solid.

Step D

A mixture of 3,5-dimethoxy-4-(2-chloroethoxy)-nitrobenzene (Step C, 3.25 g, 12.5 mmol), N-methylpiperazine (4.14 mL, 37.4 mmol) and K$_2$CO$_3$ (4.30 g, 31.2 mmol) in CH$_3$CN (50 mL) was stirred and heated under reflux under N$_2$ for 18 h. The mixture was filtered and solids were washed well with CH$_2$Cl$_2$. The filtrate was evaporated giving a brown oil which was purified by silica gel chromatography (9:1 CH$_2$Cl$_2$:MeOH) giving an orange-brown gum which solidified slowly.

Step E 3,5-Dimethoxy-4-(2-(4-methylpiperazin-1-yl)ethoxy)-aniline was obtained by hydrogenation of the product of Step D over Pd/C (5%) in EtOH.

Step F

A 3-neck round bottom flask was charged with NaH (60% dispersion in mineral oil, 0.41 g, 10.1 mmol, 1.2 eq.) under N$_2$. The mineral oil was removed by stirring in n-heptane (3×10 mL) and decanting the supernatant liquid. The NaH was suspended in anhydrous THF (20 mL) and cooled to 0° C. A solution of 2-(2,6-dimethylphenylamino)-1H-benzimidazole (2.0 g, 8.4 mmol) in anhydrous THF (15 mL) was added slowly and the reaction was stirred at 0° C. for 0.5 h. A solution of 2,4-dichloropyrimidine (1.89 g, 12.7 mmol, 1.5 eq.) in anhydrous THF (15 mL) was added and the reaction was stirred at 0° C. for 0.5 h under N$_2$, then warmed to RT and stirred for 18 h. The reaction was diluted with CH$_2$Cl$_2$ and sat. aq. NaHCO$_3$. The organic layer was separated, dried (Na$_2$SO$_4$) and concentrated in vacuo. The residue was taken up into IPA and triturated with 1M HCl in Et$_2$O (16 mmol). The resulting precipitate was separated by filtration and rinsed with n-heptane and n-heptane/EtOAc (1:1) to yield off-white crystals of a mixture of regioisomers as the HCl salts. The salts were suspended in hot CH$_3$CN and filtered. The solids, a mixture of regioisomers, was taken up into CH$_2$Cl$_2$ and free-based with sat. aq. NaHCO$_3$. The organic layer was dried (Na$_2$SO$_4$) and concentrated in vacuo to afford a fluffy white solid. The solids were dissolved in CH$_2$Cl$_2$, adsorbed onto silica and purified by column chromatography (silica; n-heptane:EtOAc; 4:1). The product fractions were combined and the solvent removed in vacuo to afford 2-(N-(2-chloropyrimid-4-yl)-2,6-dimethylphenylamino)-1H-benzimidazole as a white solid. MS m/z=350 (M+H). Calc'd for $C_{19}H_{40}N_8O_3$=349.

Step G

A pressure tube was charged with a solution of 2-(N-(2-chloropyrimid-4-yl)-2,6-dimethylphenylamino)-1H-benzimidazole (50 mg, 0.14 mmol), 3,5-dimethoxy-4-[2-(4-methylpiperazin-1-yl)-ethoxy]phenylamine (42 mg, 0.14 mmol) in glacial AcOH (2 mL). The reaction, a dark brown solution, was heated to 100° C. for 18 h. The reaction was cooled to RT and then basified by careful addition of 5M NaOH (15 mL). The aqueous solution was extracted with CH$_2$Cl$_2$. The combined organic extracts were dried (Na$_2$SO$_4$) and the solvent was removed in vacuo. The residue was purified by column chromatography (silica; CH$_2$Cl$_2$:MeOH; 8:2) to afford the title compound as a light purple solid. MS m/z=609 (M+H). Calc'd for $C_{34}H_{40}N_8O_3$=608.

EXAMPLE 156

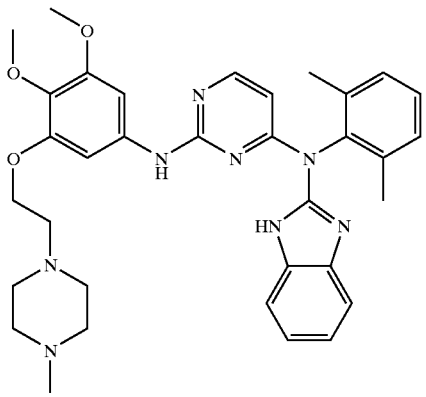

N⁴-(1H-Benzimidazo-2-yl)-N²-{3,4-dimethoxy-5-[2-(4-methylpiperazin-1-yl)-ethoxy]-phenyl}-N⁴-(2,6-dimethylphenyl)-pyrimidine-2,4-diamine Step A 2,3-Dimethoxyphenol (25.0 g, 0.162 mol) was dissolved in 1 L of acetone and $K_2CO_3$ (16.4 g, 0.119 mol) was added under $N_2$. Benzyl bromide (31.0 mL, 0.261 mol) was added followed by more (200 mL) acetone. The mixture was heated and stirred under reflux for 48 h. Filtration and evaporation gave a red oil. Purification by flash chromatography, eluting first with 80:20 then 50:50 hexane:EtOAc gave pure yellow material.

Step B

1-Benzyloxy-2,3-dimethoxybenzene (10 g, 40.9 mmol) and AcOH (20 mL) were stirred under $N_2$ and cooled to 5° C. while adding fuming $HNO_3$ (3 mL, 72.4 mmol) dropwise over 10 min. The temperature rose to 60° C. Stirring was continued at 5° C. for 1 h. The mixture was poured into ice/water and the oil was extracted into EtOAc (4×150 mL). The extracts were washed with 2M NaOH (100 mL) then brine and dried. Evaporation gave a dark red oil. Treatment with EtOAc and hexane followed by flash chromatography, eluting with 50:50 hexane:EtOAc containing 0.1% TEA gave a yellow oil which on further treatment with EtOAc/hexane gave a fluffy yellow solid.

Step C

A mixture of 1-benzyloxy-2,3-dimethoxy-5-nitrobenzene (4.96 g, 17.1 mmol) was stirred in TFA (13.5 mL) at 20° C. overnight. Evaporation of the solvent gave a dark solid, which was triturated with toluene to give a yellow-green solid. Evaporation of the filtrate and trituration with toluene/hexane afforded additional material.

Step D

A mixture of 2,3-dimethoxy-5-nitrophenol (1.069 g, 5.37 mmol), 1-bromo-2-chloroethane (4.44 mL, 53.3 mmol) and $K_2CO_3$ (1.84 g, 13.3 mmol) in $CH_3CN$ (15 mL) was stirred and heated under reflux under $N_2$ for 41 h when the suspension was nearly colorless. Filtration, washing the solids with $CH_3CN$, evaporating the filtrate and dissolving the yellow solid in $CH_2Cl_2$ (3×30 mL) gave an extract which was washed with brine, dried and evaporated giving a yellow solid.

Step E

A mixture of 1-(2-chloroethoxy)-2,3-dimethoxy-5-nitrobenzene (1.382 g, 5.28 mmol), $K_2CO_3$ (1.83 g, 13.2 mmol), and N-methylpiperazine (1.76 mL, 15.85 mmol) was stirred and heated under $N_2$ in $CH_3CN$ (20 mL) under reflux overnight. The next day 0.80 g $K_2CO_3$ and 0.66 mL piperazine were added (1.1 eq.) and heated for 3 h more when HPLC showed that the reaction was complete. The solids were filtered and washed well with $CH_3CN$ and the filtrate was evaporated at 80° C. to remove excess amine. The resulting red oil was dissolved in $CH_2Cl_2$ and washed with water. The aqueous layer was washed with $CH_2Cl_2$. The combined organic layers were dried and evaporated giving 2,3-dimethoxy-1-(2-(4-methylpiperazin-1-yl)ethoxy)-5-nitrobenzene.

Step F 3,4-Dimethoxy-5-[2-(4-methylpiperazin-1-yl)-ethoxy]-phenylamine was obtained by hydrogenation of the product of Step E over Pd/C (5%) in EtOH.

Step G

A pressure tube was charged with a solution of 2-(N-(2-chloropyrimid-4-yl)-2,6-dimethylphenylamino)-1H-benzimidazole (50 mg, 0.14 mmol), from Example 155 Step F, 3,4-dimethoxy-5-[2-(4-methylpiperazin-1-yl)-ethoxy]-phenylamine (42 mg, 0.14 mmol) in glacial AcOH (2 mL). The reaction, a dark brown solution, was heated to 95° C. for 60 h. The reaction was cooled to RT then basified by careful addition of 5M NaOH (15 mL). The aqueous solution was extracted with $CH_2Cl_2$. The combined organic extracts were dried ($Na_2SO_4$) and the solvent removed in vacuo. The residue was purified by column chromatography (silica; $CH_2Cl_2$:MeOH; 9:1) to afford a light brown solid. MS m/z=609 (M+H). Calc'd for $C_{34}H_{40}N_8O_3$=608.

EXAMPLE 157

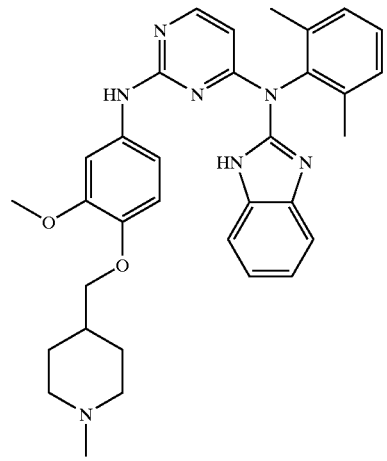

N⁴-(1H-Benzimidazol-2-yl)-N²-{3-methoxy-4-[1-methylpiperidin-4-yl-methoxy]-phenyl}-N⁴-(2,6-dimethylphenyl)-pyrimidine-2,4-diamine Step A 4-Piperidine-methanol was dissolved in methylformate at 0° C. The mixture was stirred at 0° C. for 30 min then warmed to 20° C. and stirred 90 min. Solid NaOH was added (0.87 g, pellets) and the mixture was stirred for 16 h. $CH_2Cl_2$ was added, the NaOH removed, and the solution was treated with 1M HCl in $Et_2O$ (10 mL). Filtration of the mixture over Celite yielded a yellow-orange oil.

Step B

A mixture of (1-formylpiperidin-4-yl)methanol (1.13 g, 7.89 mmol), 4-nitroguaiacol (2.0 g, 11.8 mmol) and polymer-supported $Ph_3P$ (ca. 3 mmol/g, 3.94 g, 11.8 mmol) in anhydrous THF (30 mL) was cooled to 0° C. and treated with DIAD (2.33 mL, 11.8 mmol) dropwise. The mixture was stirred at 0° C. for 30 min then at 20° C. overnight. The resin was filtered, and washed with CH$_2$Cl$_2$ then MeOH and the filtrate was evaporated giving deep orange oil. This was taken up in CH$_2$Cl$_2$, washed with 2M NaOH, 2M HCl then brine, dried and evaporated giving a pale brown oil. This was taken up in 50:50 EtOAc:Hexane, and filtered through Celite. The filtrate was evaporated, taken up in EtOAc and washed with 1M NaOH. The solution was dried, evaporated and the residue was purified by column chromatography (50:50 EtOAc:Hexane to remove impurities. Product was eluted with 9:1 CH$_2$Cl$_2$:MeOH to give a yellow oil which crystallized on standing.

Step C

A suspension of the 4-(1-formylpiperidin-4-yl)methoxy-3-methoxynitrobenzene (1.24 g, 4.2 mmol) in THF (5 mL) under N$_2$ was stirred while adding BH$_3$.THF (1M solution in THF, 8.4 mL, 8.4 mmol) then heated to 60° C. for 2 h. Further BH$_3$ solution was added (to a total of 5 eq.) together with 20 mL THF. The mixture was heated at reflux until disappearance of starting material. The reaction was cooled and MeOH (25 mL) was added carefully followed by CH$_2$Cl$_2$. The crude reaction mixture was washed with brine, 2M NaOH (4×) dried and evaporated. The residue was dissolved in MeOH, a few drops of AcOH added and heated under reflux for 3 days. Evaporation and chromatography in 9:1 CH$_2$Cl$_2$:MeOH containing 1% TEA afforded a brown solid.

Step D 4-(1-Methylpiperidin-4-yl)methoxy-3-methoxyaniline was obtained by hydrogenation of the product of Step C over Pd/C (5%) in EtOH.

Step E

A pressure tube was charged with a solution of 2-(N-(2-chloropyrimid-4-yl)-2,6-dimethylphenylamino)-1H-benzimidazole (50 mg, 0.14 mmol), from Example 155 Step F, 3-methoxy-4-(1-methylpiperidin-4-ylmethoxy)-phenylamine (36 mg, 0.14 mmol) in glacial AcOH (2 mL). The reaction, a dark brown solution, was heated to 80° C. for 18 h. The reaction was cooled to RT then basified by careful addition of 5M NaOH (15 mL). The aqueous solution was extracted with CH$_2$Cl$_2$. The combined organic extracts were dried (Na$_2$SO$_4$) and the solvent removed in vacuo. The residue was purified by column chromatography (silica; CH$_2$Cl$_2$:MeOH; 9:1, containing TEA [1%]) to afford a brown solid, which was further purified by column chromatography (silica; CH$_2$Cl$_2$:MeOH; 9:1; containing TEA [0.5%]) to afford a light brown solid. MS m/z=564 (M+H). Calc'd for C$_{33}$H$_{37}$N$_7$O$_2$=563.

EXAMPLE 158

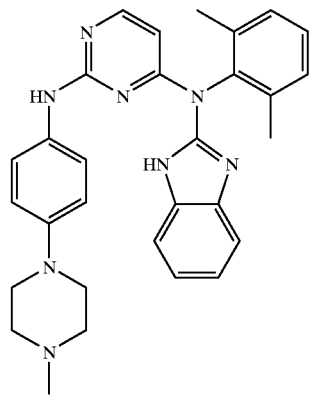

N$^4$-(1H-Benzimidazol-2-yl)-N$^2$-[4-(4-methylpiperazin-1-yl)-phenyl]-N$^4$-(2,6-dimethyl-phenyl)-pyrimidine-2,4-diamine A pressure tube was charged with a solution of 2-(N-(2-chloropyrimid-4-yl)-2,6-dimethylphenylamino)-1H-benzimidazole (50 mg, 0.14 mmol), from Example 155 Step F, 4-(4-methylpiperazin-1-yl)-phenylamine (27 mg, 0.14 mmol) in glacial AcOH (2 mL). The reaction, a dark brown solution, was heated to 100° C. for 18 h. The reaction was cooled to RT then basified by careful addition of 5M NaOH (15 mL). The aqueous solution was extracted with CH$_2$Cl$_2$. The combined organic extracts were dried (Na$_2$SO$_4$) and the solvent was removed in vacuo. The residue was purified by column chromatography (silica; CH$_2$Cl$_2$:MeOH; 9:1; containing TEA (0.2%)) to afford a light brown solid. MS m/z=505 (M+H). Calc'd for C$_{30}$H$_{32}$N$_8$=504.

Examples 159–197 were prepared from the corresponding amines in a manner similar to that described above for Example 1:

| Ex. | Structure | formula | mol wt | EM | Found |
|---|---|---|---|---|---|
| 159 | N$^2$-(4-Fluoro-3-methoxy-phenyl)-N$^4$-quinolin-3-yl-pyrimidine-2,4-diamine | C$_{20}$H$_{16}$FN$_5$O | 361.3818 | 361 | 362.1 |
| 160 | N,N-Dimethyl-4-[4-(quinolin-3-ylamino)-pyrimidin-2-ylamino]- | C$_{22}$H$_{20}$N$_6$O | 384.4443 | 384 | 385.1 |

-continued

| Ex. | Structure | formula | mol wt | EM | Found |
|---|---|---|---|---|---|
| | benzamide | | | | |
| 161 | 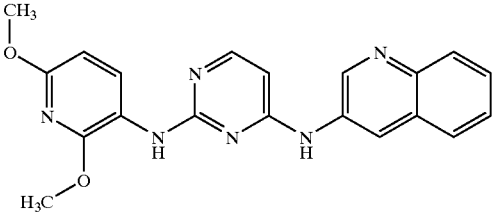 N²-(2,6-Dimethoxy-pyridin-3-yl)-N⁴-quinolin-3-yl-pyrimidine-2,4-diamine | $C_{20}H_{18}N_6O_2$ | 374.4055 | 374 | 375.1 |
| 162 | 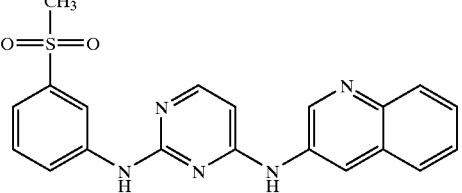 N²-(3-Methanesulfonylphenyl)-N⁴-quinolin-3-yl-pyrimidine-2,4-diamine | $C_{20}H_{17}N_5O_2S$ | 391.4548 | 391 | 392 |
| 163 | 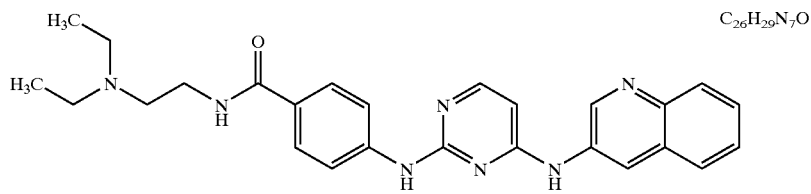 N-(2-Diethylaminoethyl)-4-[4-(quinolin-3-ylamino)-pyrimidin-2-ylamino]-benzamide | $C_{26}H_{29}N_7O$ | 455.5673 | 455 | 456.2 |
| 164 | 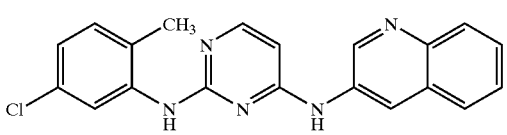 N²-(5-Chloro-2-methyl-phenyl)-N⁴-quinolin-3-yl-pyrimidine-2,4-diamine | $C_{20}H_{16}ClN_5$ | 361.837 | 361 | 362.2 |
| 165 | 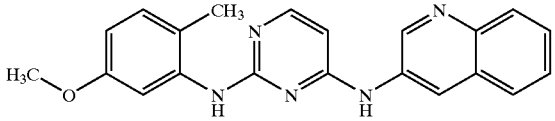 N²-(5-Methoxy-2-methyl-phenyl)-N⁴-quinolin-3-yl-pyrimidine-2,4-diamine | $C_{21}H_{19}N_5O$ | 357.4185 | 357 | 358.3 |

-continued

| Ex. | Structure | formula | mol wt | EM | Found |
|---|---|---|---|---|---|
| 166 | N⁴-Quinolin-3-yl -N²-(4-trifluoromethyl-phenyl)-pyrimidine-2,4-diamine | C₂₀H₁₄F₃N₅ | 381.3633 | 381 | 382.1 |
| 167 | N⁴-Quinolin-3-yl-N²-(2,2,3,3-tetrafluoro-2,3-dihydro-benzo [1,4] dioxin-6-yl)-pyriinidine-2,4-diamine | C₂₁H₁₃F₄N₅O₂ | 443.3637 | 443 | 444 |
| 168 | N²-(2-Chloro-5-methoxy-phenyl)-N⁴-quinolin-3-yl-pyrimidine-2,4-diamine | C₂₀H₁₆ClN₅O | 377.8364 | 377 | 378 |
| 169 | 1-{6-[4-(Quinolin-3-ylamino)-pyrimidin-2-ylamino]-2,3-dihydro-indol-1-yl)-ethanone | C₂₃H₂₀N₆O | 396.4555 | 396 | 397.1 |
| 170 | N-Methyl-3-[4-(quinolin-3-ylamino)-pyrimidin-2-ylamino]-benzamide | C₂₁H₁₈N₆O | 370.4172 | 370 | 371.2 |
| 171 | N⁴-Quinolin-3-yl-N²-quinolin-5-yl-pyrimidine-2,4-diamine | C₂₂H₁₆N₆ | 364.413 | 364 | 365.1 |

-continued

| Ex. | Structure | formula | mol wt | EM | Found |
|---|---|---|---|---|---|
| 172 | N⁴-Quinolin-3-yl-N²-quinolin-8-yl-pyrimidine-2,4-diamine | $C_{22}H_{16}N_6$ | 364.413 | 364 | 365.1 |
| 173 | N²-(4-Methoxynaphthalen-2-yl)-N⁴-quinolin-3-yl-pyrimidine-2,4-diamine | $C_{24}H_{19}N_5O$ | 393.4519 | 393 | 394.1 |
| 174 | Morpholin-4-yl-{4-[4-(quinolin-3-ylamino)-pyrimidin-2-ylamino]-phenyl}-methanone | $C_{24}H_{22}N_6O_2$ | 426.4819 | 426 | 427.1 |
| 175 | {3-[4-(Quinolin-3-ylamino)-pyrimidin-2-ylamino]-phenyl}-methanol | $C_{20}H_{17}N_5O$ | 343.3914 | 343 | 344.1 |
| 176 | 1-{3-[4-(Quinolin-3-ylamino)-pyrimidin-2-ylamino]-phenyl}-ethanone | $C_{21}H_{17}N_5O$ | 355.4025 | 355 | 356.1 |

-continued

| Ex. | Structure | formula | mol wt | EM | Found |
|---|---|---|---|---|---|
| 177 | 3-Methyl-4-[4-(quinolin-3-ylamino)-pyrimidin-2-ylamino]-benzoic acid methyl ester | $C_{22}H_{19}N_5O_2$ | 385.429 | 385 | 386 |
| 178 | 4-Methoxy-3-[4-(quinolin-3-ylamino)-pyrimidin-2-ylamino]-benzamide | $C_{21}H_{18}N_6O_2$ | 386.4166 | 386 | 387.1 |
| 179 | N-{4-Methoxy-3-[4-(quinolin-3-ylamino)-pyrimidin-2-ylamino]-phenyl}-acetamide | $C_{22}H_{20}N_6O_2$ | 400.4437 | 400 | 401.2 |
| 180 | $N^2$-(5-Methoxy-2-methyl-4-nitrophenyl)-$N^4$-quinolin-3-yl-pyrimidine-2,4-diamine | $C_{21}H_{18}N_6O_3$ | 402.416 | 402 | 403 |
| 181 | $N^2$-(2-Fluoro-5-methanesulfonyl-phenyl)-$N^4$-quinolin-3-yl-pyrimidine-2,4-diamine | $C_{20}H_{16}FN_5O_2S$ | 409.4452 | 409 | 410 |

-continued

| Ex. | Structure | formula | mol wt | EM | Found |
|---|---|---|---|---|---|
| 182 | N²-(2-Methyl-benzothiazol-5-yl)-N⁴-quinolin-3-yl-pyrimidine 2,4-diamine | $C_{21}H_{16}N_6S$ | 384.4659 | 384 | 385.3 |
| 183 | N²-(4-Bromo-2-trifluoromethoxyphenyl)-N⁴-quinolin-3-yl-pyrimidine-2,4-diamine | $C_{20}H_{13}BrF_3N_5O$ | 476.2587 | 476 | 476 |
| 184 | N²-(2-Bromo-4-trifluoromethoxyphenyl)-N⁴-quinolin-3-yl-pyrimidine-2,4-diamine | $C_{20}H_{13}BrF_3N_5O$ | 476.2587 | 476 | 476 |
| 185 | N²-Indan-5-yl-N⁴-quinolin-3-yl-pyrimdine-2,4-diamine | $C_{22}H_{19}N_5$ | 353.4302 | 353 | 354.1 |
| 186 | N²-Pyridin-4-yl-N⁴-quinolin-3-yl-pyrimidine-2,4-diamine | $C_{18}H_{14}N_6$ | 314.3525 | 314 | 315 |
| 187 | N²-(3-Nitrophenyl)-N⁴-quinolin-3-yl-pyrimidine-2,4-diamine | $C_{19}H_{14}N_6O_2$ | 358.3624 | 358 | 359.1 |

-continued

| Ex. | Structure | formula | mol wt | EM | Found |
|---|---|---|---|---|---|
| 188 | 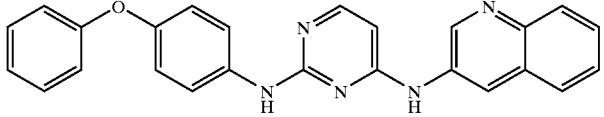<br>N²-(4-Phenoxyphenyl)-N⁴-quinolin-3-yl-pyrimidine-2,4-diamine | $C_{25}H_{19}N_5O$ | 405.4631 | 405 | 406.1 |
| 189 | 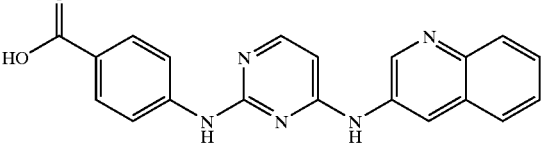<br>4-[4-(Quinolin-3-ylamino)-pyrimidin-2-ylamino]-benzoic acid | $C_{20}H_{15}N_5O_2$ | 357.3749 | 357 | 358.1 |
| 190 | 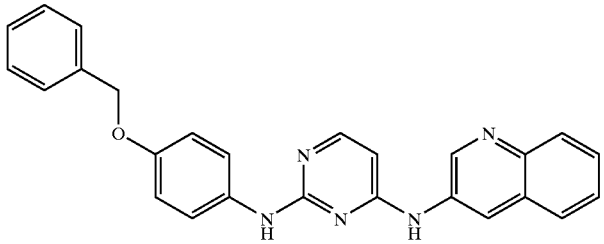<br>N²-(4-Benzyloxyphenyl)-N⁴-quinolin-3-yl-pyrimidine-2,4-diamine | $C_{26}H_{21}N_5O$ | 419.4902 | 419 | 420.1 |
| 191 | 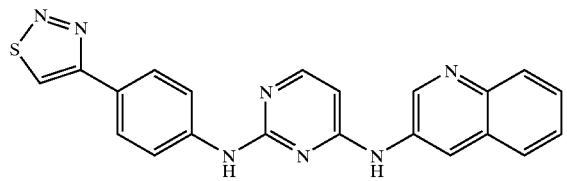<br>N⁴-Quinolin-3-yl-N²-(4-[1,2,3]thiadiazol-4-yl-phenyl)-pyrimidine-2,4-diamine | $C_{21}H_{15}N_7S$ | 397.4646 | 397 | 398 |
| 192 | 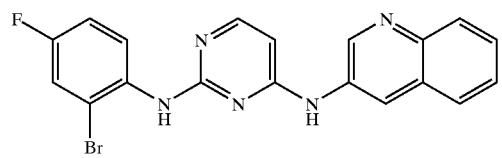<br>N²-(2-Bromo-4-fluoro-phenyl)-N⁴-quinolin-3-yl-pyrimidine-2,4-diamine | $C_{19}H_{13}BrFN_5$ | 410.2514 | 410 | 409.9 |

| Ex. | Structure | formula | mol wt | EM | Found |
|---|---|---|---|---|---|
| 193 | N²-(2,5-Dimethoxy-4-nitrophenyl)-N⁴-quinolin-3-yl-pyrimidine-2,4-diamine | $C_{21}H_{18}N_6O_4$ | 418.4154 | 418 | 419.1 |
| 194 | N²-(3-trifluoromethyl-sulfonylphenyl)-N⁴-quinolin-3-yl-pyrimidine-2,4-diamine | $C_{20}H_{14}F_3N_5O_2S$ | 445.4261 | 445 | 446 |
| 195 | N²-(3-Bromo-4-trifluoromethoxyphenyl)-N⁴-quinolin-3-yl-pyrimidine-2,4-diamine | $C_{20}H_{13}BrF_3N_5O$ | 476.2587 | 476 | 476 |
| 196 | 5-[4-(Quinolin-3-ylamino)-pyrimidin-2-ylamino]-1,3-dihydro-indol-2-one | $C_{21}H_{16}N_6O$ | 368.4013 | 368 | 369.1 |
| 197 | (4-Methyl-piperazin-1-yl)-{4-[4-(quinolin-3-ylamino)-pyrimidin-2-ylamino]-phenyl}-methanone | $C_{25}H_{25}N_7O$ | 439.5243 | 439 | 440.1 |

Other compounds included in this invention, set forth in Tables 1–4 below, can be prepared by the above methods.

TABLE 1

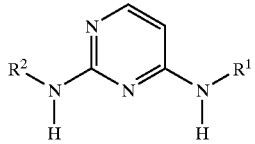

| # | R² | R¹ |
|---|---|---|
| 198. | 1-benzylindazol-5-yl | 3-quinolyl |
| 199. | 1-benzylindazol-5-yl | 3-isoquinolyl |
| 200. | naphth-1-yl | 2-pyridyl |
| 201. | 4-benzyloxy-phenyl | 3-pyridyl |
| 202. | 4-benzyloxy-3-chlorophenyl | 4-pyridyl |
| 203. | 3-chloro-4-fluorophenyl | 2-triazinyl |
| 204. | 3-chloronaphth-1-yl | 2-pyrazinyl |
| 205. | 4-methoxycarbonylphenyl | 2-pyrimidinyl |
| 206. | 3-(2-methoxyethoxy)-4-methoxyphenyl | 4-pyrimidinyl |
| 207. | 3,4-dimethoxyphenyl | 3-pyridyl |
| 208. | 1-benzylindazol-5-yl | 3-pyridazinyl |
| 209. | 1-benzylindazol-5-yl | 6-pyridazinyl |
| 210. | 3,4-diethoxyphenyl | 1-phthalzinyl |
| 211. | 3-bromophenyl | 2-naphthyridinyl |
| 212. | 3-methoxy-4-(2-methoxyethoxy)phenyl | 3-naphthyridinyl |
| 213. | 3-methylphenyl | 2-quinoxalinyl |
| 214. | 4,5-dimethoxy-3-(2-(morpholin-4-yl)ethoxy)phenyl | 6-quinazolinyl |
| 215. | 3-aminocarbonylphenyl | 6-cinnolinyl |
| 216. | 3-CH₃OCOCH₂-phenyl | 6-cinnolinyl |
| 217. | 3-(4-nitrophenylsulfonylamino)-phenyl | 2-pyridyl |
| 218. | 5-chloro-2-methyl-phenyl | 2-pyridyl |
| 219. | 4-[HO(CH₂)₂O]phenyl | 3-pyridyl |
| 220. | 6-indazolyl | 4-pyridyl |
| 221. | 5-benzimidazolyl | 4-pyridyl |
| 222. | 3,4-dimethoxy-6-methylphenyl | 3-pyridyl |
| 223. | 3,4,5-trimethoxyphenyl | 4-(4-NH₂SO₂-phenyl)-amino-2-pyrazinyl |
| 224. | 2-Phenylbenzoxazol-6-yl | 7-methoxy-3-quinolinyl |
| 225. | 2,3-bis(4-methoxyphenyl)quinoxalin-6-yl | 7-methoxy-3-quinolinyl |
| 226. | 2-dibenzofuryl | 7-trifluormethyl-3-quinolinyl |
| 227. | 1,1-dioxobenzo[b]thiophen-6-yl | 7-trifluormethoxy-3-quinolinyl |
| 228. | 1-(4-Methylpiperazino)isoquinolin-3-yl | 6-trifluormethoxy-3-quinolinyl |
| 229. | 2-Phenyl-6-quinoxalinyl | 6-methoxy-3-quinolinyl |
| 230. | 2-(4-Dimethylamino-phenyl)-benzoxazol-5-yl | 7-methoxy-3-quinolinyl |
| 231. | 2-Phenyl-3H-benzimidazol-5-yl | 6-methoxy-3-quinolinyl |
| 232. | 1-(2-Hydroxyethyl)-2-methyl-1H-benzimidazol-5-yl | 6-hydroxy-3-quinolinyl |
| 233. | [4,5-dihydro-4-carboxy-thiazol-2-yl]-benzthiazol-6-yl | 3-quinolinyl |
| 234. | 3-(Aminocarbonyl)-1H-indol-5-yl | 6-quinolinyl |
| 235. | 1-[(4-Methylphenyl)sulfonyl]-1H-indol-5-yl | 3-quinolinyl |

TABLE 2

| # | R¹⁰ |
|---|---|
| 236. | 2-chloro-5-methoxyphenyl |
| 237. | 4-methoxy-2-methylphenyl |
| 238. | 5-methoxy-2-methylphenyl |
| 239. | 3-trifluoromethoxyphenyl |
| 240. | 1,1,2,2-tetrafluoroethoxyphenyl |
| 241. | 4-trifluoromethoxyphenyl |
| 242. | 1-methyl-5-indazolyl |
| 243. | 2-methyl-2H-indazol-5-yl |
| 244. | 3-isopropylphenyl |
| 245. | 3,5-dimethoxyphenyl |
| 246. | 3,4-dimethoxyphenyl |
| 247. | 1,3-benzodioxol-5-yl |
| 248. | 1-methoxy-3-naphthyl |
| 249. | 6-methoxy-8-quinolyl |
| 250. | 3,5-bis(trifluoromethyl)phenyl |
| 251. | 2-cyano-4,5-dimethoxyphenyl |
| 252. | 4-cyanophenyl |
| 253. | 4-aminocarbonyl-3-methoxyphenyl |
| 254. | 4-(N-hydroxyethylamino)carbonyl-3-methoxyphenyl |
| 255. | 3-methoxy-4-pentafluoroethylphenyl |
| 256. | 2-ethoxycarbonyl-3,4,5-trimethoxyphenyl |
| 257. | 4-(3-Dimethylamino-propoxy)-phenyl; |
| 258. | 3,5-Dimethoxy-4-[2-(4-methyl-piperazin-1-yl)-ethoxy]-phenyl |
| 259. | 3,5-Dimethoxy-4-[3-(4-methyl-piperazin-1-yl)-propoxy]-phenyl |
| 260. | 3-Methoxy-4-[3-(4-methyl-piperazin-1-yl)-propoxy]-phenyl |
| 261. | 3-Methoxy-4-[2-(4-methyl-piperazin-1-yl)-ethoxy]-phenyl |
| 262. | 2-Methyl-4-(4-methyl-piperazin-1-yl)-phenyl |
| 263. | 4-(4-Isopropyl-piperazin-1-yl)-phenyl |
| 264. | 3-Fluoro-4-(4-methyl-piperazin-1-yl)-phenyl |
| 265. | 3-Fluoro-4-(3-piperidin-1-yl-propoxy)-phenyl |
| 266. | 3,4-Dimethoxy-5-[3-(4-methyl-piperazin-1-yl)-propoxy]-phenyl |
| 267. | 3-Methoxy-4-(1-methyl-piperidin-4-ylmethoxy)-phenyl |
| 268. | 3-Methoxy-4-[2-(1-methyl-piperidin-4-yl)-ethoxy]-phenyl |
| 269. | 4-(1-tert-butoxycarbonyl-piperazin-4-yl)phenyl |
| 270. | 4-(4-piperazinyl)phenyl |
| 271. | 4-(1-tert-butoxycarbonyl-piperazin-4-yl)-3-difluoromethoxy-phenyl |
| 272. | 3-Fluoro-4-(2-piperidin-1-yl-ethoxy)-phenyl |
| 273. | 3-Fluoro-4-[2-(4-methyl-piperazin-1-yl)-ethoxy]-phenyl |
| 274. | 3-Fluoro-4-[3-(4-methyl-piperazin-1-yl)-propoxy]-phenyl |
| 275. | 4-[2-(4-Methyl-piperazin-1-yl)-ethoxy]-phenyl |
| 276. | 3,5-Dimethoxy-4-(2-morpholin-4-yl-ethoxy)-phenyl |
| 277. | 3,5-Dimethoxy-4-(2-piperidin-1-yl-ethoxy)-phenyl |
| 278. | 2-Methyl-4-(3-piperidin-1-yl-propoxy)-phenyl |
| 279. | 2-Methyl-4-[3-(4-methyl-piperazin-1-yl)-propoxy]-phenyl |
| 280. | 2-Fluoro-4,5-dimethoxy-phenyl |
| 281. | 2-anthracenyl |
| 282. | 2-benzimidazolyl |
| 283. | Phenanthren-3-yl |
| 284. | 7-HOSO₂-naphth-2-yl |
| 285. | 3-carbazolyl |
| 286. | 2-phenanthrenyl |
| 287. | 5-HOSO₂-2-naphthyl |
| 288. | 8-HOSO₂-2-naphthyl |
| 289. | 2-HOSO₂-6-Naphthyl |
| 290. | 6-(4-Chlorophenoxy)Pyridin-3-yl |
| 291. | 6-(3-Pyridyloxy)Pyridin-3-yl |
| 292. | 6-(4-Chloro-2-Cyclohexylphenoxy)Pyridin-3-yl |
| 293. | 2-(2-Pyridyl)Benzimidazol-5-yl |
| 294. | 2-dibenzofuryl |
| 295. | 2-phenylbenzoxazol-6-yl |
| 296. | 2,3-bis(4-methoxyphenyl)quinoxalin-6-yl |
| 297. | 2-dibenzofuryl |
| 298. | 1,1-dioxobenzo[b]thiophen-6-yl |
| 299. | 1-(4-Methylpiperazino)isoquinolin-3-yl |
| 300. | 2-phenyl-6-quinoxalinyl |
| 301. | 2-(4-Dimethylaminophenyl)-benzoxazol-5-yl |

TABLE 2-continued

Structure: R¹⁰-NH-[pyrimidine-2,4-diyl]-NH-[quinolin-6-yl]

| # | R¹⁰ |
|---|---|
| 302. | 2-phenyl-3H-benzimidazol-5-yl |
| 303. | 1-(2-Hydroxyethyl)-2-methyl-1H-benzimidazol-5-yl |
| 304. | [4,5-dihydro-4-carboxy-thiazol-2-yl]-benzthiazol-6-yl |
| 305. | 3-(Aminocarbonyl)-1H-indol-5-yl |
| 306. | 1-[(4-Methylphenyl)sulfonyl]-1H-indol-5-yl |

TABLE 3

Structure: R¹⁰-NH-[pyrimidine-2,4-diyl]-NH-[quinolin-3-yl]

| # | R¹⁰ |
|---|---|
| 307. | 2-chloro-5-methoxyphenyl |
| 308. | 4-methoxy-2-methylphenyl |
| 309. | 5-methoxy-2-methylphenyl |
| 310. | 3-(1,1,2,2-tetrafluoroethoxy)phenyl |
| 311. | 3-(1,1,2,2-tetrafluoroethyl)phenyl |
| 312. | 2-methyl-2H-indazol-5-yl |
| 313. | 3-isopropyl |
| 314. | 4-cyanophenyl |
| 315. | 4-(N-hydroxyethylamino)carbonyl-3-methoxyphenyl |
| 316. | 1-methoxy-3-naphthyl |
| 317. | 6-methoxy-8-quinolyl |
| 318. | 4-(3-Dimethylamino-propoxy)-phenyl; |
| 319. | 3,5-Dimethoxy-4-[2-(4-methyl-piperazin-1-yl)-ethoxy]-phenyl |
| 320. | 3,5-Dimethoxy-4-[3-(4-methyl-piperazin-1-yl)-propoxy]-phenyl |
| 321. | 3-Methoxy-4-[3-(4-methyl-piperazin-1-yl)-propoxy]-phenyl |
| 322. | 3-Methoxy-4-[2-(4-methyl-piperazin-1-yl)-ethoxy]-phenyl |
| 323. | 2-Methyl-4-(4-methyl-piperazin-1-yl)-phenyl |
| 324. | 4-(Isopropyl-piperazin-1-yl)-phenyl |
| 325. | 3-Fluoro-4-(4-methyl-piperazin-1-yl)-phenyl |
| 326. | 3-Fluoro-4-(3-piperidin-1-yl-propoxy)-phenyl |
| 327. | 3,4-Dimethoxy-5-[3-(4methyl-piperazin-1-yl)-propoxy]-phenyl |
| 328. | 3-Methoxy-4-(1-methyl-piperidin-4-ylmethoxy)-phenyl |
| 329. | 3-Mehtoxy-4-[2-(1-methyl-piperidin-4-yl)-ethoxy]-phenyl |
| 330. | 4-(1-tert-butoxycarbonyl-piperazin-4-yl)phenyl |
| 331. | 4-(4-piperazinyl)phenyl |
| 332. | 4-(1-tert-butoxycarbonyl-piperazin-4-yl)-3-difluoromethoxy-phenyl |
| 333. | 3-Fluoro-4-(2-piperidin-1-yl-ethoxy)-phenyl |
| 334. | 3-Fluoro-4-[2-(4-methyl-piperazin-1-yl)-ethoxy]-phenyl |
| 335. | 3-Fluoro-4-[3-(4-methyl-piperazin-1-yl)-propoxy]-phenyl |
| 336. | 4-[2-(4-Methyl-piperazin-1-yl)-ethoxy]-phenyl |
| 337. | 3,5-Dimethoxy-4-(2-morpholin-4-yl-ethoxy)-phenyl |
| 338. | 3,5-Dimethoxy-4-(2-piperidin-1-yl-ethoxy)-phenyl |
| 339. | 2-Methyl-4-(3-piperidin-1-yl-propoxy)-phenyl |
| 340. | 2-Methyl-4-[3-(4-methyl-piperazin-1-yl)-propoxy]-phenyl |
| 341. | 2-Fluoro-4,5-dimethoxy-phenyl |
| 342. | 2-anthracenyl |
| 343. | 2-benzimidazolyl |
| 344. | Phenanthren-3-yl |
| 345. | 7-HOSO₂-naphth-2-yl |
| 346. | 3-carbazolyl |
| 347. | 2-phenanthrenyl |
| 348. | 5-HOSO₂-2-naphthyl |
| 349. | 8-HOSO₂-2-naphthyl |
| 350. | 2-HOSO₂-6-Naphthyl |
| 351. | 6-(4-Chlorophenoxy)Pyridin-3-yl |

TABLE 3-continued

Structure: R¹⁰-NH-[pyrimidine-2,4-diyl]-NH-[quinolin-3-yl]

| # | R¹⁰ |
|---|---|
| 352. | 6-(3-Pyridyloxy)Pyridin-3-yl |
| 353. | 6-(4-Chloro-2-Cyclohexylphenoxy)Pyridin-3-yl |
| 354. | 2-(2-Pyridyl)Benzimidazol-5-yl |
| 355. | 2-dibenzofuryl |
| 356. | 2-Phenylbenzoxazol-6-yl |
| 357. | 2,3-bis(4-methoxyphenyl)quinoxalin-6-yl |
| 358. | 2-dibenzofuryl |
| 359. | 1,1-dioxobenzo[b]thiophen-6-yl |
| 360. | 1-(4-Methylpiperazino)isoquinolin-3-yl |
| 361. | 2-Phenyl-6-quinoxalinyl |
| 362. | 2-(4-Dimethylamino-phenyl)-benzoxazol-5-yl |
| 363. | 2-Phenyl-3H-benzimidazol-5-yl |
| 364. | 1-(2-Hydroxyethyl)-2-methyl-1H-benzimidazol-5-yl |
| 365. | [4,5-dihydro-4-carboxy-thiazol-2-yl]-benzthiazol-6-yl |
| 366. | 3-(Aminocarbonyl)-1H-indol-5-yl |
| 367. | 1-[(4-Methylphenyl)sulfonyl]-1H-indol-5-yl |
| 368. | 2-amino-4,5-dimethoxyphenyl |
| 369. | 2-ethyl-4,5-dimethoxyphenyl |
| 370. | 2-HOCH₂-4,5-dimethoxyphenyl |
| 371. | 2-NH₂CH₂-4,5-dimethoxyphenyl |
| 372. | 2-NH₂(CH₂)₂-4,5-dimethoxyphenyl |
| 373. | 2-CH₃NH-4,5-dimethoxyphenyl |

TABLE 4

Structure: R¹⁰-NH-[pyrimidine-2,4-diyl]-NH-[isoquinolin-2-yl with R¹¹]

| # | R¹⁰ | R¹¹ |
|---|---|---|
| 374. | 2-chloro-5-methoxyphenyl | H |
| 375. | 4-methoxy-2-methylphenyl | H |
| 376. | 5-methoxy-2-methylphenyl | H |
| 377. | 3-(1,1,2,2-tetrafluoroethoxy)phenyl | H |
| 378. | 3-(1,1,2,2-tetrafluoroethyl)phenyl | H |
| 379. | 2-methyl-2H-indazol-5-yl | H |
| 380. | 3-isopropyl | H |
| 381. | 4-cyanophenyl | 1-OMe |
| 382. | 4-(N-hydroxyethylamino)carbonyl-3-methoxyphenyl | 1-OMe |
| 383. | 1-methoxy-3-naphthyl | 1-OMe |
| 384. | 6-methoxy-8-quinolyl | 1-OMe |
| 385. | 4-(3-Dimethylamino-propoxy)-phenyl | 1-OMe |
| 386. | 3,5-Dimethoxy-4-[2-(4-methylpiperazin-1-yl)-ethoxy]-phenyl | 1-OMe |
| 387. | 3,5-Dimethoxy-4-[3-(4-methylpiperazin-1-yl)-propoxy]-phenyl | 1-OMe |
| 388. | 3-Methoxy-4-[3-(4-methylpiperazin-1-yl)-propoxy]-phenyl | 1-OMe |
| 389. | 3-Methoxy-4-[2-(4-methylpiperazin-1-yl)-ethoxy]-phenyl | 1-OMe |
| 390. | 2-Methyl-4-(4-methylpiperazin-1-yl)-phenyl | H |
| 391. | 4-(4-Isopropylpiperazin-1-yl)-phenyl | H |
| 392. | 3-Fluoro-4-(4-methylpiperazin-1-yl)-phenyl | H |
| 393. | 3-Fluoro-4-(3-piperidin-1-yl-propoxy)-phenyl | 1-OMe |
| 394. | 3,4-Dimethoxy-5-[3-(4-methylpiperazin-1-yl) propoxy]-phenyl | 1-OMe |
| 395. | 3-Methoxy-4-(1-methylpiperidin-4-ylmethoxy)-phenyl | 1-OMe |
| 396. | 3-Methoxy-4-[2-(1-methylpiperidin-4-yl)-ethoxy]-phenyl | 1-OMe |

TABLE 4-continued

[Structure: pyrimidine with R10-NH at 2-position and NH-isoquinoline (with R11) at 4-position]

| # | R10 | R11 |
|---|-----|-----|
| 397. | 4-(1-tert-butoxycarbonylpiperazin-4-yl)phenyl | H |
| 398. | 4-(4-piperazinyl)phenyl | 1-OMe |
| 399. | 4-(1-tert-butoxycarbonylpiperazin-4-yl)-3-difluoromethoxy-phenyl | H |
| 400. | 3-Fluoro-4-(2-piperidin-1-yl-ethoxy)-phenyl | H |
| 401. | 3-Fluoro-4-[2-(4-methylpiperazin-1-yl)-ethoxy]-phenyl | H |
| 402. | 3-Fluoro-4-3-(4-methyl-piperazin-1-yl)-propoxy]-phenyl | 1-OMe |
| 403. | 4-[2-(4-Methyl-piperazin-1-yl)-ethoxy]-phenyl | 1-OMe |
| 404. | 3,5-Dimethoxy-4-(2-morpholin-4-yl-ethoxy)-phenyl | 1-OMe |
| 405. | 3,5-Dimethoxy-4-(2-piperidin-1-yl-ethoxy)-phenyl | 1-OMe |
| 406. | 2-Methyl-4-(3-piperidin-1-yl-propoxy)-phenyl | 1-OMe |
| 407. | 2-Methyl-4-[3-(4-methyl-piperazin-1-yl)-propoxy]-phenyl | H |
| 408. | 2-Fluoro-4,5-dimethoxy-phenyl | H |
| 409. | 2-anthracenyl | 1-OMe |
| 410. | 2-benzimidazolyl | 1-OMe |
| 411. | phenanthren-3-yl | 1-OMe |
| 412. | 7-HOSO$_2$-naphth-2-yl | 1-OMe |
| 413. | 3-carbazolyl | 1-OMe |
| 414. | 2-phenanthrenyl | 1-OMe |
| 415. | 5-HOSO$_2$-2-naphthyl | H |
| 416. | 8-HOSO$_2$-2-naphthyl | H |
| 417. | 2-HOSO$_2$-6-naphthyl | H |
| 418. | 6-(4-chlorophenoxy)-pyridin-3-yl | H |
| 419. | 6-(3-pyridyloxy)-pyridin-3-yl | 1-OMe |
| 420. | 6-(4-Chloro-2-cyclohexylphenoxy)-pyridin-3-yl | 1-OMe |
| 421. | 2-(2-pyridyl)-benzimidazol-5-yl | 1-OMe |
| 422. | 2-dibenzofuryl | 1-OMe |

Although the pharmacological properties of the compounds of Formulas I–VI vary with structural change, in general, activity possessed by compounds of Formulas I–VI may be demonstrated in vivo. The pharmacological properties of the compounds of this invention may be confirmed by a number of pharmacological in vitro assays. The exemplified pharmacological assays which follow have been carried out with the compounds according to the invention and their derivatives.

Biological Evaluation
Kinase Inhibition

The compounds described herein are screened in the following manner. Kinases suitable for use in the following protocol to determine kinase activity of the compounds described herein include, but are not limited to: Lck, Lyn, Src, Fyn, Syk, Zap-70, Itk, Tec, Btk, EGFR, ErbB2, Kdr, Flt-1, Flt-3, Tek, c-Met, InsR, and AKT.

Kinases are expressed as either kinase domains or full length constructs fused to glutathione S-transferase (GST) or polyHistidine tagged fusion proteins in either E. coli or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, the transfer of $^{33}PO_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The IC$_{50}$ is determined by the concentration of compound that causes a 50% reduction in the amount of $^{33}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. For example, transfer of phosphate to a peptide or polypeptide can also be detected using scintillation proximity (Wu et al., 2000), ELISA (Cleaveland et al., 1990), Fluorescence Polarization (Seethala and Menzel, 1998), and homogeneous time-resolved fluorescence (HTRF, Kolb et al., 1998). Alternatively, kinase activity can be measured using antibody-based methods whereby an antibody or polypeptide is used as a reagent to detect phosphorylated target polypeptide. Compounds of the present invention showed inhibition of IGF-1R kinase at doses less than 50 μM.

The compounds of examples 1–2, 4, 6, 8–9, 13–20, 28, 37, 39–41, 48–49, 59, 61–62, 65–66, 69, 71–72, 75–76, 84, 91–92, 94, 98–100, 105, 108–112, 118, 121, 130–131, 133–135, 137–141, 145 and 148–151 inhibited IGF-1R kinase at a level below 50 nM (IC$_{50}$).

REFERENCES

Braunwalder et al. (1996). Anal. Biochem. 234(1):23–26.
Cleaveland et al. (1990). Anal Biochem. 190(2):249–53.
Gish et al. (1995). Protein Eng. 8(6):609–614.
Kolb et al. (1998). Drug Discov. Today. 3:333–342.
Lehr et al. (1996). Gene 169(2):27527–9.
Seethala et al. (1998). Anal Biochem. 255(2):257–62.
Wu et al. (2000). Comb Chem High Throughput Screen. 3(1):27–36.

IGF-1R Assay Summary Protocols
IGF-1-Induced DNA Synthesis.

Human tumor cell lines or a rat fibroblast cell line are plated out in flat-well plates in complete medium and allowed to adhere overnight. The cells are then starved in medium containing 0.1% bovine serum albumin (BSA) overnight, pre-incubated for 1 h with or without dilutions of compound, then activated overnight with 50 ng/mL insulin-like growth factor (IGF-1). Proliferation is determined by the level of $^3$H-thymidine incorporation into DNA. IC$_{50}$'s are determined by comparing the level of thymidine incorporation found in the presence of compound compared to controls.

The compounds of examples 1, 14, 20, 48–49, 59, 84, 91, 94, 98–100, 104–105, 109–110, 118, 130, 132–135, 137, 139–140, and 148–151 inhibited 3T3 proliferation at a level below 150 nM.

IGF-1R Auto-Phosphorylation.

Murine fibroblast cells stably transfected with the human IGF-1R are plated out in flat-well plates in complete media and allowed to adhere overnight. The cells are then starved in medium containing 0.1% bovine serum albumin, pre-incubated with or without dilutions of compound, then activated for 5 min with 100 ng/mL IGF-1. The cells are lysed and proteins are separated by SDS-PAGE. The level of phosphotyrosine on IGF-1R β-chain is determined by western blotting with an anti-phospho-IGF-1Rβ-specific antibody. $IC_{50}$'s are determined by comparing the level of phosphotyrosine found in the presence of compound compared to controls.

Representative compounds tested under the following example protocols exhibit cellular activities consistent with their observed enzyme inhibition activities.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units were tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which were administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients were dissolved or suspended in suitable carrier, especially an aqueous solvent for the active ingredients. The active ingredients were preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but were not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which were commonly used include lactose and corn starch. Lubricating agents, such as magnesium stearate, were also typically added. For oral administration in a capsule form, useful diluents include lactose and dried corn starch. When aqueous suspensions and/or emulsions were administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques were known in the art.

The pharmaceutical compositions of this invention may be administered by nasal aerosol or inhalation. Such compositions were prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The foregoing is merely illustrative of the invention and is not intended to limit the invention to the disclosed compounds. Variations and changes which are obvious to one skilled in the art are intended to be within the scope and nature of the invention which are defined in the appended claims.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:
1. A compound of Formulas IIIa and IIIb

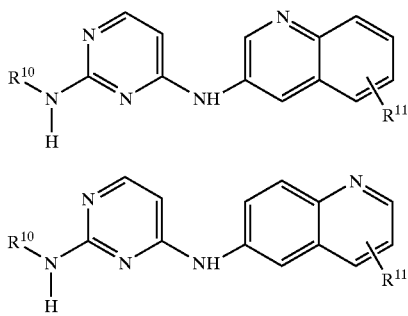

wherein $R^{10}$ is selected from phenyl and 5–10 membered heterocyclyl;
wherein $R^{10}$ is optionally substituted with 1–4 substituents selected from $R^{11}$;
wherein $R^{11}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^2$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and
$C_2$–$C_3$ alkenyl substituted with 1–3 substituents independently selected from optionally substituted phenyl and optionally substituted 5–6 membered heterocyclyl; wherein $R^{11}$ can be attached in either ring of the quinolyl substituent;
wherein $R^{12}$ is selected from H, $C_{1-6}$-alkyl, and
phenyl optionally substituted with 1–3 substituents independently selected from
$C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;
or pharmaceutically acceptable derivatives thereof;

provided in Formula IIIb $R^{10}$ is not 4-amino-2-methylquinol-6-yl when $R^{11}$ is 4-amino-2-methyl substitution.

2. Compound of claim 1 or pharmaceutically acceptable derivatives thereof selected from
$N^4$-quinolin-3-yl-$N^2$-(2,5-dimethoxyphenyl)pyrimidine-2,4-diamine;
$N^4$-quinolin-3-yl-$N^2$-(3,4-dimethoxyphenyl)pyrimidine-2,4-diamine;
$N^4$-quinolin-6-yl-$N^2$-(2,5-dimethoxyphenyl)pyrimidine-2,4-diamine;
$N^4$-quinolin-6-yl-$N^2$-(3,4-dimethoxyphenyl)pyrimidine-2,4-diamine;
$N^4$-quinolin-3-yl-$N^2$-(3,5-dimethoxyphenyl)pyrimidine-2,4-diamine;
$N^2$-benzo[1,3]dioxol-5-yl-$N^4$-quinolin-3-yl-pyrimidine-2,4-diamine;
$N^4$-quinolin-6-yl-$N^2$-(3,4-diethoxyphenyl)pyrimidine-2,4-diamine;
$N^4$-quinolin-3-yl-$N^2$-(3,4-diethoxyphenyl)pyrimidine-2,4-diamine;
$N^4$-quinolin-3-yl-$N^2$-(2-methoxyphenyl)pyrimidine-2,4-diamine;
$N^4$-quinolin-6-yl-$N^2$-(2-methoxyphenyl)pyrimidine-2,4-diamine;
$N^4$-quinolin-3-yl-$N^2$-(3-methoxyphenyl)pyrimidine-2,4-diamine;
$N^4$-quinolin-6-yl-$N^2$-(3-methoxyphenyl)pyrimidine-2,4-diamine;
$N^4$-quinolin-3-yl-$N^2$-(3-ethylphenyl)pyrimidine-2,4-diamine;
$N^4$-quinolin-6-yl-$N^2$-(3-ethylphenyl)pyrimidine-2,4-diamine;
$N^4$-quinolin-3-yl-$N^2$-(4-ethylphenyl)pyrimidine-2,4-diamine;
$N^4$-quinolin-6-yl-$N^2$-(4-ethylphenyl)pyrimidine-2,4-diamine;
$N^2$-(3-ethynylphenyl)-$N^4$-quinolin-3-yl-pyrimidine-2,4-diamine;
$N^2$-(3-ethynylphenyl)-$N^4$-quinolin-6-yl-pyrimidine-2,4-diamine;
$N^2$-(3-cyanophenyl)-$N^4$-quinolin-6-yl-pyrimidine-2,4-diamine;
$N^4$-quinolin-3-yl-$N^2$-(4-methoxyphenyl)pyrimidine-2,4-diamine;
$N^4$-quinolin-6-yl-$N^2$-(4-methoxyphenyl)pyrimidine-2,4-diamine;
$N^4$-quinolin-3-yl-$N^2$-(3-quinolinyl)pyrimidine-2,4-diamine;
$N^4$-quinolin-6-yl-$N^2$-(3-quinolinyl)pyrimidine-2,4-diamine;
$N^4$-quinolin-3-yl-$N^2$-(6-quinolinyl)pyrimidine-2,4-diamine;
$N^4$-quinolin-6-yl-$N^2$-(6-quinolinyl)pyrimidine-2,4-diamine;
$N^2$-quinolin-6-yl-N-(3,4,5-trimethoxyphenyl)-pyrimidine-2,4-diamine;
$N^2$-(3-aminosulfonylphenyl)-$N^4$-quinolin-6-yl-pyrimidine-2,4-diamine;
$N^2$-(3-aminosulfonylphenyl)-$N^4$-quinolin-3-yl-pyrimidine-2,4-diamine;
$N^2$-(4-aminosulfonylphenyl)-$N^4$-quinolin-6-yl-pyrimidine-2,4-diamine;

N²-(4-aminosulfonylphenyl)-N⁴-quinolin-3-yl-pyrimidine-2,4-diamine;

N²-(3,4-dimethoxy-6-methylphenyl)-N⁴-quinolin-6-yl-pyrimidine-2,4-diamine; and

N²-(3,4-dimethoxy-6-methylphenyl)-N⁴-quinolin-3-yl-pyrimidine-2,4-diamine.

3. Compound of Formula I'

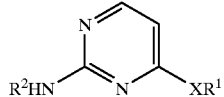

wherein X is selected from O, NH and NR;

wherein R is selected from methyl, optionally substituted phenyl, —(CH₂)₂₋₃—Rᵃ, —C₂₋₃-alkenyl-Rᵃ, and —C₂₋₃-alkynyl-Rᵃ;

wherein Rᵃ is independently selected from H, optionally substituted phenyl, optionally substituted 5–6-membered heterocyclyl, and —NRᵇRᵇ;

wherein Rᵇ is independently selected from H, C₁₋₃ alkyl, optionally substituted phenyl, and optionally substituted 5–6-membered heterocyclyl;

wherein R¹ is selected from 3-quinolyl, wherein R¹ is optionally substituted with 1–3 substituents independently selected from R³;

wherein R² is selected from R⁴ and aryl optionally substituted with 1–3 substituents independently selected from R³;

wherein R³ is independently selected from H, halo, C₁₋₃-alkyl, C₂₋₃-alkenyl, C₂₋₃-alkynyl, phenyl, hydroxy, C₁₋₃-haloalkoxy, C₁₋₃-alkoxy, —C(O)—C₁₋₃-alkyl, and C₁₋₃-haloalkyl; and wherein R⁴ is independently selected from 2,3-dihydro-indolyl, 1,3-benzodioxolyl, indolyl, 1,3-dioxo-isoindolyl, indazolyl, pyridyl, quinolyl, isoquinolyl, benzothiazolyl, 1,2,3-benzotriazolyl, benzimidazolyl, and pyridyl; wherein R⁴ is optionally substituted with hydroxy, C₁₋₃-alkoxy, cyano, nitro, halo, C₁₋₃-alkyl, di-C₁₋₃-alkylamino, di-C₁₋₃-alkylamino-C₁₋₃-alkyl, di-C₁₋₃-alkylamino-C₁₋₃-alkoxy, C₁₋₃-alkylcarbonyl, C₁₋₃-alkoxycarbonyl, C₁₋₃-alkylcarbonylamino, pyrrolidinylcarbonyl-C₂₋₃-alkenyl, pyrrolidinylcarbonyl-C₁₋₃-alkyl, pyrrolidinyl-C₁₋₃-alkyl, C₂₋₃-alkynyl, acetyl, C₁₋₃-alkylcarbonyl-C₁₋₃-alkyl, carboxy-C₁₋₃-alkyl, (piperidinyl)-C₁₋₃-alkoxy, (piperazinyl)-C₁₋₃-alkoxy, 2-morpholinyl-C₁₋₃-alkoxy, C₁₋₃-haloalkyl, C₁₋₃-haloalkoxy, aminocarbonyl, aminosulfonyl, C₁₋₃-alkylaminosulfonyl, hydroxy-C₁₋₃-alkylaminosulfonyl, (thiazolyl) aminosulfonyl, C₁₋₄-alkylaminosulfonyl, C₁₋₃-alkylcarbonylaminosulfonyl, C₁₋₃-alkylsulfonyl, C₁₋₃-alkoxycarbonyl-piperazinyl, morpholinyl, piperazinyl, C₁₋₃-alkylpiperazinyl, and oxazolyl;

or pharmaceutically acceptable salts thereof.

4. Compound of claim 3 wherein X is selected from NH and NR;

wherein R is selected from methyl, —(CH₂)₂₋₃—Rᵃ, —C₂₋₃-alkenyl-Rᵃ, and 2,6-disubstituted phenyl;

wherein Rᵃ is independently selected from H, optionally substituted phenyl, optionally substituted 5–6-membered heterocyclyl, and —NRᵇRᵇ;

wherein Rᵇ is independently selected from H, C₁₋₃ alkyl, optionally substituted phenyl, and optionally substituted 5–6-membered heterocyclyl;

wherein R¹ is selected from 3-quinolyl, and 6-quinolyl, wherein R¹ is optionally substituted with 1–2 substituents independently selected from R³;

wherein R² is selected from 2-naphthyl, 2,3-dihydro-indol-6-yl, 1,3-benzodioxol-5-yl, 5-indolyl, 4-indolyl, 1,3-dioxo-isoindol-5-yl, 5-indazolyl, 6-indazolyl, 3-pyridyl, 3-quinolyl, 6-quinolyl, isoquinolyl, benzothiazol-6-yl, benzothiazol-5-yl, 1,2,3-benzotriazol-5-yl, 6-benzimidazolyl, 5-pyridyl, and phenyl;

wherein R² is optionally substituted with 1–3 substituents independently selected from hydroxy, methoxy, ethoxy, cyano, nitro, chloro, fluoro, bromo, dimethylamino, dimethylaminoethyl, 3-dimethylamino-propoxy, methoxycarbonyl, methylcarbonyl, methylcarbonylamino, methyl, ethyl, pyrrolidin-1-ylcarbonylethenyl, pyrrolidin-1-ylcarbonylethyl, pyrrolidin-1-ylpropyl, ethynyl, acetyl, ethoxycarbonylbutyl, carboxybutyl, 2-(1-methyl-piperidin-4-yl)-ethoxy, 2-(4-methyl-piperazin-1-yl)ethoxy, 3-(4-methyl-piperazin-1-yl)-propoxy, 3-(piperidin-1-yl)propoxy, 2-piperidin-1-yl-ethoxy, 2-morpholin-4-yl-ethoxy, pentafluoroethyl, trifluoromethyl, trifluoromethoxy, difluoromethoxy, aminocarbonyl, aminosulfonyl, N,N'-di-propylaminosulfonyl, hydroxypropylaminosulfonyl, (2-thiazolyl) aminosulfonyl, butylaminosulfonyl, methylcarbonylaminosulfonyl, methylsulfonyl, 1-methyl-piperidin-4-ylmethoxy, 1-tert-butoxycarbonyl-piperazin-4-yl, 4-morpholinyl, 4-methylpiperzin-1-yl, 4-piperazinyl, 4-isopropyl-piperazin-1-yl, and oxazol-5-yl; and wherein R³ is selected from H, hydroxy, iodo, methyl, acetyl, trifluoromethyl, methoxy, phenyl and trifluoromethoxy;

or pharmaceutically acceptable salts thereof.

5. Compound of claim 3 wherein X is NH; or pharmaceutically acceptable salts thereof.

6. Compound of claim 3 wherein R¹ is 3-quinolyl; or pharmaceutically acceptable salts thereof.

7. Compound of claim 3 or pharmaceutically acceptable derivatives thereof selected from N⁴-Quinolin-3-yl-N²-(3,4,5-trimethoxyphenyl) pyrimidine-2,4-diamine;

N⁴-quinolin-6-yl-N²-(3,4,5-trimethoxyphenyl)-pyrimidine-2,4-diamine;

N²-(3,4-dimethoxy-6-methylphenyl)-N⁴-quinolin-3-yl-pyrimidine-2,4-diamine;

N²-(6-(4-morpholinyl)-3-pyridinyl)-N⁴-(3-quinolinyl)-2,4-pyrimidinediamine;

N²-(4-bromo-2-fluorophenyl)-N⁴-(3-quinolinyl)-2,4-pyrimidinediamine;

N²-(4-bromophenyl)-N⁴-(3-quinolinyl)-2,4-pyrimidinediamine;

N²-(4-(4-methyl-1-piperazinyl)phenyl)-N⁴-(3-quinolinyl)-2,4-pyrimidinediamine;

2-(Methoxy)-4-((4-(3-quinolinylamino)-2-pyrimidinyl)amino)benzamide;

N²-[4-(3-Piperidin-1-yl-propoxy)-phenyl]-N⁴-quinolin-3-yl-pyrimidine-2,4-diamine;

N²-(4-((2-(1-Piperidinyl)ethyl)oxy)phenyl)-N⁴-(3-quinolinyl)-2,4-pyrimidinediamine;

N²-(3-(2-(Dimethylamino)ethyl)-4-(methoxy)phenyl)-N⁴-(3-quinolinyl)-2,4-pyrimidinediamine;

N²-(3-(1,3-oxazol-5-yl)phenyl)-N⁴-(3-quinolinyl)-2,4-pyrimidinediamine;
N²-(3-(1,3-oxazol-5-yl)phenyl)-N⁴-(6-quinolinyl)-2,4-pyrimidinediamine;
N²-(3-(methoxy)-4-(1,3-oxazol-5-yl)phenyl)-N⁴-(3-quinolinyl)-2,4-pyrimidinediamine;
N²-(1-acetyl-3,3-dimethyl-2,3-dihydro-1H-indol-6-yl)-N⁴-(3-quinolinyl)-2,4-pyrimidinediamine;
N⁴-(2-Methyl-6-quinolinyl)-N²-(3,4,5-tris(methoxy)phenyl)-2,4-pyrimidinediamine;
N²-[3-Methoxy-4-(2-{4-[4-(quinolin-3-ylamino)-pyrimidin-2-yl]-piperazin-1-yl}-ethoxy)-phenyl]-N⁴-quinolin-3-yl-pyrimidine-2,4-diamine;
N² (3-Methoxy-4-morpholin-4-yl-phenyl)-N⁴-quinolin-3-yl-pyrimidine-2,4-diamine;
N²-(3,4,5-Trimethoxyphenyl)-N⁴-(6-methoxy-quinolin-3-yl)-2,4-pyrimidinediamine;
N²-(2-Methyl-4,5-dimethoxyphenyl)-N⁴-(6-methoxy-quinolin-3-yl)-2,4-pyrimidinediamine;
N²-(3,4,5-Trimethoxyphenyl)-N⁴-(6-trifluoromethoxy-quinolin-3-yl)-2,4-pyrimidinediamine;
3-{2-Methoxy-4-[4-(quinolin-3-ylamino)-pyrimidin-2-ylamino]-phenyl}-1-pyrrolidin-1-yl-propenone;
3-{2-Methoxy-4-[4-(quinolin-3-ylamino)-pyrimidin-2-ylamino]-phenyl}-1-pyrrolidin-1-yl-propanone;
N²-[3-Methoxy-4-(3-pyrrolidin-1-yl-propyl)-phenyl]-N⁴-quinolin-3-yl-pyrimidine-2,4-diamine; and
N²-[3-Methoxy-4-(2-{1-[4-(quinolin-3-ylamino)-pyrimidin-2-yl]-piperidin-4-yl}-ethoxy)-phenyl]-N⁴-quinolin-3-yl-pyrimidine-2,4-diamine.

8. A compound of Formula IV

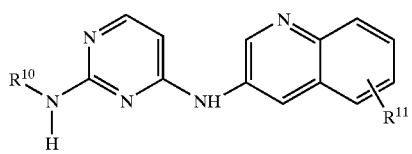

IV wherein R¹⁰ is selected from phenyl, naphthyl, and 5–10 membered heterocyclyl; wherein R¹⁰ is optionally substituted with 1–4 substituents selected from R¹³;
wherein R¹¹ is one or more substituents selected from H, $C_1$–$C_4$ alkyl, $C_1$–$C_4$ haloalkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{14}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and
$C_2$–$C_3$ alkenyl substituted with 1–3 substituents independently selected from optionally substituted phenyl and optionally substituted 5–6 membered heterocyclyl;
wherein R¹¹ can be attached in either ring of the quinolyl substituent;
wherein R¹² is selected from H, $C_{1-6}$-alkyl, $C_{1-6}$-haloalkyl, $C_1$–$C_3$ alkyl substituted with 1–3 substituents independently selected from optionally substituted phenyl and optionally substituted 5–6 membered heterocyclyl;

wherein optionally substituted phenyl and optionally substituted 5–6 membered heterocyclyl are substituted with 1–3 substituents independently selected from
$C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl optionally substituted with one or more substituents selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl; and
phenyl optionally substituted with 1–3 substituents independently selected from
$C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;
wherein R¹³ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and
$C_2$–$C_3$ alkenyl substituted with 1–3 substituents independently selected from optionally substituted phenyl and optionally substituted 5–6 membered heterocyclyl; and
wherein R¹⁴ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and
phenyl optionally substituted with 1–3 substituents independently selected from
$C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;
or pharmaceutically acceptable derivatives thereof.

9. Compound of claim 8 wherein R¹⁰ is selected from 3,4,5-trimethoxyphenyl, 3,4-dimethoxyphenyl, 3,5-dimethoxyphenyl, 3,4-dimethoxy-6-cyanophenyl, 2,5-dimethoxyphenyl, 2-methoxyphenyl, 3-methoxyphenyl, 4-methoxyphenyl, 3-(dimethylaminoethyl)-4-methoxyphenyl, 4-methoxy-2-nitrophenyl, 2-methoxy-4-nitrophenyl, 3,4-dimethoxy-6-methylphenyl, 4-(3-dimethylamino-propoxy)-phenyl, 4-(1-tert-butoxycarbonyl-piperazin-4-yl)phenyl, 4-(4-piperazinyl)phenyl, 3,5-dimethoxy-4-[2-(4-methyl-piperazin-1-yl)-ethoxy]-phenyl, 3,5-dimethoxy-4-[3-(4-methyl-piperazin-1-yl)-propoxy]-phenyl, 3-methoxy-4-[2-(4-methyl-piperazin-1-yl)-ethoxy]- phenyl, 3-methoxy-4-[3-(4-methyl-piperazin-1-yl)-propoxy]-phenyl, 3,4-dimethoxy-5-[3-(4-methyl-piperazin-1-yl)-propoxy]-phenyl, 3-methoxy-4-(1-methyl-piperidin-4-ylmethoxy)-phenyl, 3-methoxy-4-[2-(1-methyl-piperidin-4-yl)-ethoxy]-phenyl, 3-fluoro-4-(4-methyl-piperazin-1-yl)-phenyl, 3-fluoro-4-(3-piperidin-1-yl-propoxy)-phenyl, 4-(4-isopropyl-piperazin-1-yl)-phenyl, 2-methyl-4-(4-methyl-piperazin-1-yl)-phenyl, 2-fluoro-4,5-dimethoxy-phenyl, 2-methyl-4-[3-(4-methyl-piperazin-1-yl)-propoxy]-phenyl, 2-methyl-4-(3-piperidin-1-yl-propoxy)-phenyl, 3,5-dimethoxy-4-(2-piperidin-1-yl-ethoxy)-phenyl, 3,5-dimethoxy-4-(2-morpholin-4-yl-ethoxy)-phenyl, 4-[2-(4-methyl-piperazin-1-yl)-ethoxy]-phenyl, 3-fluoro-4-[3-(4-methyl-piperazin-1-yl)-propoxy]-phenyl, 3-fluoro-4-[2-(4-methyl-piperazin-1-yl)-ethoxy]-phenyl, 3-fluoro-4-(2-piperidin-1-yl-ethoxy)-phenyl, 4-(1-tert-butoxycarbonyl-piperazin-4-yl)-3-difluoromethoxy-phenyl, 2-ethoxycarbonylbutyl-4,5-dimethoxyphenyl, 2-carboxybutyl-4,5-dimethoxyphenyl, 3-methoxy-4-(2-{4-[4-(quinolin-3-ylamino)-pyrimidin-2-yl]-piperazin-1-yl}-ethoxy)-phenyl, 3-methoxy-4-(2-{1-[4-(quinolin-3-ylamino)-pyrimidin-2-yl]-piperidin-4-yl}-ethoxy)-phenyl, 3,4-diethoxyphenyl, 3-methoxy-4-(pyrrolidin-1-ylcarbonylethenyl)phenyl, 3-methoxy-4-(pyrrolidin-1-ylcarbonylethyl)phenyl, 3-methoxy-4-(pyrrolidin-1-ylpropyl)phenyl, 4-[3-(piperidin-1-yl)propoxy]phenyl, 4-(2-(piperidin-1-yl)ethoxy)phenyl, 6-benzimidazolyl, 4-(methylcarbonylaminosulfonyl)phenyl, 4-(N,N'-dipropylaminosulfonyl)phenyl, 3-butylaminosulfonylphenyl, 3-hydroxypropylaminosulfonylphenyl, 3-[(2-thiazolyl)aminosulfonyl]phenyl, 3-aminosulfonylphenyl, 4-aminosulfonylphenyl, 4-methylsulfonylphenyl, 3-quinolyl, 6-quinolyl, 6-hydroxy-3-quinolyl, indol-4-yl, benzothiazol-6-yl, benzothiazol-5-yl, 1,2,3-benzotriazol-5-yl, 4-(4-morpholinyl)phenyl, 4-(4-methylpiperzin-1-yl)phenyl, 3-methoxy-4-(4-morpholinyl)phenyl, 4-methoxycarbonylphenyl, 3-methoxycarbonylphenyl, 4-(dimethylamino)phenyl, 3-(dimethylamino)phenyl, 4-(dimethylamino)-2-methylphenyl, 3-ethylphenyl, 4-ethylphenyl, 4-nitrophenyl, 4-(methylcarbonylamino)phenyl, 3-(methylcarbonylamino)phenyl, 4-methylcarbonylphenyl, 3-aminocarbonylphenyl, 4-aminocarbonylphenyl, 4-aminocarbonyl-3-methoxyphenyl, 3-fluoro-4-methoxyphenyl, 3-chloro-4-methoxyphenyl, 3-trifluoromethoxyphenyl, 4-trifluoromethoxyphenyl, 3-chloro-4-trifluoromethoxyphenyl, 3,5-ditrifluoromethylphenyl, 3-fluoro-5-trifluoromethylphenyl, 4-fluoro-3-trifluoromethylphenyl, 3-methoxy-5-trifluoromethylphenyl, 3-methoxy-4-pentafluoroethylphenyl, 5-indazolyl, 6-indazolyl, 1-methyl-indazol-5-yl, 3-pyridyl, 6-methoxy-3-pyridyl, 2-(4-morpholinyl)-5-pyridyl, 4-bromo-2-fluorophenyl, 2-fluorophenyl, 3-fluorophenyl, 4-fluorophenyl, 2-bromophenyl, 3-bromophenyl, 4-bromophenyl, 3-chloro-4-fluorophenyl, 3-chlorophenyl, 3,4-dichlorophenyl, 3,5-dichlorophenyl, 4-chlorophenyl, 3-ethynylphenyl, 3-cyanophenyl, 2,2-difluoro-1,3-benzodioxol-5-yl, 1,3-benzodioxol-5-yl, 2-methyl-1,3-dioxo-isoindol-5-yl, 3-(oxazol-5-yl)phenyl, 4-(oxazol-5-yl)phenyl, 3-methoxy-4-(oxazol-5-yl)phenyl, 2-naphthyl, 5-indolyl, 1-acetyl-2,3-dihydro-3,3-dimethylindol-6-yl, and 2,3-dihydro-3,3-dimethylindol-6-yl;

wherein $R^{11}$ is one or more substituents selected from H, hydroxy, methyl, acetyl, trifluoromethyl, methoxy, phenyl and trifluoromethoxy;

or pharmaceutically acceptable derivatives thereof.

10. Compound of claim 8 wherein $R^{10}$ is selected from 3,4,5-trimethoxyphenyl, 3-(dimethylaminoethyl)-4-methoxyphenyl, 4-[3-(piperidin-1-yl)propoxy]phenyl, 3-methoxy-4-(pyrrolidin-1-ylpropyl)phenyl, and 3,4-dimethoxy-6-methylphenyl; and wherein $R^{11}$ is selected from H, methoxy, and trifluoromethoxy; wherein $R^{11}$ is attached at position 6 or 7 of the quinolyl substituent; or pharmeceutically acceptable salts thereof.

11. Compound of claim 8 or pharmaceutically acceptable derivatives thereof selected from $N^4$-Quinolin-3-yl-$N^2$-(3,4,5-trimethoxyphenyl) pyrimidine-2,4-diamine;

$N^2$-(3,4-dimethoxy-6-methylphenyl)-$N^4$-quinolin-3-yl-pyrimidine-2,4-diamine;

$N^2$-(6-(4-morpholinyl)-3-pyridinyl)-$N^4$-(3-quinolinyl)-2,4-pyrimidinediamine;

$N^2$-(4-bromo-2-fluorophenyl)-$N^4$-(3-quinolinyl)-2,4-pyrimidinediamine;

$N^2$-(4-bromophenyl)-$N^4$-(3-quinolinyl)-2,4-pyrimidinediamine;

$N^2$-(4-(4-methyl-1-piperazinyl)phenyl)-$N^4$-(3-quinolinyl)-2,4-pyrimidinediamine;

2-(Methoxy)-4-((4-(3-quinolinylamino)-2-pyrimidinyl)amino)benzamide;

$N^2$-[4-(3-Piperidin-1-yl-propoxy)-phenyl]-$N^4$-quinolin-3-yl-pyrimidine-2,4-diamine;

$N^2$-(4-((2-(1-Piperidinyl)ethyl)oxy)phenyl)-$N^4$-(3-quinolinyl)-2,4-pyrimidinediamine;

$N^2$-(3-(2-(Dimethylamino)ethyl)-4-(methoxy)phenyl)-$N^4$-(3-quinolinyl)-2,4-pyrimidinediamine;

$N^2$-(3-(1,3-oxazol-5-yl)phenyl)-$N^4$-(3-quinolinyl)-2,4-pyrimidinediamine;

$N^2$-(3-(methoxy)-4-(1,3-oxazol-5-yl)phenyl)-$N^4$-(3-quinolinyl)-2,4-pyrimidinediamine;

$N^2$-(1-acetyl-3,3-dimethyl-2,3-dihydro-1H-indol-6-yl)-$N^4$-(3-quinolinyl)-2,4-pyrimidinediamine;

$N^2$-[3-Methoxy-4-(2-{4-[4-(quinolin-3-ylamino)-pyrimidin-2-yl]-piperazin-1-yl}-ethoxy)-phenyl]-N-4-quinolin-3-yl-pyrimidine-2,4-diamine;

$N^2$-(3-Methoxy-4-morpholin-4-yl-phenyl)-N-4-quinolin-3-yl-pyrimidine-2,4-diamine;

$N^2$-(3,4,5-Trimethoxyphenyl)-$N^4$-(6-methoxy-quinolin-3-yl)-2,4-pyrimidinediamine;

$N^2$-(2-Methyl-4,5-dimethoxyphenyl)-$N^4$-(6-methoxy-quinolin-3-yl)-2,4-pyrimidinediamine;

$N^2$-(3,4,5-Trimethoxyphenyl)-$N^4$-(6-trifluoromethoxy-quinolin-3-yl)-2,4-pyrimidinediamine;

3-{2-Methoxy-4-[4-(quinolin-3-ylamino)-pyrimidin-2-ylamino]-phenyl}-1-pyrrolidin-1-yl-propenone;

3-{2-Methoxy-4-[4-(quinolin-3-ylamino)-pyrimidin-2-ylamino]-phenyl}-1-pyrrolidin-1-yl-propanone;

$N^2$-[3-Methoxy-4-(3-pyrrolidin-1-yl-propyl)-phenyl]-$N^4$-quinolin-3-yl-pyrimidine-2,4-diamine; and $N^2$-[3-Methoxy-4-(2-{1-[4-(quinolin-3-ylamino)-pyrimidin-2-yl]-piperidin-4-yl}-ethoxy)-phenyl]-$N^4$-quinolin-3-yl-pyrimidine-2,4-diamine.

12. A compound of Formula V

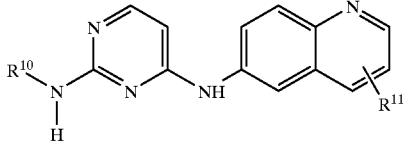

wherein $R^{10}$ is selected from phenyl, naphthyl, and 5–10 membered heterocyclyl; wherein $R^{10}$ is optionally substituted with 1–4 substituents selected from $R^{13}$;

wherein $R^{11}$ is one or more substituents selected from H, $C_1$–$C_4$ alkyl, $C_1$–$C_4$ haloalkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{14}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{11}$ can be attached in either ring of the quinolyl substituent;

wherein $R^{12}$ is selected from H, $C_{1-6}$-alkyl, $C_{1-6}$-haloalkyl, $C_1$–$C_3$ alkyl substituted with 1–3 substituents independently selected from optionally substituted phenyl and optionally substituted 5–6 membered heterocyclyl;

wherein optionally substituted phenyl and optionally substituted 5–6 membered heterocyclyl are substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl optionally substituted with one or more substituents selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, phenyl, 5–6 membered heterocyclyl optionally substituted with one or more substituents selected from alkyl, $C_{1-4}$-alkylaminocarbonyl, aminocarbonyl, aminosulfonyl, acetyl, phenyl, and 5–6 membered heterocyclyl; and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;

wherein $R^{13}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, bromo, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl; and wherein $R^{14}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-16}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

or pharmaceutically acceptable derivatives thereof; provided $R^{10}$ is not 4-amino-2-methylquinol-6-yl when $R^{11}$ is 4-amino-2-methyl substitution.

13. Compound of claim 12 wherein $R^{10}$ is selected from 3,4,5-trimethoxyphenyl, 3,4-dimethoxyphenyl, 3,5-dimethoxyphenyl, 3,4-dimethoxy-6-cyanophenyl, 2,5-dimethoxyphenyl, 2-methoxyphenyl, 3-methoxyphenyl, 4-methoxyphenyl, 3-(dimethylaminoethyl)-4-methoxyphenyl, 4-methoxy-2-nitrophenyl, 2-methoxy-4-nitrophenyl, 3,4-dimethoxy-6-methylphenyl, 4-(3-dimethylamino-propoxy)-phenyl, 4-(1-tert-butoxycarbonyl-piperazin-4-yl)phenyl, 4-(4-piperazinyl)phenyl, 3,5-dimethoxy-4-[2-(4-methyl-piperazin-1-yl)-ethoxy]-phenyl, 3,5-dimethoxy-4-[3-(4-methyl-piperazin-1-yl)-propoxy]-phenyl, 3-methoxy-4-[2-(4-methyl-piperazin-1-yl)-ethoxy]-phenyl, 3-methoxy-4-[3-(4-methyl-piperazin-1-yl)-propoxy]-phenyl, 3,4-dimethoxy-5-[3-(4-methyl-piperazin-1-yl)-propoxy]-phenyl, 3-methoxy-4-(1-methyl-piperidin-4-ylmethoxy)-phenyl, 3-methoxy-4-[2-(1-methyl-piperidin-4-yl)-ethoxy]-phenyl, 3-fluoro-4-(4-methyl-piperazin-1-yl)-phenyl, 3-fluoro-4-(3-piperidin-1-yl-propoxy)-phenyl, 4-(4-isopropyl-piperazin-1-yl)-phenyl, 2-methyl-4-(4-methyl-piperazin-1-yl)-phenyl, 2-fluoro-4,5-dimethoxy-phenyl, 2-methyl-4-[3-(4-methyl-piperazin-1-yl)-propoxy]-phenyl, 2-methyl-4-(3-piperidin-1-yl-propoxy)-phenyl, 3,5-dimethoxy-4-(2-piperidin-1-yl-ethoxy)-phenyl, 3,5-dimethoxy-4-(2-morpholin-4-yl-ethoxy)-phenyl, 4-[2-(4-methyl-piperazin-1-yl)-ethoxy]-phenyl, 3-fluoro-4-[3-(4-methyl-piperazin-1-yl)-propoxy]-phenyl, 3-fluoro-4-[2-(4-methyl-piperazin-1-yl)-ethoxy]-phenyl, 3-fluoro-4-(2-piperidin-1-yl-ethoxy)-phenyl, 4-(1-tert-butoxycarbonyl-piperazin-4-yl)-3-difluoromethoxy-phenyl, 2-ethoxycarbonylbutyl-4,5-dimethoxyphenyl, 2-carboxybutyl-4,5-dimethoxyphenyl, 3-methoxy-4-(2-{4-[4-(quinolin-3-ylamino)-pyrimidin-2-yl]-piperazin-1-yl}-ethoxy)-phenyl, 3-methoxy-4-(2-{1-[4-(quinolin-3-ylamino)-pyrimidin-2-yl]-piperidin-4-yl}-ethoxy)-phenyl, 3,4-diethoxyphenyl, 3-methoxy-4-(pyrrolidin-1-ylcarbonylethenyl)phenyl, 3-methoxy-4-(pyrrolidin-1-ylcarbonylethyl)phenyl, 3-methoxy-4-(pyrrolidin-1-ylpropyl)phenyl, 4-[3-(piperidin-1-yl)propoxy]phenyl, 4-(2-(piperidin-1-yl)ethoxy)phenyl, 6-benzimidazolyl, 4-(methylcarbonylaminosulfonyl)phenyl, 4-(N,N'-dipropylaminosulfonyl)phenyl, 3-butylaminosulfonylphenyl, 3-hydroxypropylaminosulfonylphenyl, 3-[(2-thiazolyl) aminosulfonyl]phenyl, 3-aminosulfonylphenyl, 4-aminosulfonylphenyl, 4-methylsulfonylphenyl, 3-quinolyl, 6-quinolyl, 6-hydroxy-3-quinolyl, indol-4-yl, benzothiazol-6-yl, benzothiazol-5-yl, 1,2,3-benzotriazol-5-yl, 4-(4-morpholinyl)phenyl, 4-(4-methylpiperzin-1-yl) phenyl, 3-methoxy-4-(4-morpholinyl)phenyl, 4-methoxycarbonylphenyl, 3-methoxycarbonylphenyl, 4-(dimethylamino)phenyl, 3-(dimethylamino)phenyl, 4-(dimethylamino)-2-methylphenyl, 3-ethylphenyl, 4-ethylphenyl, 4-nitrophenyl, 4-(methylcarbonylamino) phenyl, 3-(methylcarbonylamino)phenyl, 4-methylcarbonylphenyl, 3-aminocarbonylphenyl, 4-aminocarbonylphenyl, 4-aminocarbonyl-3-methoxyphenyl, 3-fluoro-4-methoxyphenyl, 3-chloro-4-methoxyphenyl, 3-trifluoromethoxyphenyl, 4-trifluoromethoxyphenyl, 3-chloro-4-trifluoromethoxyphenyl, 3,5-ditrifluoromethylphenyl, 3-fluoro-5-trifluoromethylphenyl, 4-fluoro-3-trifluoromethylphenyl, 3-methoxy-5-trifluoromethylphenyl, 3-methoxy-4-pentafluoroethylphenyl, 5-indazolyl, 6-indazolyl, 1-methyl-indazol-5-yl, 3-pyridyl, 6-methoxy-3-pyridyl, 2-(4-morpholinyl)-5-pyridyl, 4-bromo-2-fluorophenyl, 2-fluorophenyl, 3-fluorophenyl, 4-fluorophenyl, 2-bromophenyl, 3-bromophenyl, 4-bromophenyl, 3-chloro-4-fluorophenyl, 3-chlorophenyl, 3,4-dichlorophenyl, 3,5-dichlorophenyl, 4-chlorophenyl, 3-ethynylphenyl, 3-cyanophenyl, 2,2-difluoro-1,3-benzodioxol-5-yl, 1,3-benzodioxol-5-yl, 2-methyl-1,3-dioxo-isoindol-5-yl, 3-(oxazol-5-yl)phenyl, 4-(oxazol-5-yl) phenyl, 3-methoxy-4-(oxazol-5-yl)phenyl, 2-naphthyl, 5-indolyl, 1-acetyl-2,3-dihydro-3,3-dimethylindol-6-yl, and 2,3-dihydro-3,3-dimethylindol-6-yl;

wherein $R^{11}$ is selected from H, hydroxy, methyl, acetyl, trifluoromethyl, methoxy, phenyl and trifluoromethoxy;

or pharmaceutically acceptable derivatives thereof.

14. Compound of claim 12 wherein $R^{10}$ is selected from 3,4,5-trimethoxyphenyl, 3-(dimethylaminoethyl)-4-methoxyphenyl, 3-(1,3-oxazol-5-yl)phenyl, 4-[3-(piperidin-1-yl)propoxy]phenyl, 3-methoxy-4-(pyrrolidin-1-ylpropyl) phenyl, and 3,4-dimethoxy-6-methylphenyl; and wherein $R^{11}$ is selected from H, methoxy, and trifluoromethoxy; wherein $R^{11}$ is attached at position 6 or 7 of the quinolyl ring; or pharmaceutically acceptable salts thereof.

15. Compound of claim 12 or pharmaceutically acceptable derivatives thereof selected from $N^4$-quinolin-6-yl-$N^2$-(3,4,5-trimethoxyphenyl)-pyrimidine-2,4-diamine;

$N^2$-(3-(1,3-oxazol-5-yl)phenyl)-$N^4$-(6-quinolinyl)-2,4-pyrimidinediamine; and $N^4$-(2-Methyl-6-quinolinyl)-$N^2$-(3,4,5-tris(methoxy) phenyl)-2,4-pyrimidinediamine.

16. A composition comprising a compound according to claim 13 and a pharmaceutically acceptable carrier.

17. A method of treating breast cancer in a subject, said method comprising administering an effective amount of a compound of claim 13.

* * * * *

UNITED STATES PATENT AND TRADEMARK OFFICE
CERTIFICATE OF CORRECTION

PATENT NO. : 6,939,874 B2  Page 1 of 1
APPLICATION NO. : 10/225783
DATED : September 6, 2005
INVENTOR(S) : Jean-Christophe Hermanage et al.

It is certified that error appears in the above-identified patent and that said Letters Patent is hereby corrected as shown below:

Column 149, Line 67: Change . . . acceptable derivatives thereof; to . . . acceptable salts thereof;

Column 150, Line 5: change derivatives thereof . . . to salts thereof . . .

Column 150, Line 60: Change the compound name beginning with $N^2$-quinolin-6-yl-N-(3 . . . to the name beginning with $N^4$-quinolin-6-yl-$N^2$-(3

Column 151, Line 7: Change Compound of . . . to A compound of . . .

Column 151, Line 25: Change 3-quinolyl . . . to 3-quinolyl and 6-quinolyl . . .

Column 152, Line 43: Change derivatives thereof . . . to salts thereof . . .

Column 154, Line 55: Change acceptable derivatives . . . to acceptable salts . . .

Column 155, Line 65: Change acceptable derivatives . . . to acceptable salts . . .

Column 156, Line 6: Change pharmeceutically acceptable . . . to pharmaceutically acceptable . . .

Column 158, Line 24: Change acceptable derivatives . . . to acceptable salts . . .

Column 160, Line 6: Change acceptable derivatives . . . to acceptable salts . . .

Column 160, Line 17: Change acceptable derivatives . . . to acceptable salts . . .

Signed and Sealed this

Seventeenth Day of June, 2008

JON W. DUDAS
*Director of the United States Patent and Trademark Office*